US009139842B2

(12) United States Patent
Albert et al.

(10) Patent No.: US 9,139,842 B2
(45) Date of Patent: Sep. 22, 2015

(54) METHODS AND COMPOSITIONS FOR TARGETING SEQUENCES OF INTEREST TO THE CHLOROPLAST

(75) Inventors: Henrik Albert, Alameda, CA (US); Linda A. Castle, Mountain View, CA (US); Matthew Heckert, Union City, CA (US); Jian Lu, Union City, IA (US); Daniel L. Siehl, Menlo Park, CA (US); Yumin Tao, Urbandale, IA (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 215 days.

(21) Appl. No.: 13/208,960

(22) Filed: Aug. 12, 2011

(65) Prior Publication Data

US 2012/0042412 A1    Feb. 16, 2012

Related U.S. Application Data

(60) Provisional application No. 61/401,456, filed on Aug. 13, 2010, provisional application No. 61/393,507, filed on Oct. 15, 2010, provisional application No. 61/501,042, filed on Jun. 24, 2011.

(51) Int. Cl.
*C12N 15/82* (2006.01)
*C12N 9/02* (2006.01)

(52) U.S. Cl.
CPC .......... *C12N 15/8274* (2013.01); *C12N 9/0069* (2013.01); *C12N 15/8221* (2013.01)

(58) Field of Classification Search
None
See application file for complete search history.

(56) References Cited

U.S. PATENT DOCUMENTS

2005/0193445 A1    9/2005   Cahoon et al.

FOREIGN PATENT DOCUMENTS

| WO | WO 97/49816 | | 12/1997 |
|---|---|---|---|
| WO | WO 0032757 A2 | * | 6/2000 |
| WO | WO 0220741 A1 | * | 3/2002 |
| WO | WO 02/46387 A2 | | 6/2002 |
| WO | WO 2009/144079 A1 | | 12/2009 |
| WO | WO 2010/085705 A2 | | 7/2010 |

OTHER PUBLICATIONS

Lee et al. (Plant Physiology, (2006), vol. 140: pp. 466-483).*
Chotewutmontri et al. (The Plant Cell, (2012) vol. 24: 3040-3059).*
Ferullo et al. (WO 02/20741 A1, (2002), originally printed in French, English translation provided).*
Fritze et al. (Plant Physiology, (2004), vol. 134, pp. 1388-1400).*
Emanuelsson et al. (Journal of Mol. Bioi., (2000), vol. 300, pp. 1005-1016).*
WO 0220741 A1 english translation.*
Emanuelsson, O., et al., "Predicting Subcellular Localization of Proteins Based on Their N-terminal Amino Acid Sequence," *J.Mol. Biol.*, 2000, pp. 1005-1016, vol. 300, Academic Press, USA.
Fritze, I., et al., "The Crystal Structures of Zea mays and Arabidopsis 4-Hydroxyphenylpyruvate Dioxygenase," *Plant Physiology*, Apr. 2004, pp. 1388-1400, vol. 134, American Society of Plant Biologists, USA.
Garcia, I., et al., "Subcellular localization and purification of a p-hydroxyphenylpyruvate dioxygenase from cultured carrot cells and characterization of the corresponding cDNA," *Biochem. J.*, 1997, pp. 761-769, vol. 325, Great Britain.
Garcia, I., et al., "Characterization and Subcellular Compartmentation of Recombinant 4-Hydroxyphenylpyruvate Dioxygenase from Arabidopsis in Transgenic Tobacco," *Plant Physiology*, Apr. 1999, pp. 1507-1516, vol. 119, American Society of Plant Physiologists, USA.
Hoglund, A., et al., "MultiLoc: prediction of protein subcellular localization using N-terminal targeting sequences, sequence motifs and amino acid composition," *Bioinformatics*, 2006, pp. 1158-1165, vol. 22(10), Oxford University Press.
Yang, C., et al., "Structural Basis for Herbicidal Inhibitor Selectivity Revealed by Comparison of Crystal Structures of Plant and Mammalian 4-Hydroxyphenylpyruvate Dioxygenases," *Biochemistry*, 2004, pp. 10414-10423, vol. 43, American Chemical Society, USA.
U.S. Appl. No. 13/209,017, filed Aug. 12, 2011, Albert, et al.
U.S. Appl. No. 13/208,966, filed Aug. 12, 2011, Albert, et al.
Castle, L., et al, "Discovery and Directed Evolution of a Glyphosate Tolerance Gene," *Science*, 2004, vol. 304(5674), pp. 1151-1154.
Database EMBL—Accession No. AF251071, "Oryza sativa seed protein B32E mRNA, partial cds," 2002, pp. 1-2.

(Continued)

*Primary Examiner* — David T Fox
*Assistant Examiner* — Jared Shapiro
(74) *Attorney, Agent, or Firm* — Ballard Spahr LLP

(57) ABSTRACT

Chimeric polynucleotides comprising a nucleotide sequence encoding a chloroplast transit peptide operably linked to a heterologous polynucleotide of interest are provided, wherein the chloroplast transit peptide comprises an amino acid sequence having the chloroplast transit peptide sequence as set forth in SEQ ID NO:1 or a biologically active variant or fragment thereof or wherein the chloroplast transit peptide comprises the sequence set forth in SEQ ID NO: 58 or an active variant or fragment thereof. Chimeric polypeptides encoding the same, as well as, cells, plant cells, plants and seeds are further provided which comprise the chimeric polynucleotides. Compositions further include HPPD polypeptides and polynucleotides encoding the same as set forth in SEQ ID NOS: 57 and 60 or active variants and fragments thereof. Such sequences comprise the chloroplast transit peptide as set forth in SEQ ID NO: 58 or an active variants or fragments thereof. Cells, plant cells, plants and seeds are further provided which comprise such sequences. Methods of use of the various sequences are also provided.

38 Claims, 16 Drawing Sheets

(56) References Cited

OTHER PUBLICATIONS

Fiedler, E., et al., "The formation of homogentisate in the biosynthesis to tocopherol and plastoquinone in spinach chloroplasts," *Planta*, 1982, vol. 155, pp. 511-515.

Lee, R., et al., "Leaf senescence in rice plants: cloning and characterization of senescence up-regulated genes," *Journal of Experimental Botany*, 2001, vol. 52(358), pp. 1117-1121.

* cited by examiner

Figure 1

|  |  | 1 | 50 |
|---|---|---|---|
| Avena sativa HPPD WO0246387 | (1) | MPPTPATATGA---AAAAVTPEHAAR---SFPRVVRVNPRSDRFPVLSFH | |
| Hordeum vulgare HPPD O48604.1 | (1) | MPPTPTTPAAT--GAAAAVTPEHARP-----HRMVRFNPRSDRFHTLSFH | |
| Oryza sativa HPPD BAD26248.1 | (1) | MPPTPTPTATTGAVSAAAAAGENAGFRLVGHRRFVRANPRSDRFQALAFH | |
| Sorghum bicolor HPPD XP_002453359 | (1) | MPPTPTTAAATGAAVAAASA-EQAAFRLVGHRNFVRVNPRSDRFHTLAFH | |
| Triticum aestivum HPPD AAZ67144.1 | (1) | MPPTPTTPAATGAGAAAAVTPEHARP-----RRMVRFNPRSDRFHTLSFH | |
| Zea mays WO1997049816Seq#11 | (1) | MPPTPTAAAAGAAVAAASAA-EQAAFRLVGHRNFVRFNPRSDRFHTLAFH | |

|  |  | 51 | 100 |
|---|---|---|---|
| Avena sativa HPPD WO0246387 | (45) | HVELWCADAASAAGRFSFALGAPLAARSDLSTGNSAHASLLLRSGALAFL | |
| Hordeum vulgare HPPD O48604.1 | (44) | HVEFWCADAASAAGRFAFALGAPLAARSDLSTGNSAHASQLLRSGSLAFL | |
| Oryza sativa HPPD BAD26248.1 | (51) | HVELWCADAASAAGRFAFALGAPLAARSDLSTGNSAHASLLLRSASVAFL | |
| Sorghum bicolor HPPD XP_002453359 | (50) | HVELWCADAASAAGRFSFGLGAPLAARSDLSTGNTAHASLLLRSGALAFL | |
| Triticum aestivum HPPD AAZ67144.1 | (46) | HVEFWCADAASAAGRFAFALGAPLAARSDLSTGNSVHASQLLRSGNLAFL | |
| Zea mays WO1997049816Seq#11 | (50) | HVELWCADAASAAGRFSFGLGAPLAARSDLSTGNSAHASLLLRSGSLSFL | |

|  |  | 101 | 150 |
|---|---|---|---|
| Avena sativa HPPD WO0246387 | (95) | FTAPYAPPPQEAATAAATASIPSFSADAARTFAAAHGLAVRSVGVRVADA | |
| Hordeum vulgare HPPD O48604.1 | (94) | FTAPY-----ANGCDAATASLPSFSADAARRFSADHGIAVRSVALRVADA | |
| Oryza sativa HPPD BAD26248.1 | (101) | FTAPYGGDHGVGADAATTASIPSFSPGAARRFAADHGLAVHAVALRVADA | |
| Sorghum bicolor HPPD XP_002453359 | (100) | FTAPY-----AHGADAATASLPSFSAADARRFAADHGLAVRAVALRVADA | |
| Triticum aestivum HPPD AAZ67144.1 | (96) | FTAPY-----ANGCDAATASLPSFSADAARRFSADHGLAVRSIALRVADA | |
| Zea mays WO1997049816Seq#11 | (100) | FTAPY-----AHGADAATAALPSFSAAAARRFAADHGLAVRAVALRVADA | |

|  |  | 151 | 200 |
|---|---|---|---|
| Avena sativa HPPD WO0246387 | (145) | AEAFRVSVAGGARPAFAPADLGHGFGLAEVELYGDVVLRFVSYPDETDLP | |
| Hordeum vulgare HPPD O48604.1 | (139) | AEAFRASRRRGARPAFAPVDLGRGFAFAEVELYGDVVLRFVSHPDGTDVP | |
| Oryza sativa HPPD BAD26248.1 | (151) | ADAFRASVAAGARPAFQPADLGGGFGLAEVELYGDVVLRFVSHPDGADAP | |
| Sorghum bicolor HPPD XP_002453359 | (145) | EDAFRASVAAGARPAFEPVELGLGFRLAEVELYGDVVLRYVSYPDDADAS | |
| Triticum aestivum HPPD AAZ67144.1 | (141) | AEAFRASVDGARPAFSPVDLGRGFGFAEVELYGDVVLRFVSHPDDTDVP | |
| Zea mays WO1997049816Seq#11 | (145) | EDAFRASVAAGARPAFGPVDLGRGFRLAEVELYGDVVLRYVSYPDGAAGE | |

|  |  | 201 | 250 |
|---|---|---|---|
| Avena sativa HPPD WO0246387 | (195) | -FLPGFERVSSPGAVDYGLTRFDHVVGNVPEMAPVIDYMKGFLGFHEFAE | |
| Hordeum vulgare HPPD O48604.1 | (189) | -FLPGFEGVTNPDAVDYGLTRFDHVVGNVPELAPAAAYIAGFTGFHEFAE | |
| Oryza sativa HPPD BAD26248.1 | (201) | -FLPGFEGVSNPGAVDYGLRRFDHVVGNVPELAPVAAYISGFTGFHEFAE | |
| Sorghum bicolor HPPD XP_002453359 | (195) | -FLPGFVGVTSPGAADYGLRRFDHIVGNVPELAPAAAYFAGFTGFHEFAE | |
| Triticum aestivum HPPD AAZ67144.1 | (191) | -FLPGFEGVSNPDAVDYGLTRFDHVVGNVPELAPAAAYVAGFAGFHEFAE | |
| Zea mays WO1997049816Seq#11 | (195) | PFLPGFEGVASPGAADYGLSRFDHIVGNVPELAPAAAYFAGFTGFHEFAE | |

|  |  | 251 | 300 |
|---|---|---|---|
| Avena sativa HPPD WO0246387 | (244) | FTAEDVGTTESGLNSVVLANNSEAVLLPLNEPVHGTKRRSQIQTYLEYHG | |
| Hordeum vulgare HPPD O48604.1 | (238) | FTAEDVGTTESGLNSVVLANNSEGVLLPLNEPVHGTKRRSQIQTFLEHHG | |
| Oryza sativa HPPD BAD26248.1 | (250) | FTAEDVGTAESGLNSVVLANNAETVLLPLNEPVHGTKRRSQIQTYLDHHG | |
| Sorghum bicolor HPPD XP_002453359 | (244) | FTAEDVGTTESGLNSMVLANNAENVLLPLNEPVHGTKRRSQIQTYLDHHG | |
| Triticum aestivum HPPD AAZ67144.1 | (240) | FTTEDVGTAESGLNSMVLANNSEGVLLPLNEPVHGTKRRSQIQTFLEHHG | |
| Zea mays WO1997049816Seq#11 | (245) | FTTEDVGTAESGLNSMVLANNSENVLLPLNEPVHGTKRRSQIQTFLDHHG | |

|  |  | 301 | 350 |
|---|---|---|---|
| Avena sativa HPPD WO0246387 | (294) | GPGVQHIALASNDVLRTLREMRARTPMGGFEFMAPPQAKYYEGVRRIAGD | |
| Hordeum vulgare HPPD O48604.1 | (288) | GPGVQHIAVASSDVLRTLRKMRARSAMGGFDFLPPPLPKYYEGVRRLAGD | |
| Oryza sativa HPPD BAD26248.1 | (300) | GPGVQHIALASDDVLGTLREMRARSAMGGFEFLAPPPPNYYDGVRRRAGD | |
| Sorghum bicolor HPPD XP_002453359 | (294) | GPGVQHMALASDDVLRTLREMRARSAMGGFEFMAPPAPEYYDGVRRAGD | |
| Triticum aestivum HPPD AAZ67144.1 | (290) | GSGVQHIAVASSDVLRTLREMRARSAMGGFDFLPPRCRKYYEGVRRIAGD | |
| Zea mays WO1997049816Seq#11 | (295) | GPGVQHMALASDDVLRTLREMQARSAMGGFEFMAPPTSDYYDGVRRRAGD | |

|  |  | 351 | 400 |
|---|---|---|---|
| Avena sativa HPPD WO0246387 | (344) | VLSEEQIKECQELGVLVDRDDQGVLLQIFTKPVGDRPTFFLEMIQRIGCM | |
| Hordeum vulgare HPPD O48604.1 | (338) | VLSEAQIKECQELGVLVDRDDQGVLLQIFTKPVGDRPTLFLEMIQRIGCM | |
| Oryza sativa HPPD BAD26248.1 | (350) | VLSEEQINECQELGVLVDRDDQGVLLQIFTKPVGDRPTFFLEMIQRIGCM | |
| Sorghum bicolor HPPD XP_002453359 | (344) | VLTEAQIKECQELGVLVDRDDQGVLLQIFTKPVGDRPTLFLEIIQRIGCM | |
| Triticum aestivum HPPD AAZ67144.1 | (340) | VLSEAQIKECQELGVLVDRDDQGVLLQIFTKPVGDRPTLFLEMIQRIGCM | |
| Zea mays WO1997049816Seq#11 | (345) | VLTEAQIKECQELGVLVDRDDQGVLLQIFTKPVGDRPTLFLEIIQRIGCM | |

|  |  | 401 | 450 |
|---|---|---|---|
| Avena sativa HPPD WO0246387 | (394) | EKDEVGQEYQKGGCGGFGKGNFSELFKSIEDYEKSLEVKQSVVAQKS--- | |
| Hordeum vulgare HPPD O48604.1 | (388) | EKDERGEEYQKGGCGGFGKGNFSELFKSIEDYEKSLEAKQSAAVQGS--- | |
| Oryza sativa HPPD BAD26248.1 | (400) | EKDESGQEYQKGGCGGFGKGNFSELFKSIEEYEKSLEAKQAPTVQGS--- | |
| Sorghum bicolor HPPD XP_002453359 | (394) | EKDEKGQEYQKGGCGGFGKGNFSQLFKSIEDYEKSLEAKQAAAAQGS--- | |
| Triticum aestivum HPPD AAZ67144.1 | (390) | EKDERGEEYQKGGCGGFGKGNFSELFKSIEDYEKSLEAKQSAAVQGS--- | |
| Zea mays WO1997049816Seq#11 | (395) | EKDEKGQEYQKGGCGGFGKGNFSQLFKSIEDYEKSLEAKQAAAAAAQGS | |

Figure 2A

```
                                                1                                                          60
Zea mays WO1997049816Seq#11          (1)  ------------------------------MPPTPTAAAAGAAVAAASAAEQAAFRLVGHRNF
Daucus carota HC198620               (1)  ------------------------------MGKKQSEAEILSSNSSNTSPATFKLVGFNNF
S. scutellarioides Q9ARF9            (1)  ------------------------------MGQESTAAAAVVPAEFKLVGHKNF
Picea sitchensis EF087545            (1)  ------------------------------------------------------------
Abutilon theophrasti AAN28922        (1)  ------------------------------------------------------------
Arabidopsis thaliana AAM96960        (1)  MCLSLASTAQRNTKFRSRVLVLAELVKSMGHQNAAVSENQNHDDGAASSPGFKLVGFSKF
Brassica rapa HPPD ABI63586          (1)  ------------------------MGHENAAVSENQHHDDAATTSASPGFKLVGFSKF
Coptis japonica BAF74636             (1)  -------------------------------------MVPSTASNLKLVGHTNF
Vitis vinifera CAN71143              (1)  ------------------------------MGKQNTTTNNPAPGFKLVGFSNF
Glycine max US7071381 Seq#36         (1)  ---------------------MPIPMCNEIQAQAQAQAQAQPGFKLVGFKNF
Medicago truncatula AAX59006         (1)  ---------------------------MAIETETQTQTQTGFKLVGFKNF 61                                                        120
Zea mays WO1997049816Seq#11          (34) VRFNPRSDRFHTLAFHHVELWCADAASAAGRFSFGLGAPLAARSDLSTGNSAHASLLLRS
Daucus carota HC198620               (32) VRANPKSDHFAVKRFHHIEFWCGDATNTSRRFSWGLGMPLVAKSDLSTGNSVHASYLVRS
S. scutellarioides Q9ARF9            (25) VRSNPMSDHFPVHRFHHVEFWCGDATNTSRRFSWGLGMPLVAKSDLSTGNSAHASYLLRS
Picea sitchensis EF087545            (1)  ------------------------------------------------------------
Abutilon theophrasti AAN28922        (1)  ------------------CTDATNAACRFSWGLGMQFVAKSDLSTGNLSHASYLLRS
Arabidopsis thaliana AAM96960        (61) VRKNPKSDKFKVKRFHHIEFWCGDATNVARRFSWGLGMRFSAKSDLSTGNMVHASYLLTS
Brassica rapa HPPD ABI63586          (35) VRKNPKSDKFKVKRFHHIEFWCGDAVNVARRFSWGLGMRFSAKSDLSTGNMVHASYLLTS
Coptis japonica BAF74636             (18) VHNNPKSDKFHVKKFHHIEFWSTDATNTARRFSWGLGMPMVAKSDLSTGNMVHASYLLRS
Vitis vinifera CAN71143              (24) LRTNPMSDRFGVKRFHHIEFWSTDATNLARRFSWGLGMPIVAKSDLSTGNVIHASYLTRS
Glycine max US7071381 Seq#36         (32) VRTNPKSDRFQVNRFHHIEFWCTDATNASRRFSWGLGMPIVAKSDLSTGNQIHASYLLRS
Medicago truncatula AAX59006         (24) VRANPKSDRFNVKRFHHVEFWCTDATNTARRFSHGLGMPIVAKSDLSTGNLTHASYLLRS 121                                                       180
Zea mays WO1997049816Seq#11          (94)  GSLSFLFTAPYAHGADAAT-------AALPSFSAAAARRFAADHGLAVRAVALRVADAED
Daucus carota HC198620               (92)  ANLSFVFTAPYSPSTTTSSGS-----AAIPSFSASGFHSFAAKHGLAVRAIALEVADVAA
S. scutellarioides Q9ARF9            (85)  GELSFVFTAPYSPSLAEPS-S-----ASIPTFSFSDHRAFTSSHGLAVRAVAIQVDSASS
Picea sitchensis EF087545            (1)   ------------------------------------------------------------
Abutilon theophrasti AAN28922        (40)  DHLSLLFTAPYSPSIALSQNISPHSTASTPSFDHTLCRSFSSSHGLVVRAIALEVEDSET
Arabidopsis thaliana AAM96960        (121) GDLRFLFTAPYSPSLSAGEIKP-TTTASIPSFDHGSCRSFFSSHGLGVRAVAIEVEDAES
Brassica rapa HPPD ABI63586          (95)  GDLRFLFTAPYSPSLSAGENPP-TTTASIPSFDHVTYRSFFSSHGLGVRAVAVEVEDAEA
Coptis japonica BAF74636             (78)  GELNFLFTAPYSPSIAGNTLT---HTASIPTYSHNLARLFASTHGLAVRAIAIEVQDAEL
Vitis vinifera CAN71143              (84)  GDLNFLFTAPYSPSIAGDLEN-AAATASIPSFDHSACHAFAASHGLGVRAIAIEVDDAEG
Glycine max US7071381 Seq#36         (92)  GDLSFLFSAPYSPSLSAGSSAAS--SASIPSFDAATCLAFAAKHGFGVRAIALEVADAEA
Medicago truncatula AAX59006         (84)  GDLNFLFSAAYSPSISLSSPS---STAAIPTFSASTCFSFSASHGLAVRAVAVEVEDAEV 181                                                       240
Zea mays WO1997049816Seq#11          (147) AFRASVAAGARPAFGPVDLGRGF-RLAEVELYGDVVLRYVSYPDGAAGE-------PFLP
Daucus carota HC198620               (147) AFEASVARGARPASAPVELDDQA-WLAEVELYGDVVLRFVSFGREEG---------LFLP
S. scutellarioides Q9ARF9            (139) AYSAAVSRGAKPVSPPVVLADCETAIAEVHLYGDTVLRFVSCGSGADG--------WFLP
Picea sitchensis EF087545            (1)   -----------MSEVKLYGDVVLRFVSKDGFEG---------PFLP
Abutilon theophrasti AAN28922        (100) AFATSISNGALPSSPPILLDGAT--ISEVKLYGDVVLRYVSYSKNTN----P---HHFLP
Arabidopsis thaliana AAM96960        (180) AFSISVANGAIPSSPPIVLNEAV-TIAEVKLYGDVVLRYVSYKAEDTEKS------EFLP
Brassica rapa HPPD ABI63586          (154) AFSISVSNGAVPSSPPIVLNDA-TIAEVKLYGDVVLRYVSYKVATV----------FLP
Coptis japonica BAF74636             (135) AYNISVANGAKESSSPIKLDEGV-VLSEIQLYGDVVLRYLSFKNTNQS-------CPFLP
Vitis vinifera CAN71143              (143) AFHTSVAHGARPMSPPVTMGGSV-VISEVHLYGDAVLRYVSYKNPNPNATSDP-SSWFLP
Glycine max US7071381 Seq#36         (150) AFSASVAKGAEPASPPVLVDDRT-GFAEVRLYGDVVLRYVSYKDAAPQAPHADPSRWFLP
Medicago truncatula AAX59006         (141) AFTTSVNLGAIPSSPPVILENNV-KLAEVHLYGDVVLRYVSYNDLNPNQNPN---LFFLP 241                                                       300
Zea mays WO1997049816Seq#11          (199) GFEGVASPGAAD---YGLSRFDHIVGNVPELAPAAAYFAGFTGFHEFAEFTTEDVGTAES
Daucus carota HC198620               (197) GFEAVEGTASFEDLDYGIRRLDHAVGNVTELGPVVEYIKGFTGFHEFAEFTAEDVGTLES
S. scutellarioides Q9ARF9            (191) GFEVVGDGVSCQELDYGIRRLDHAVGNVPKLEPVVDLKKFTGFHEFAEFTAEDVGTAES
Picea sitchensis EF087545            (27)  NYEPVQSIPLS----YGIIRVDHAVGNVEKLEEAVEYVAKFTGFHRFAEFTAEDVGTAES
Abutilon theophrasti AAN28922        (151) GFEKVEDNLSYP-LDYGIRRLDHAVCCVPELGPAISYVKSFTGFHDLAEFTAEDVGTSES
Arabidopsis thaliana AAM96960        (233) GFERVDASSFP-LDYGIRRLDHAVGNVPELGPALTYVAGFTGFHQFAEFTANDVGTAES
Brassica rapa HPPD ABI63586          (203) RFETVDDTSSFP-LDYGIRRLDHAVGNVPELGPALTYLSRLTGFHQFAEFTADDVGTAES
Coptis japonica BAF74636             (187) GFEEVGEVSSSRGLDFGIRRLDHAVGNVPNLAEAIGYLKEFTGFHEFAEFTAEDVGTTES
Vitis vinifera CAN71143              (201) GFEAVDEGSSFP-VDFGLRRVDHTVGNVEKLAPVVTYLKQFTGFHEFAEFTAEDVGTSES
Glycine max US7071381 Seq#36         (209) GFEAAASSSSFPELDYGIRRLDHAVGNVPELAPAVRYLKGFSGFHEFAEFTAEDVGTSES
Medicago truncatula AAX59006         (197) GFERVSDESSNSSLDFGIRRLDHAVGNVPELSSAVKYVKQFTGFHEFAEFTAEDVGTSES 301                                                       360
Zea mays WO1997049816Seq#11          (256) GLNSMVLANNSENVLLPLNEPVHGTKRRSQIQTFLDHHGGPGVQHMALASDDVLRTLREM
Daucus carota HC198620               (257) GLNSVVLANNEEMVLLPLNEPVYGTKRKSQIQTYLEHNEGAGVQHLALVSEDIFRTLREM
S. scutellarioides Q9ARF9            (251) GLNSVVLANNNENVLFPLNEPVYGTKRKSQIQTYLDHNEGAGVQHLALITEDIFRTLREM
Picea sitchensis EF087545            (83)  GLNSMVLASNNEMVLLPMNEPVFGTKRKSQIQTYLEHNEGPGLQHLALICSDIFSTLKEM
Abutilon theophrasti AAN28922        (210) GLNSVILANNNEMVLMPIAEPVYGTKRKSQVQTYLEHNEGAGVQHLALLSEDIFRTLREM
Arabidopsis thaliana AAM96960        (292) GLNSAVLASNDEMVLLPINEPVHGTKRKSQIQTYLEHNEGAGVQHLALMSEDIFRTLREM
Brassica rapa HPPD ABI63586          (262) GLNSAVLANNDETVLLPVNEPVHGTKRKSQIQTYLEHNEGAGVQHLALMSEDIFRTLREM
Coptis japonica BAF74636             (247) GLNSIVLANNNEMVLLPLNEPVYGTKRKSQIQTYLEHNEGAGVQHLALVSEDIFTTLREM
Vitis vinifera CAN71143              (260) GLNSVVLASNNEMVLLPLNEPVFGTKRKSQIQTYLEHNEGPGVQHLALMSDDIFRTLREM
Glycine max US7071381 Seq#36         (269) GLNSVVLANNSETVLLPLNEPVYGTKRKSQIETYLEHNEGAGVQHLALVTHDIFTTLREM
Medicago truncatula AAX59006         (257) GLNSVVLANNEETVLLPMNEPVYGTKRKSQIETYLEHNEGAGLQHLALMSADIFRTLREM
```

Figure 2B

```
                                              361                                                            420
    Zea mays WO1997049816Seq#11      (316) QARSAMGGFEFMAPPTSDYYDGVRRRAGDVLTEAQIKECQELGVLVDRDDQGVLLQIFTK
          Daucus carota HC198620     (317) RKRSCLGGFEFMPSPPPTYYKNLKNRVGDVLSDEQIKECEDLGTLVDRDDQGTLLQIFTK
         S. scutellarioides Q9ARF9   (311) RKRSEVGGFEFMPSPPPTYYRNLKSRAGDVLSDEQIEECEKLGILIDRDDQGTLLQIFTK
          Picea sitchensis EF087545  (143) RMRSDIGGFEFMPKPPPTYYKNLRNRVADILTEKQMEECDELGILVDRDDQGVLLQIFTK
       Abutilon theophrasti AAN28922 (270) RKRSFVGGFEFMPSPPPTYYEKLKQRVGDILSDEQIKECEELGIMVDRDDQGTLLQIFTK
       Arabidopsis thaliana AAM96960 (352) RKRSSIGGFDFMPSPPPTYYQNLKKRVGDVLSDDQIKECEELGILVDRDDQGTLLQIFTK
          Brassica rapa HPPD ABI63586 (322) RKRSGVGGFDFMPSPPPTYYKNLKNRVGDVLSEEQIEECEELGILVDRDDQGTLLQIFTK
          Coptis japonica BAF74636   (307) RRRSGVGGFEFMPSPPPTYKNLKNRAGDVLSDEQIKECEELGILVDRDAQGTLLQIFTK
          Vitis vinifera CAN71143    (320) RRRSGVGGFDFMPSPPPTYRNVKKRAGDVLTDDQIKECEELGILVDKDDQGTLLQIFTK
      Glycine max US7071381 Seq#36   (329) RKRSFLGGFEFMPSPPPTYYANLHNRAADVLTVDQIKQCEELGILVDRDDQGTLLQIFTK
       Medicago truncatula AAX59006  (317) RKRSGVGGFEFMPSPPVTYYRNLKNRVGDVLSDEQIKECEELGILVDRDDQGTLLQIFTK 421                                                            480
    Zea mays WO1997049816Seq#11      (376) PVGDRPTLFLEIIQRIGCMEKDEKGQEYQKGGCGGFGKGNFSQLFKSIEDYEKSLEAKQA
          Daucus carota HC198620     (377) PVGDRPTLFIEIIQRVGCMLKDDAGQMYQKGGCGGFGKGNFSELFKSIEEYEKTLEAKQI
         S. scutellarioides Q9ARF9   (371) PVGDRPTLFIEIIQRVGCMMKDEEGKMYQKGGCGGFGKGNFSELFKSIEEYEKMLESKLV
          Picea sitchensis EF087545  (203) PIGDRPTIFIEIIQRVGCLLTDENGQAYQKGGCGGFGKGNFSELFKSIEEYEKTLEGRVQ
       Abutilon theophrasti AAN28922 (330) PIGDRPTILLEIIQRIGCMVKDEEGKQYQKGGCG---------------------------
       Arabidopsis thaliana AAM96960 (412) PLGDRPTIFIEIIQRVGCMMKDEEGKAYQSGGCGGFGKGNFSELFKSIEEYEKTLEAKQL
          Brassica rapa HPPD ABI63586 (382) PLGDRPTIFIEIIQRIGCMKKDEEGKRVYQSGGCGGFGKGNFSELFKSIEEYEKTLEAKQL
          Coptis japonica BAF74636   (367) PVGDRPTIFVEIIQRLGCMLKDEEGKTYQKAGCGGFGKGNFSELFKSIEEYEKTLEAKAN
          Vitis vinifera CAN71143    (380) PLGDRPTFIEIIQRLGCMVKDDEGKVSQKGGCGGFGKGNFSELFKSIEEYEKTLGAKRI
      Glycine max US7071381 Seq#36   (389) PVGDRPTIFIEIIQRIGCMVEDEEGKVYQKGACGGFGKGNFSELFKSIEEYEKTLEAKRT
       Medicago truncatula AAX59006  (377) PIGDRPTIFIEIIQRVGCMLKDEEGKEYQKGGCGGFGKGNFSELFKSIEEYEKTLETRRT Zea mays WO1997049816Seq#11      (436) AAAAAAQGS
          Daucus carota HC198620     (437) TGSAAA---
         S. scutellarioides Q9ARF9   (431) TKTAMA---
          Picea sitchensis EF087545  (263) S--------
       Abutilon theophrasti AAN28922 (364) ---------
       Arabidopsis thaliana AAM96960 (472) VG-------
          Brassica rapa HPPD ABI63586 (442) VG-------
          Coptis japonica BAF74636   (427) VVAA-----
          Vitis vinifera CAN71143    (440) VDPAPV---
      Glycine max US7071381 Seq#36   (449) A--------
       Medicago truncatula AAX59006  (437) A--------
```

Figure 3

Figure 5
A.
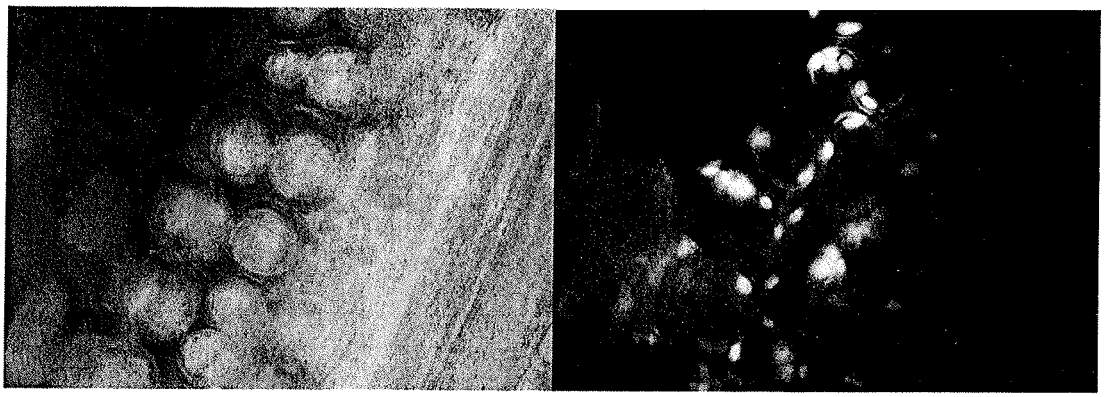
B.
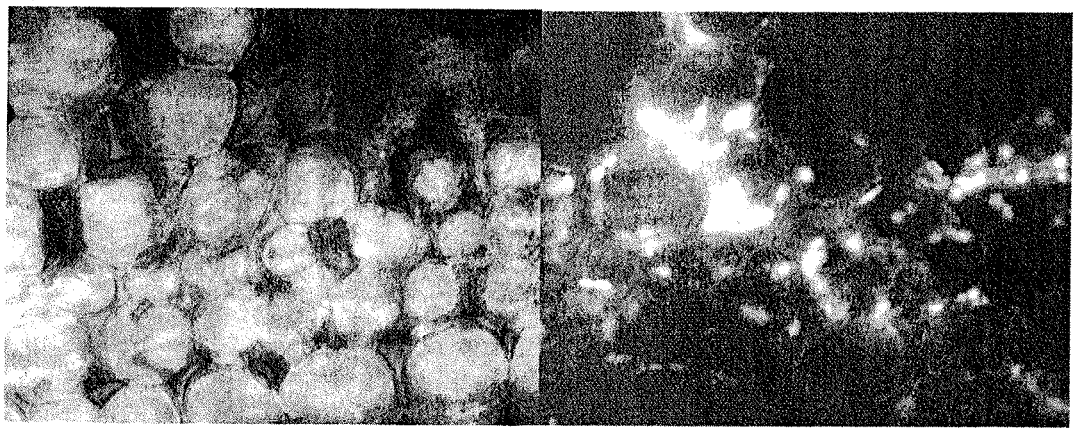
C.
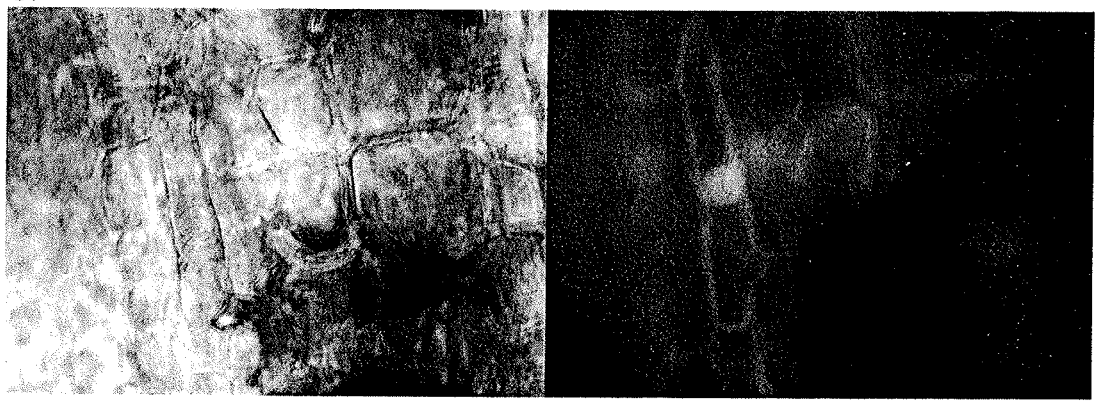

Figure 7A

```
Zea mays WO199704 9816Seq#11         (1) MPPTPTAAAAGAAV-AAASAAEQAAAFRLVGHRNFVFRNPRSDRFHTLAFHHVELWCADAASAAGRFSFGLGAPLA
Oryza sativa BAD26248.1              (1) MPPTPTPTATTGAVSAAAAAGENAGFRLVGHRRFVRANPRSDRFQALAFHHVELWCADAASAAGRFAFALGAPLA
Avena sativa WO0246387               (1) MPPTP-ATAT-GA--AAAAVTPEHAAR--SFPPRVRVNPRSDRFPVLSFHHVELWCADAASAAGRFSFALGAPLA
Hordeum vulgare O48604               (1) MPPTPTTPAATG---AAAAVTPEHA-RP--HR-MVRFNPRSDRFHTLSFHHVEFWCADAASAAGRFAFALGAPLA
Triticum aestivum DQ139267.1         (1) MPPTPTTPAATGAG-AAAAVTPEHA-RP--RRMVRFNPRSDRFHTLSFHHVEFWCADAASAAGRFAFALGAPLA
Acinetobacter sp 294841163           (1) -------------------------------------------------------------MDILENPLEL
Pseudomonas syringae NP_793333       (1) --------------------------------------------------------------MADLYEADKYENPMGL
Legionella pneumophila 60392610      (1) --------------------------------------------------------------MQNNNPCGL
Ralstonia solanacearum 299078043     (1) --------------------------------------------------------------MS
Bacillus thuringiensis YP_893139     (1) -------------------MVLSMNHLIYLQGDEDFMKQKSMDTLAAQMEDFFPVRDVDHLEFY
Chloroflexus aurantiacus YP_001634433 (1) ---------------------------MCSADPLELLGIDYVEFY
Catenulispora acidphila YP_003112250 (1) -----------------MTETATASAASATATKDPFPVKGMDAVVFA
Micromonospora aurantiaca ZP06217482 (1) -------------MTQAIDRPQSTEEVDVDALVGAVDHDITRDPFPVVKGMDHVHFLV
Salinispora tropica YP_011161056     (1) -------------MTQAILDRPQTSDEVDADLLVGAVDHDISHDPFPVVKGLDHVQFL
Geodermatophilus obscuresYP_003409000 (1) -------------MSLEQALNDDERLAQLDLDQLKQLVGLVEYDASGDPFPVSGWDALVWV
Kribbella flavida YP_003779684       (1) -------------MTSTDLTPAELDADLDLDQLKQLVPYDESTDPFPVTAMDAVVFV
Streptomyces avermitilis AAA50231    (1) -------------MTQTTHHTPDTARQADPFPVKGMDAVVFAVGN
Ostreococcus tauri HPPD CAL53021     (1) ------MTTSASGRKLVGHANFVRCNPLSDAFECVGFDHVEFWCGDATNAASRFGVGLGMSLR
Daucus carota 023920                 (1) ------MGKKQSEAEILSSNSSNTSPATFKLVGFNNFVRANPKSDHFAVKRFHHIEFWCGDATNTSRRFSWGL
Solenostemon scutellarioides Q9ARF9  (1) ------MGQESTAAAAVVPAEFKLVGHKNFVRSNPMSDHFPVHRFHHVEFWCGDATNTSRFSWG
Brassica rapa HPPD ABI63586          (1) MGHENAAVSFNQHHDDAATTSASPGFKLVGFSKFVKRNPKSDKFVKRFHHIEFWCGDATNVARRFSWGLGMRFS
Coptis japonica BAF74636             (1) -------MVPSTASNLKLVGHTNFVHNNPKSDKFHVKKFHHIEFWSTDATNTARRFSWGLGMPMV
Glycine max US7071381 Seq#36         (1) ---MPIPMCNEIQAQAQAQAQAQPGFKLVGFKNFVRTNPKSDRFQVNRFHHIEFWCTDATNASRFSWGLGMPIV
Vitis vinifera CAN71143              (1) ------MGKQ-NTTTNNPAPGFKLVGFSNFLRTNPMSDRFGVKRFHHIEFWSTDATNLARRFSWGLGMPIV
Medicago truncatula HPPD AAX59006    (1) ------MAIETETQTQTGFKLVGFKNFVRANPKSDRFNVKRFHHVEFWCTDATNTARRFSHGLGMPIV
Homo sapiens 417144                  (1) ------MTTYSDKGAKPERGRFLHFHSVTFWV
Rattus norvegicus P32755             (1) ------MTTYSDKGPKPERGRFLHFHSVTFWV
Mus musculus 33859486                (1) ------MTTYNNKGPKPERGRFLHFHSVTFWV
Bos taurus 75057880                  (1) ------MTTYSDKGEKPERGRFLHFHSVTFWV
                                                                                                                150
Zea mays WO199704 9816Seq#11         (75) ARSDLSTGNSAHASLLLRSGSLSLFLTAPYA------HGADAATAALPSFSAAAARRFAADHGLAVRAVALRVA
Oryza sativa BAD26248.1              (76) ARSDLSTGNSAHASLLLRSASVAPLFTAPYCGDH-G-VGADAATTASIPSFSPGAARRFAADHGLAVHAVALRVA
Avena sativa WO0246387               (70) ARSDLSTGNSAHASLLLRSGALAFLFTAPYAPP-Q-EAATAAATASIPSFSADAARTFAAAHGLAVRSVGVRVA
Hordeum vulgare O48604               (69) ARSDLSTGNSAHASLLLRSGSLAFLFTAPYA------NGCDAATASLPSFSADAARRFSADHGIAVRSVALRVA
Triticum aestivum DQ139267.1         (71) ARSDLSTGNSVHASQLLRSGNLAFLFTAPYA------NGCDAATASLPSFSADAARRFSADHGLAVRSIALRVA
Acinetobacter sp 294841163           (11) CGFAFIEFVSKE-NELDPIFETIGFSKVAKHKSKKAYLMRQGNINILNYQPESYASFFFNEHGPSACAMGFKTR
Pseudomonas syringae NP_793333       (17) MGFEFIEFASPTPNSLEPVFQMMGFTKVATHRSKDVTLYRQGAINLILNNEPHSLASYFAAEHGPSVCGMAFRVK
Legionella pneumophila 60392610      (10) DGFAFLEFSGPDRNKLHQQFSEMGFQAVAHHKNQDITTLFKQGEIQFTVNAASHCQAEAHASTHGPGACAMGFKVK
Ralstonia solanacearum 299078043     (3)  AVTTAGFAFVFBFVCAEPNELVALFGKIGFKALGQHAQTGAVLLRQNEAVLIVNPAPNFRDVHGASARALAINVD
Bacillus thuringiensis YP_893139     (46) VGNAKQSSYYLARAFGFKIVAYSGLETGNREKVSYVLVQKNMRFVVSGALSSDNRIAEFVKITHGDGVDALLVD
Chloroflexus aurantiacus YP_001634433 (19) VSNARQAAHFYRTTLGLRPVAYAGLETGVRDRASYVLERRNVRFVLTAPLLPDHPIAQHIAHHGDGVKDIALRVR
Catenulispora acidphila YP_003112250 (31) VGNAKQAAHYYSTAFGMRVVAYSGPETGRADRVAYVLESGSSARFVTKGSVRPGTEIALHVAEHGDGVTDLAIAVP
Micromonospora aurantiaca ZP06217482 (45) GNAKQAAHYYSTAFGMTCVAYRGPEQGVRDHAQYVLTSGSSARFLTGSSARFVLTGAVRPDADGAEHVAK-HSDGVSDIALEVP
Salinispora tropica YP_011161056     (44) VGNAKQAAHYYSTAFGMTCVAYRGPEQGVRDHAQYVLTSGSSARFVLTGAVRPDAAGAEQVARHSDGVCDIALEVP
Geodermatophilus obscuresYP_003409000 (49) VGNATQAAHFHQSAFGMELVAYSGPETGNRDHLAYVLESGAARFVVRGAYDPASPLADHHRKHGDGIVDIALSVP
```

```
Zea mays WO199704 9816Seq#11      (202) GVASPGAA------D-----YGLSRFDHIVGNVPE--LAPAAAYFAGFTGFHEFAEFTTEDVGTAESGLNSMVLAN
Oryza sativa BAD26248.1            (207) GVSNPGAV------D-----YGLRRFDHVGNVPE--LAPVAAYISGFTGFHEFAEFTAEDVGTAESGLNSVVLAN
Avena sativa WO0246387             (201) RVSSPGAV------D-----YGLTRFDHVGNVPE--MAPVIDYMKGFLGFHEFAEFTAEDVGTTESGLNSVVLAN
Hordeum vulgare O48604             (195) GVTNPDAV------D-----YGLTRFDHVGNVPE--LAPAAAVIAGFTGFHEFAEFTGFHEFAEFTEDVGTAESGLNSVVLAN
Triticum aestivum DQ139267.1       (197) GVSNPDAV------D-----YGLTRFDHVGNVPE--LAPAAAYVAGFAGFHEFAEFTTEDVGTAESGLNSVVLAN
Acinetobacter sp 294841163         (137) FFDDAQRNPEG---------AGLKEIDHLTHNVYKGRMEYWANFYEKIFNFQEIRYF---DIKGEYTGLTSKALTA
Pseudomonas syringae NP_793333     (149) FIEGVDRIHPVG--------AGLKFIDHLTHNVYRGRMAYWANFYEKLFNFRELRYF---DIKGEYTGLTSKAMSA
Legionella pneumophila 60392610    (138) ITSPEPVVG-----------NGLTAIDHLTHNVYRGNMDKWASFYASIFNFQEIRFEN--IKGKMTGLVSRALGS
Ralstonia solanacearum 299078043   (134) PRQPVDVAN-----------AAIQAIDHTSNIVKPENLDHWADFYKDTFAFVQKOYL---DVKGRQTGMRARSMVS
Bacillus thuringiensis YP_893139   (181) KAEFDIFPE-----E-----SGLIAVDHVVGNVEK--MEEWVSYENVMGFKQMIHFDDDDISTEYSALMSKVMTN
Chloroflexus aurantiacus 023920    (154) PITTPLPVP-----E-----TGIAAIDHIVGNVELGAMNRWVNYRDVLGFSQLVHFDDHDISTEYSALMSKVMQN
Catenulispora acidphila YP_0031122 (166) ERAPLVEPN-----A-----RIFQAIDHCVGNVELGKMDEWVDFYRHVMGFTNMAEFIGDDIATDYSALMSKVVAD
Micromonospora aurantiaca ZP062174 (179) ARGPIVDRQPMIDAGLQPKRFQAVDHVVGNVELGRMDEWVFYKRVMGFSNMAEFIGDDIATDYSALMSKVVAN
Salinispora tropica YP_001161056   (179) ARRPIVDRQPMIDAGVQPKRFFQAIDHVVGNVELGRMDEWVEFYQRVMGFTNMAEFVGEDIATDYSALMSKVVAN
Geodermatophilus obscuresYP_003409 (184) ERRSSHVKRDG---------APKRLFQAVDHVVGNVELGAMDRWVEFYNRVMGFTNMAEFVGEDIATDYSALMSKVVAN
Kribbella flavida YP_003379684     (183) AATTAVTRPEG---------HPKRLFQAVDHVVGNVELGKMDEWVGFVNKVMGFVNMAEFIGDDIATEYSALMSKVVAN
Streptomyces avermitilis AAA50231  (168) AAAPIVEPP-----------AHRTFQAIDHCVGNVELGRMNEWVGFVNKVMGFTNMKEFVGDDIATEYSALMSKVVAD
Ostreococcus tauri HPPD CAL53021   (200) ATRDVPSVS-----------YGLRRLDHAVGNVTE--LLETVDYIMKITGFHEFAEFTAEDVGTIESGLNSVVLAN
Daucus carota 023920               (197) AVEGTASFPDL---D-----YGIRRLDHAVGNVTE--LGPVVEYIKGFTGFHEFAEFTAEDVGTIESGLNSVVLAN
Solenostemon scutellarioides Q9ARF9(194) VVGDGVSCQEL---D-----YGIRRLDHAVGNVPK--LEPVVDYLKKFTGFHEFAEFTAEDVGTAESGLNSVVLAN
Brassica rapa HPPD ABI63586        (206) TVDDTSSFP-L---D-----YGIRRLDHAVGNVPE--LGPALTYLSRLTGFHQFAEFTADDVGTAESGLNSVVLAN
Coptis japonica BAF74636           (190) EVGEVSSSRGL---D-----YGIRRLDHAVGNVPN--LAEAIGYLKEFTGFHEFAEFTAEDVGTSESGLNSVVLAS
Glycine max US7071381 Seq#36       (212) AAASSSSFPEL---D-----YGIRRLDHAVGNVPE--LAPAVRYLKGFSGFHEFAEFTAEDVGTSESGLNSVVLAN
Vitis vinifera CAN71143            (204) AVDEGSSSFP-V--D-----FGLRRVDHTVGNVPK--LAPVVTYLKQFTGFHEFAEFTAEDVGTSESGLNSVVLAS
Medicago truncatula HPPD AAX59006  (200) RVSDESSNSSL---D-----FGIRRLDHAVGNVPE--LSSAVKIYVKQFTGFHEFAEFTAEDVGTSESGLNSVVLAN
Homo sapiens 417144                (162) APAFMDPLLPKLPK------CSLEMIDHIVGNQPDQEMSASEWVLKNLQFHRFWSVDDTQVHTEYSSLRSIVVAN
Rattus norvegicus P32755           (162) APTYKDTLLPKLPS------CNLEIDHIVGNQPDQEMSASEWVLKNLQFHREWSVDDTQVHTEYSSLRSIVVAN
Mus musculus 33859486              (162) APTYKDTLLPKLPR------CNLEIIDHIVGNQPDQEMQSASEWVLKNLQFHREWSVDDTQVHTEYSSLRSIVVTN
Bos taurus 75057880                (162) APPFMDPQLSKLPS------CSLEIIDHIVGNQPDQEMVSASEWVLKNLQFHREWSVDDTQVHTEYSSLRSVVVAN
                                                                                                                375

301
Zea mays WO199704 9816Seq#11       (265) NSENVLLPLNEPVHGTK-RRSQIQTFLDHHGGPGVQHMALASDDVIRTLREMQARSAM-GGFEFMAPPTSDYDYG
Oryza sativa BAD26248.1            (270) NAETVLLPLNEPVHGTK-RRSQIQTYLDHHGGPGVQHIALASDDVIGTLREMRARSAM-GGFEFLAPPPNYDG
Avena sativa WO0246387             (264) NSEAVLLPLNEPVHGTK-RRSQIQTYLEYHGGPGVQHIALASNDVLRTLREMRARTPM-GGFEFMAPPQAKYEG
Hordeum vulgare O48604             (258) NSEGVLLPLNEPVHGTK-RRSQIQTFLEHHGGPGVQHIAVASSDVIRTLRKMRARSAM-GGFDFLPPPLPKYEG
Triticum aestivum DQ139267.1       (260) NSEGVLLPLNEPVHGTK-RRSQIQTFLEHHGGSGVQHIAVASSDVIRTLREMRARSAM-GGFDFLPPRCRKYEG
Acinetobacter sp 294841163         (201) PDGMIRIPLNEDSDK---GNGQIAEFIADFNGEGIQHIAFICEDLISTWDKLKGLGLK----FMTPPPNYYEM
Pseudomonas syringae NP_793333     (213) PDGMIRIPLNEESSK---GAGQIEEFIMQFNGEGIQHVAFFTDDLIKTWDALKATGMR----FMTAPPDTYYEM
Legionella pneumophila 60392610    (200) PDGKVSIPLNESKDD---LSQIEFLHEYHGEGIQHYHGEGIQHIALNTNDIYKTVNGLRKQGVK----FLDVPDTYYEM
Ralstonia solanacearum 299078043   (196) PCGKVSIPIAAAAHDQPGVLNQNDEFIRDYRGEGIQHIAFLSSNIEQTIAAMEKAGID----FMDTPPKIYYQN
Bacillus thuringiensis YP_893139   (245) GS--RIKFPINEPADG-K-RKSQIQEYLEFYGGPGVQHIALALATGDICATVDALRAAGIP----FIHVPDAYYDD
Chloroflexus aurantiacus 023920    (220) GTGRIKFPINEPAEG-R-RKSQIEEFLEFYGGPGVQHIALNTGDILALTVDAMRAAGVE----FLETPDSYYED
Catenulispora acidphila YP_0031122 (232) GTRKVKFPINEPAIA-K-KKSQIDEYLEFYQGGPGVQHIAVATNDILASVDAMRAAGVE----FLDTPDSYYED
Micromonospora aurantiaca ZP062174 (254) GTRKVKFPINEPAVA-R-KKSQIDEYLEFYQGPGAQHIAVATNDILASVDAMRAAGVD----FLDTPDSYYED
Salinispora tropica YP_001161056   (254) GTRKVKFPINEPAVA-K-KKSQIDEYLDFYQGPGAQHIAVATNDILASVDAMRAAGVD----FLDTPDSYYED
Geodermatophilus obscuresYP_003409 (254) GNHRVKFPINEPAIG-K-KKSQIDEYLEFYGGPGAQHVALAINDILTTVDALRAEGIE----FLATPDSYYED
```

```
Zea mays WO1997049816Seq#11           (406) GGCGGCGFGKGNFSQLFKSIEDYEKSLEAKQAAAAAAQGS---
Oryza sativa BAD26248.1               (411) GGCGGCGFGKGNFSELFKSIEEYEKSLEAKQAPTVQGS----
Avena sativa WO0246387                (405) GGCGGCGFGKGNFSELFKSIEDYEKSLEVKQSVVAQKS----
Hordeum vulgare O48604                (399) GGCGGCGFGKGNFSELFKSIEDYEKSLEAKQSAAVQGS----
Triticum aestivum DQ139267.1          (401) GGCGGCGFGKGNFSELFKSIEDYEKSLEAKQSAAVQGS----
Acinetobacter sp 294841163            (326) -----FGEGNFKALFESIERDQIRRGVLEAK-----------
Pseudomonas syringae NP_793333        (338) -----FGEGNFKALFESIERDQIQRGVLTPD-----------
Legionella pneumophila 60392610       (322) -----FGEGNFQALFEATERDQVRRGTLKELS----------
Ralstonia solanacearum 299078043      (321) -----FGEGNFKALFESQEQDQVRRGSLNAS-----------
Bacillus thuringiensis YP_893139      (366) G-FGEGNFKALFESIEREQERRGNL-----------------
Chloroflexus aurantiacus YP_001634433 (342) -G-FGKGNFKALFEAIEREAARRGNL----------------
Catenulispora acidphila YP_003112250  (356) -G-FGKGNFKALFEAIEREQERRGNL----------------
Micromonospora aurantiaca ZP06217482  (379) ---FGKGNFKALFEAIEREQEKRGNL----------------
Salinispora tropica YP_001161056      (379) ---FGKGNFKALFEAIEREQDKRGNL----------------
Geodermatophilus obscuresYP_003409000 (379) ---FGIGNFKALFEAIEREQHKRGNF----------------
Kribbella flavida YP_003379684        (378) ---FGKGNFKALFEAIEREQERRGNL----------------
Streptomyces avermitilis AAA50231     (358) ---FGKGNFKALFEAIEREQEKRGNL----------------
Ostreococcus tauri HPPD CAL53021      (406) AGCGGCGFGKGNFSELFKSIEBYEKTINI-------------
Daucus carota O23920                  (407) GGCGGCGFGKGNFSELFKSIEEYEKTLEAKQITGSAAA----
Solenostemon scutellarioides Q9ARF9   (401) GGCGGCGFGKGNFSELFKSIEEYEKMLESKLVTKTAMA----
Brassica rapa HPPD ABI63586           (412) GGCGGCGFGKGNFSELFKSIEEYEKTLEAKQLVG--------
Coptis japonica BAF74636              (397) AGCGGCGFGKGNFSELFKSIEEYEKTLEAKANVVAA------
Glycine max US7071381 Seq#36          (419) GACGGCGFGKGNFSELFKSIEEYEKTLEAKRTA---------
Vitis vinifera CAN71143               (410) GGCGGCGFGKGNFSELFKSIEEYEKTLGAKRIVDPAPV----
Medicago truncatula HPPD AAX59006     (407) GGCGGCGFGKGNFSELFKSIEEYEKTLETRRTA---------
Homo sapiens 417144                   (359) -----FGAGNFNSLFKAFEEEQNLRGNLTNMETNGVVPGM
Rattus norvegicus P32755              (359) -----FGAGNFNSLFKAFEEEQALRGNLTDLETNGVRSGM
Mus musculus 33859486                 (359) -----FGAGNFNSLFKAFEEEQALRGNLTDLEPNGVRSGM
Bos taurus 75057880                   (359) -----FGAGNFNSLFKAFEEEQDLRGNLTDMEPNGVVSG
```

METHODS AND COMPOSITIONS FOR TARGETING SEQUENCES OF INTEREST TO THE CHLOROPLAST

CROSS-REFERENCE TO RELATED APPLICATIONS

This application claims the benefit of U.S. Provisional Application Ser. No. 61/401,456, filed Aug. 13, 2010; U.S. Provisional Ser. No. 61/393,507, filed Oct. 15, 2010; and, U.S. Provisional Ser. No. 61/501,042, filed Jun. 24, 2011; each of which is herein incorporated by reference.

FIELD OF THE INVENTION

This invention is in the field of molecular biology. More specifically, this invention pertains to targeting sequences of interest to a chloroplast by employing a novel chloroplast transit peptide.

REFERENCE TO SEQUENCE LISTING SUBMITTED ELECTRONICALLY

The official copy of the sequence listing is submitted electronically via EFS-Web as an ASCII formatted sequence listing with a file named 408355seqlist.txt, created on Aug. 12, 2011, and having a size of 108 KB and is filed concurrently with the specification. The sequence listing contained in this ASCII formatted document is part of the specification and is herein incorporated by reference in its entirety

BACKGROUND OF THE INVENTION

Plastids are a heterogeneous family of organelles found ubiquitously in plants and algal cells. Most prominent are the chloroplasts, which carry out such essential processes as photosynthesis and the biosynthesis of fatty acids as well as of amino acids. Chloroplasts are complex organelles composed of six distinct suborganellar compartments: three different membranes (the two envelope membranes and the internal thylakoid membranes) and three compartments (the inner-membrane space of the envelope, the stroma and the thylakoid lumen.) More than 98% of all plastid proteins are translated on cytosolic ribosomes. Such proteins are posttranslationally targeted to and imported into the organelle. For a review, see, Jarvis et al. (2008) *New Phytologist* 179:257-285. Such translocation is mediated by multi-protein complexes in the outer and inner envelope membranes called TOC (Translocon at the Outer envelope membrane of Chloroplasts) and TIC (Translocon at the Inner envelope membrane of Chloroplasts). See, Soll et al. (2004) *Nature Reviews. Molecular Cell Biology* 5:198-208, Bedard et al. (2005) *Journal of Experimental Botany* 56:2287-2320, Kessler et al. (2006) *Traffic* 7:248-257, and Smith et al. (2006) *Canadian Journal of Botany* 84:531-542. Once the chloroplast precursor enters the stroma, the transit peptide if cleaved off, leaving the remaining part of the protein to take on its final confirmation or engage one of a number of different sorting pathways. See, Keegstra et al. (1999) *Plant Cell* 11:557-570, Jarvis et al. (2004) and Gutensohn et al. (2006) *Journal of Plant Physiology* 163:333-347.

Methods and compositions are needed to allow heterologous polypeptides to be targeted to the chloroplast.

BRIEF SUMMARY OF THE INVENTION

Chimeric polynucleotides comprising a nucleotide sequence encoding a chloroplast transit peptide operably linked to a heterologous polynucleotide of interest are provided, wherein the chloroplast transit peptide comprises an amino acid sequence having the consensus monocot HPPD chloroplast transit peptide sequence as set forth in SEQ ID NO:1 or a biologically active variant or fragment thereof or wherein the chloroplast transit peptide comprises the sequence as set forth in SEQ ID NO: 58 or a biologically active variant or fragment thereof. Chimeric polypeptides encoding the same, as well as, cells, plant cells, plants and seeds are further provided which comprise the chimeric polynucleotides. Methods of use of the various sequences are also provided.

Compositions further include novel HPPD polypeptides and polynucleotides encoding the same as set forth in SEQ ID NOS: 57 and 60 or active variants and fragments thereof. Such sequences comprise the chloroplast transit peptide as set forth in SEQ ID NO: 58 or an active variant or fragment thereof. Cells, plant cells, plants and seeds are further provided which comprise such sequences. Methods of use of the various sequences are also provided.

BRIEF DESCRIPTION OF THE DRAWINGS

FIG. 1 provides an amino acid alignment of HPPD from various monocot plants. HPPD from *Hordeum vulgare* is set forth in SEQ ID NO: 11. HPPD from *Avena sativa* is set forth in SEQ ID NO: 12. HPPD from *Oryza sativa* is set forth in SEQ ID NO:13. HPPD from *Triticum aestivum* is set forth in SEQ ID NO: 14. HPPD from *Zea mays* is set forth in SEQ ID NO: 10. HPPD from *Sorghum bicolor* is set forth in SEQ ID NO: 54. The underlining denotes amino acid residues sharing identity and the shading further displays the conserved amino acid residues.

FIG. 2 provides an amino acid alignment of HPPD polypeptides from various dicot plants compared to *Zea mays* SEQ ID NO: 10. HPPD from *Daucus carota* is set forth in SEQ ID NO: 15. HPPD from *Solenostemon scutellarioides* is set for in SEQ ID NO: 16. HPPD from *Picea sitchenis* is set for in SEQ ID NO: 17. HPPD from *Abutilon theophrasti* is set forth in SEQ ID NO: 18. HPPD from *Arabidopsis thaliana* is set forth in SEQ ID NO: 19. The HPPD from *Brassica rapa* is set forth in SEQ ID NO: 20. HPPD from *Coptis japonica* is set forth in SEQ ID NO: 21. HPPD from *Vitis vinifera* is set forth in SEQ ID NO: 22. HPPD from *Glycine max* is set forth in SEQ ID NO: 23. HPPD from *Medicago truncatula* is set forth in SEQ ID NO: 24.

FIG. 3 provides an alignment showing the diversity found in the N-terminal amino acids of HPPD polypeptides from moncot plants, dicot plants, microbes, a green alga and mammals.

FIG. 5A-C provides fluorescence microscopy of maize leaf tissue transfected with chloroplast-targeted or untargeted DsRed. FIG. 5A shows fluorescence observed in maize leaf transfected with ZmRCA1-Pro::RCA1CTP-Ds-Red2, 1000×. FIG. 5B shows fluorescence observed in maize leaf transfected with ZmRCA1-Pro::N-term-ZmHPPD-Ds-Red2, 1000×. FIG. 5C shows fluorescence observed in maize leaf transfected with untargeted Ds-Red2, 1000×. Photos on the left were of the same sample taken with white light.

FIG. 7A-E provides an alignment of additional HPPD sequences.

DETAILED DESCRIPTION OF THE INVENTION

Figure 4:
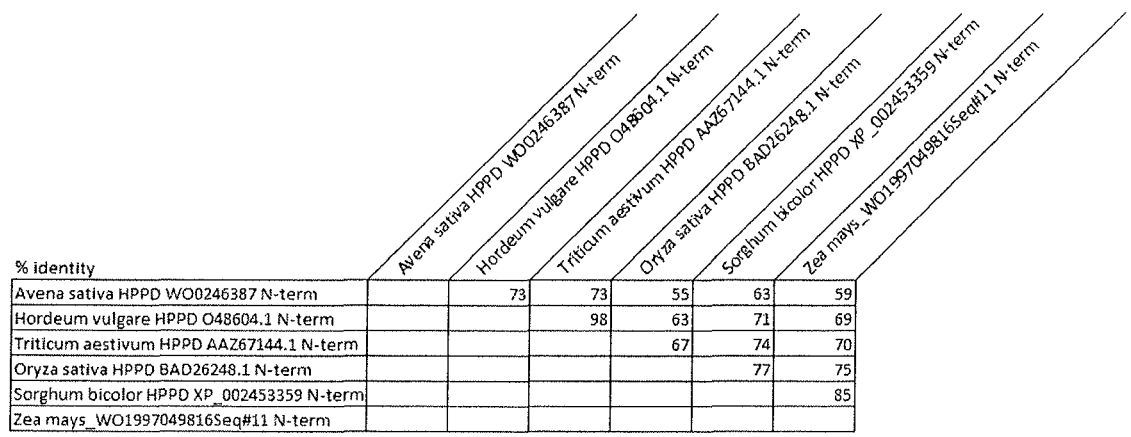
FIG. 4A provides an alignment of the N-terminal amino acids of the HPPD polypeptide from various monocot plants. Amino acids 1-52 of the *Zea mays* HPPD are set forth in SEQ ID NO:3; amino acids 1-52 of the *Sorghum bicolor* HPPD are set forth in SEQ ID NO:4; amino acids 1-52 of the *Oryza sativa* HPPD are set forth in SEQ ID NO: 5; amino acids 1-48 of the *Triticum aestivum* HPPD are set forth in SEQ ID NO: 6; amino acids 1-46 of the *Hordeum vulgare* HPPD are set forth in SEQ ID NO:7; amino acids 1-47 of the *Avena sativa* HPPD are set forth in SEQ ID NO: 8; and the consensus sequence is set forth in SEQ ID NO: 2.
FIG. 4B provides the % identity shared between the N-terminal regions of the HPPD polypeptides shown in FIG. 4A. The alignment was generated using AlignX which uses a modified Clustal W algorithm (program in Vector NTI (Invitrogen).)

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

I. Overview

In the production of transgenic plants it is often useful to direct foreign proteins to specific subcellular locations, e.g., the plastid, vacuole, mitochondria, or ER. When the gene is translated, the resulting protein has the transit peptide fused to the amino terminus of the protein of interest, and thus the protein is directed to the desired subcellular compartment. Of particular interest is the identification of transit peptides that will direct transport to a plastid. As used herein, a "plastid" refers to an organelle present in plant cells that stores and manufactures chemical compounds used by the cell, such as starch, fatty acids, terpenes, and that has been derived from a proplastid. Thus, plastids of plants typically have the same genetic content. Plastids include chloroplasts, which are responsible for photosynthesis, amyloplasts, chromoplasts, statoliths, leucoplasts, elaioplasts, and proteinoplasts. Plastids contain photosynthetic machinery and many additional biosynthetic enzymes including those leading to the production of fatty acids, amino acids, carotenoids, terpenoids, and starch. Thus, there is a need for the ability to target polypeptides of interest to plastids to modulate or alter the physiological processes that occur within these organelles. In addition, some polypeptides are toxic when expressed recombinantly in the cytoplasm. Because plastids are subcompartments, it is possible to target polypeptides of interest to the plastids to sequester them from the cytoplasm, and thus allow for higher expression levels. Furthermore, expression of recombinant polypeptides in plastids may facilitate isolation of the polypeptide for various applications. As discussed in further detail herein, novel CTP polypeptides from hydroxyphenylpyruvate dioxygenase polypeptides are provided which can be used in plastid targeting.

PSORT, a program that uses sequence data to predict organelle targeting, does not identify the N-terminal region of plant hydroxyphenylpyruvate dioxygenase (HPPD) proteins as a plastid targeting polypeptide. However, as demonstrated herein, HPPD polypeptides do contain a plastid targeting sequence which can be employed in a variety of methods and compositions to aid in targeting polypeptides of interest to the plastids. Thus, compositions and methods are provided for the targeting of polypeptides of interest to the chloroplast of a plant or plant cell.

The compositions provided herein include polynucleotides comprising a nucleotide sequence encoding a chloroplast transit peptide (CTP) derived from an HPPD polypeptide operably linked to a nucleotide sequence encoding a polypeptide of interest. The CTP-encoding sequences disclosed herein, when assembled within a DNA construct such that the CTP-encoding sequence is operably linked to a nucleotide sequence encoding the polypeptide of interest, facilitate co-translational or post-translational transport of the peptide of interest to the chloroplast of a plant cell.

II. Chloroplast Transit Peptides

Chloroplasts are organelles found in plant cells and eukaryotic algae that conduct photosynthesis. The chloroplast is a complex cellular organelle composed of three membranes: the inner envelope membrane, the outer envelope membrane, and the thylakoid membrane. The membranes together enclose three aqueous compartments termed the intermediate space, the stroma, and the thylakoid lumen. While chloroplasts contain their own circular genome, many constituent chloroplast proteins are encoded by the nuclear genes and are cytoplasmically-synthesized as precursor forms which contain N-terminal extensions known as chloroplast transit peptides (CTPs). As used herein, the term "chloroplast transit peptide" or "CTP" refers to the N-terminal portion of a chloroplast precursor protein and is instrumental for specific recognition of the chloroplast surface and in mediating the post-translational translocation of pre-proteins across the chloroplast envelope and into the various subcompartments within the chloroplast (e.g. stroma, thylakoid and thylakoid membrane). Thus, as used herein, a polypeptide having "CTP activity" comprises a polypeptide which when operably linked to the N-terminal region of a protein of interest facilitates translocation of the polypeptide of interest to the chloroplast.

In one embodiment, a CTP is provided comprising the following HPPD CTP consensus sequence.

(SEQ ID NO: 1)
MPPTP(T/A) (T/P/A) (T/P/A) (A/T) (G/T/A) (G/T/A) (G/A/*) (A/*)

(G/V/*) (A/S/V) AA(A/S) (A/S/V) (T/A) (P/G/*)E(HN/Q) A(A/G/R)

(F/P/R) (R/*)(L/*)(V/*)(G/S/*) (H/F/*)(R/H/P) (R/N)(F/M/V) VR(F/A/V)

NPRSDRF (H/Q/P)(T/A/V)L(A/S)FHHVE or an active variant or fragment thereof, where the * indicates that that amino acid position is not represented (ie. a gap in the alignment).

In further embodiments, a synthetic consensus HPPD sequence comprising a CTP is provided having the following sequence:

(SEQ ID NO: 2)
MPPTPTTAAATGAGAAAAVTPEHAAFRLVGHRRFVRFNPRSDRFH

TLAFHHVE or an active variant or fragment thereof.

In still other embodiments, a CTP is provided that comprises the N-terminal region of any HPPD polypeptide, including for example, the N-terminal region of a monocot HPPD polypeptide or a dicot HPPD. In one embodiment, the CTP can comprise amino acids 1-53, 1-17, 1-19, 1-20, 1-23, 1-30, 1-40 and 1-60 or a variant or fragment thereof of any monocot HPPD polypeptide. For example, the CTP can comprise any one of SEQ ID NO:3 (amino acids 1-52 of the *Zea mays* HPPD); SEQ ID NO: 4 (amino acids 1-52 of the *Sorghum bicolor* HPPD); SEQ ID NO: 5 (amino acids 1-52 of the *Oryza sativa* HPPD); SEQ ID NO: 6 (amino acids 1-48 of the *Triticum aestivum* HPPD); SEQ ID NO:7 (amino acids 1-46 of the *Hordeum vulgare* HPPD); SEQ ID NO:8 (amino acids 1-47 of the *Avena sativa* HPPD); or an active variant or fragment of any one of SEQ ID NOS: 2, 3, 4, 5, 6, 7 or 8. The CTP-encoding sequence can further comprise any N-terminal region (about amino acids 1-53, 1-17, 1-19, 1-20, 1-30, 1-40 and 1-60 or 1-23) of any of the HPPD polypeptides as set forth in FIG. 2 or 7 or an active variant or fragment of such polypeptides. In addition, the CTP can comprise the sequence of SEQ ID NO:58 (amino acids 1-86 of the Soybean HPPD) or an active variant or fragment thereof.

It is recognized that the various CTPs disclosed herein can be modified to improve and/or alter the translocation of the polypeptide of interest into the chloroplast. For example, the CTP can contain additional regions that alter or improve the interactions with cytosolic factors that facilitate the passage of precursors from the ribosomes to the chloroplast surface. See, for example, Hiltbrunner et al. (2001) *Journal of Cell Biology* 154:309-316, Jackson-Constan et al. (2001) *Biochimica et Biophysica Acta* 1541:102-113, both of which are herein incorporated by reference. Other regions can be employed to increase the efficiency of chloroplast import. See, for example, May et al. (2000) *Plant Cell* 12:53-64, Qbadou et al. (2006) *EMBO Journal* 25:1837-1837 and Sohrt et al. (2000) *Journal of Cell Biology* 148:1213-1221, herein incorporated by reference. Such regions may be native (derived from a region of the HPPD polypeptide) or heterologous to the operably linked HPPD CTP.

The various CTP disclosed herein can further comprise additional sequences which modulate the final location of the polypeptide of interest in the chloroplast. For example, the various CTPs disclosed herein could further comprise a thylakoid lumen targeting domain. Proteins to be targeted to the thylakoid lumen bear an additional cleavable targeting signal, which like the transit peptide, is removed once translocation is complete. The luminal targeting peptides are extremely similar to the signal peptides that mediate inner membrane transport in bacteria. See, for example, Keegstra et al. (1999) *Plant Cell* 11:557-570, Jarvis (2004) *Current Biology* 14: R1064-R1077, Gutensohn et al. (2006) Journal of Plant Physiology 163:333-347, and Jarvis (2008) *New Phytologist* 179:257-285, all of which are incorporated by reference in their entirety, which discuss the various sorting pathways in a chloroplast. Such regions which modulate the location of the polypeptide of interest in a chloroplast may be native (derived from a region of the HPPD polypeptide) or heterologous to the operably linked HPPD CTP.

The term "chloroplast transit peptide cleavage site" refers to a site between two amino acids in a chloroplast-targeting sequence at which the chloroplast processing protease acts. CTPs target the desired protein to the chloroplast and can facilitate the protein's translocation into the organelle. This is accompanied by the cleavage of the transit peptide from the mature polypeptide or protein at the appropriate transit peptide cleavage site by a chloroplast processing protease. Accordingly, a CTP further comprises a suitable cleavage site for the correct processing of the pre-protein to the mature polypeptide contained within the chloroplast. In one non-limiting example, the CTP cleavage site is after amino acid 23, between Q and A, in SEQ ID NO:1 which would equate to the H/N/Q-A in SEQ ID NO: 1. As discussed above, the sequences beyond the cleaved fragments may be important for localization/transport efficiency and be employed with any of the CTPs disclosed herein.

The term "chimeric" sequence refers to a sequence having two or more heterologous sequences linked together. As used herein, a "heterologous" CTP comprises a transit peptide sequence which is foreign to the polypeptide of interest it is operably linked to. In one embodiment, the heterologous chloroplast transit peptide comprises any one of SEQ ID NO: 1, 2, 3, 4, 5, 6, 7, 8, or 58 or an active variant or fragment thereof.

Assays to determine the efficiency by which the CTP sequences of the invention target a protein of interest to a chloroplast are known. See, for example, Mishkind et al. (1985) *J of Cell Biol* 100:226-234, which is herein incorporated by reference in its entirety. A reporter gene such as glucuronidase (GUS), chloramphenicol acetyl transferase (CAT), or green fluorescent protein (GFP) is operably linked to the CTP sequence. This fusion is placed behind the control of a suitable promoter, ligated into a transformation vector, and transformed into a plant or plant cell. Following an adequate period of time for expression and localization into the chloroplast, the chloroplast fraction is extracted and reporter activity assayed. The ability of the isolated sequences to target and deliver the reporter protein to the chloroplast can be compared to other known CTP sequences. See, de Castro Silva Filho et al. (1996) *Plant Mol. Biol.* 30: 769-780. Protein import can also be verified in vitro through the addition of proteases to the isolated chloroplast fraction. Proteins which were successfully imported into the chloroplast are resistant to the externally added proteases whereas proteins that remain in the cytosol are susceptible to digestion. Protein import can also be verified by the presence of functional protein in the chloroplast using standard molecular techniques for detection, by evaluating the phenotype resulting from expression of a chloroplast targeted protein, or by microscopy.

As used herein, an "isolated" or "purified" polynucleotide or polypeptide, or biologically active portion thereof, is substantially or essentially free from components that normally accompany or interact with the polynucleotide or polypeptide as found in its naturally occurring environment. Thus, an isolated or purified polynucleotide or polypeptide is substantially free of other cellular material or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A polypeptide that is substantially free of cellular material includes preparations of polypeptides having less than about 30%, 20%, 10%, 5%, or 1% (by dry weight) of contaminating protein. When the polypeptide of the invention or biologically active portion thereof is recombinantly produced, optimally culture medium represents less than about 30%, 20%, 10%, 5%, or 1% (by dry weight) of chemical precursors or non-protein-of-interest chemicals.

As used herein, polynucleotide or polypeptide is "recombinant" when it is artificial or engineered, or derived from an artificial or engineered protein or nucleic acid. For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A polypeptide expressed in vitro or in vivo from a recombinant polynucleotide is an example of a recombinant polypeptide. Likewise, a polynucleotide sequence that does not appear in nature, for example, a variant of a naturally occurring gene is recombinant.

a. Polynucleotide and Polypeptide Fragments and Variants of CTPs

Fragments and variants of the CTP-sequences are also encompassed by the present invention. By "fragment" is intended a portion of the polynucleotide or a portion of the amino acid sequence and hence protein encoded thereby. Fragments of a polynucleotide may encode protein fragments that retain CTP activity and are thus capable of facilitating the translocation of a polypeptide of interest into the chloroplast of a plant. Alternatively, fragments of a polynucleotide that is useful as a hybridization probe generally do not encode fragment proteins retaining biological activity. Thus, fragments of a nucleotide sequence may range from at least about 10, 20, 30, 40, 50, 60, 70, 80, 90, 100, 110, 120, 130, 140, 150, 160, 170 nucleotides or up to the full length CTP.

Figure 7D:
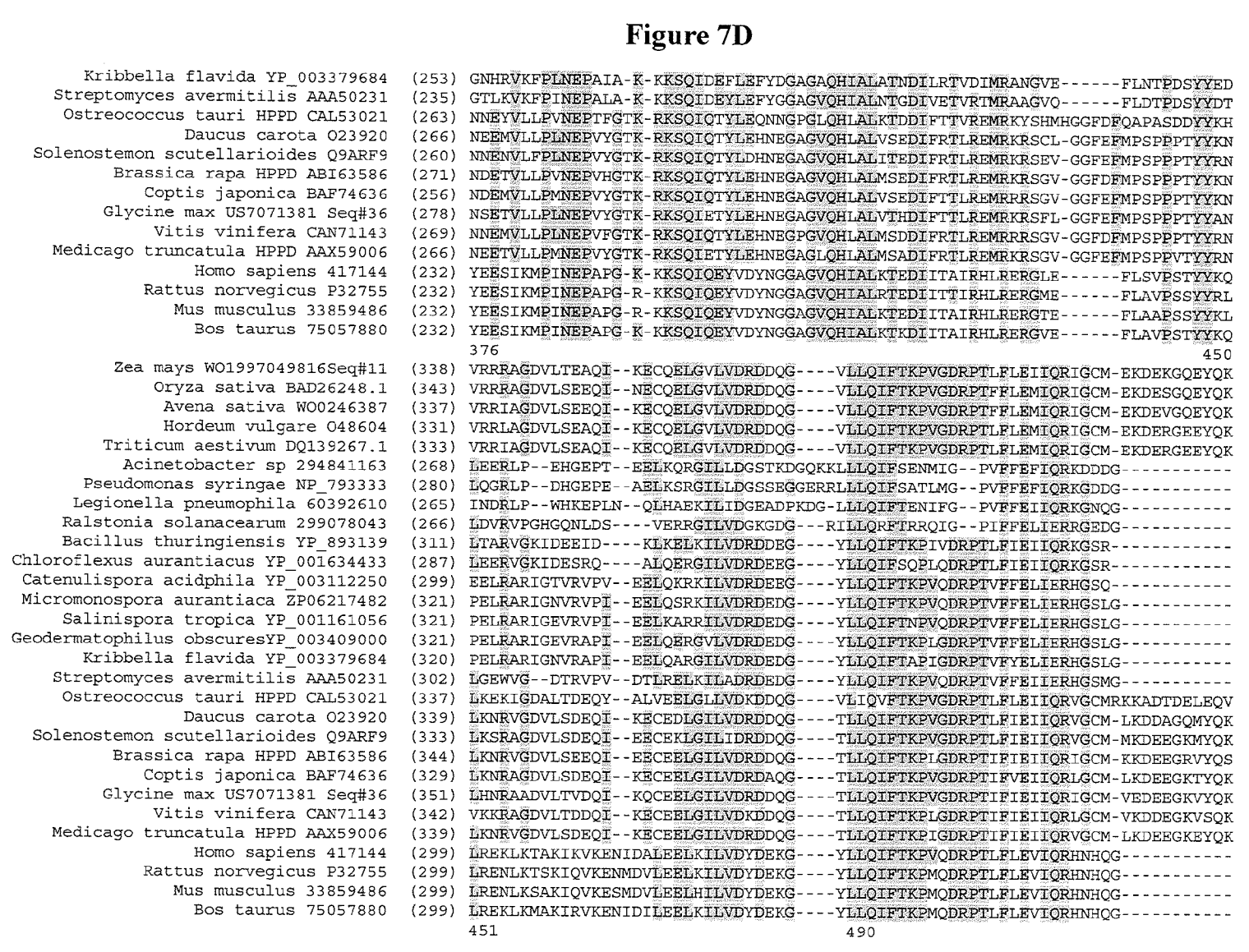

A fragment of polynucleotide that encodes a biologically active portion of a CTP-polypeptide will encode at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 60, 65, 70, 75, 80, 85 contiguous amino acids, or up to the total number of amino acids present in any one of SEQ ID NOS: 1, 2, 3, 4, 5, 6, 7, 8 or 58 or any one of the N-terminal regions (about amino acids 1-17, 1-19, 1-20, 1-23, 1-30, 1-40 or about 1-53, 1-86) of the HPPD polypeptide as set forth in FIG. 2 or 7 or in any one of SEQ ID NOS: 1, 2, 3, 4, 5, 6, 7, 8 or 58. Fragments of a CTP-encoding sequence that are useful as hybridization probes or PCR primers generally need not encode a biologically active portion of an HPPD protein.

"Variant" protein is intended to mean a protein derived from the protein by deletion (i.e., truncation at the 5' and/or 3' end) and/or a deletion or addition of one or more amino acids at one or more internal sites in the native protein and/or substitution of one or more amino acids at one or more sites in the native protein. Variant proteins encompassed are biologically active, that is they continue to possess the desired biological activity of the native protein, that is, have CTP activity. Such variants may result from, for example, genetic polymorphism or from human manipulation.

For polynucleotides, a variant comprises a polynucleotide having a deletion (i.e., truncations) at the 5' and/or 3' end and/or a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the CTPs disclosed herein. Naturally occurring variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis or gene synthesis but which still encode a CTP.

Figure 6:
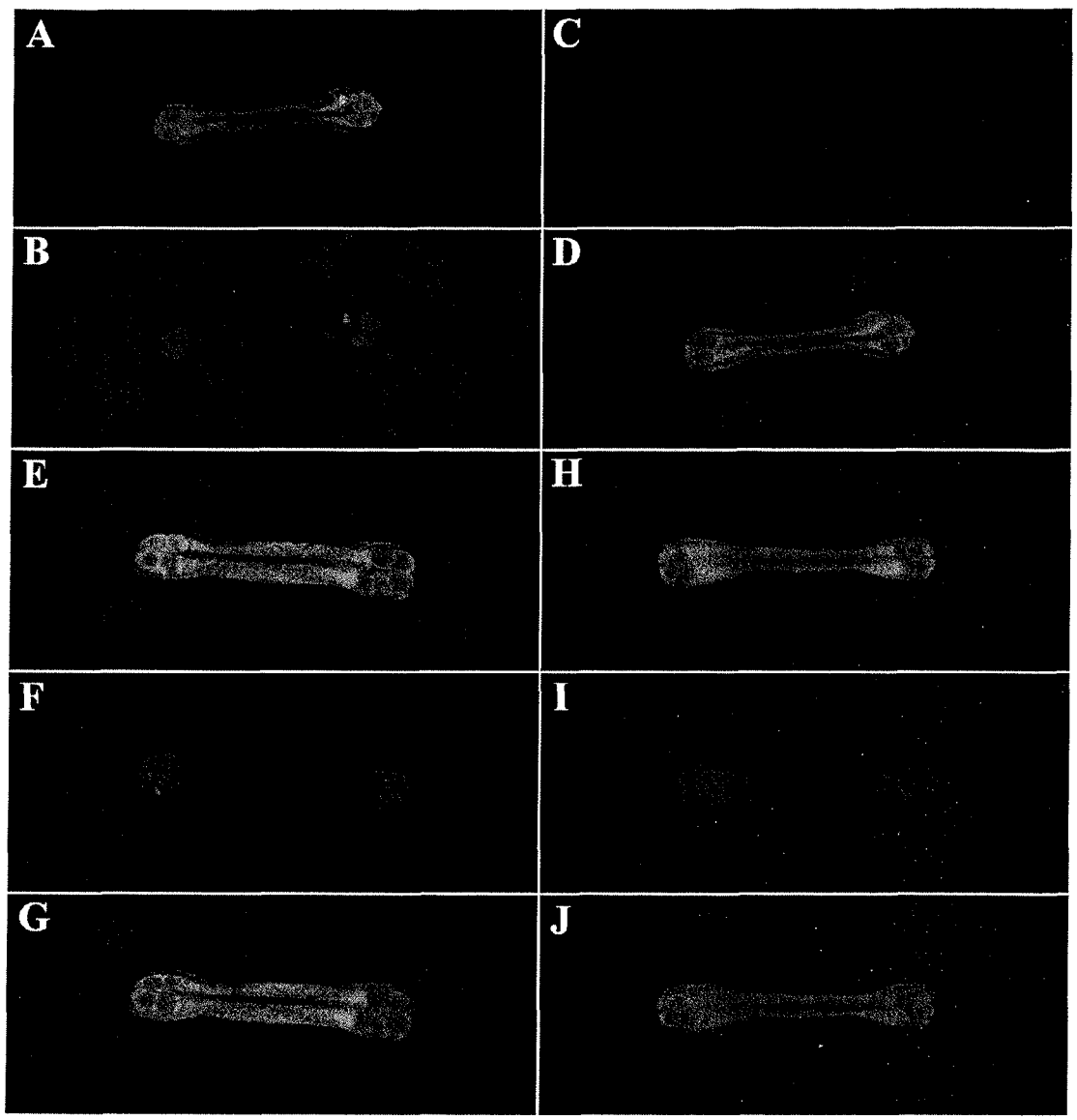
FIG. 6 provides fluorescence microscopy of maize leaf tissue transformed by co-bombardment with plasmids coding for cycle 3 green fluorescence protein in combination with a plasmid coding for either Rubisco activase CTP fused to DsRed (A-D), the N-terminal 50 amino acids of maize HPPD fused to DsRed (E-G), or untargeted DsRed (H-J). The red channel (Figs. B, F and I) shows the pattern of DsRed fluorescence, the green channel (Figs. D, G, and J) cytosolic C3GFP fluorescence and the blue channel (Fig. C) chlorophyll autofluorescence. Overlays of the red and green channels are shown in figures A, E and H.

Biologically active variants of a CTP (and the polynucleotide encoding the same) will have at least about 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more sequence identity to the polypeptide of any one of SEQ ID NO: 1, 2, 3, 4, 5, 6, 7, 8, or 58 or to the N-terminal region (about 1-53, about 1-17, about 1-19, about 1-20, about 1-23, about 1-30, about 1-40, about 1-60, about 1-70, about 1-75, about 1-80, about 1-85) of the HPPD polypeptides as set forth in FIGS. 2 and 6 or in any one of SEQ ID NOS: 1-8 or 58.

The CTP-sequences and the active variants and fragments thereof may be altered in various ways including amino acid substitutions, deletions, truncations, and insertions. Methods for such manipulations are generally known in the art. For example, amino acid sequence variants and fragments of the CTPs can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Obviously, the mutations that will be made in the DNA encoding the variant must not place the sequence out of reading frame and optimally will not create complementary regions that could produce secondary mRNA structure. See, EP Patent Application Publication No. 75,444.

Variant polynucleotides and proteins also encompass sequences and proteins derived from a mutagenic and recombinogenic procedure such as DNA shuffling. With such a procedure, one or more different CTP-sequences can be manipulated to create a new CTP possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the CTP sequences disclosed herein and other known CTPs to obtain a new polynucleotide coding for a polypeptide with an improved property of interest, such as an improved efficiency of transport to the chloroplast. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

III. Sequence Comparisons

The following terms are used to describe the sequence relationships between two or more polynucleotides or polypeptides: (a) "reference sequence", (b) "comparison window", (c) "sequence identity", and, (d) "percent sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence or protein sequence.

(b) As used herein, "comparison window" makes reference to a contiguous and specified segment of a polypeptide sequence, wherein the polypeptide sequence in the comparison window may comprise additions or deletions (i.e., gaps) compared to the reference sequence (which does not comprise additions or deletions) for optimal alignment of the two polypeptides. Generally, the comparison window is at least 5, 10, 15, or 20 contiguous amino acids in length, or it can be 30, 40, 50, 100, or longer. Those of skill in the art understand that to avoid a high similarity to a reference sequence due to inclusion of gaps in the polypeptide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. BLASTP protein searches can be performed using default parameters. See, blast.ncbi.nlm.nih.gov/Blast.cgi.

To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, or PSI-BLAST, the default parameters of the respective programs (e.g., BLASTN for nucleotide sequences, BLASTP for proteins) can be used. See www.ncbi.nlm.nih.gov. Alignment may also be performed manually by inspection.

In one embodiment, sequence identity/similarity values provided herein refer to the value obtained using GAP Version 10 using the following parameters: % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity). When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percent sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percent sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percent sequence identity.

(e) Two sequences are "optimally aligned" when they are aligned for similarity scoring using a defined amino acid substitution matrix (e.g., BLOSUM62), gap existence penalty and gap extension penalty so as to arrive at the highest score possible for that pair of sequences. Amino acids substitution matrices and their use in quantifying the similarity between two sequences are well-known in the art and described, e.g., in Dayhoff et al. (1978) "A model of evolutionary change in proteins." In "Atlas of Protein Sequence and Structure," Vol. 5, Suppl. 3 (ed. M.O. Dayhoff), pp. 345-352. Natl. Biomed. Res. Found., Washington, D.C. and Henikoff et al. (1992) Proc. Natl. Acad. Sci. USA 89:10915-10919. The BLOSUM62 matrix is often used as a default scoring substitution matrix in sequence alignment protocols such as Gapped BLAST 2.0. The gap existence penalty is imposed for the introduction of a single amino acid gap in one of the aligned sequences, and the gap extension penalty is imposed for each additional empty amino acid position inserted into an already opened gap. The gap existence penalty is imposed for the introduction of a single amino acid gap in one of the aligned sequences, and the gap extension penalty is imposed for each additional empty amino acid position inserted into an already opened gap. The alignment is defined by the amino acids positions of each sequence at which the alignment begins and ends, and optionally by the insertion of a gap or multiple gaps in one or both sequences, so as to arrive at the highest possible score. While optimal alignment and scoring can be accomplished manually, the process is facilitated by the use of a computer-implemented alignment algorithm, e.g., gapped BLAST 2.0, described in Altschul et al. (1997) *Nucleic Acids Res.* 25:3389-3402, and made available to the public at the National Center for Biotechnology Information Website (http://www.ncbi.nlm.nih.gov). Optimal alignments, including multiple alignments, can be prepared using, e.g., PSI-BLAST, available through http://www.ncbi.nlm.nih.gov and described by Altschul et al. (1997) *Nucleic Acids Res.* 25:3389-3402.

As used herein, similarity score and bit score is determined employing the BLAST alignment used the BLOSUM62 substitution matrix, a gap existence penalty of 11, and a gap extension penalty of 1. For the same pair of sequences, if there is a numerical difference between the scores obtained when using one or the other sequence as query sequences, a greater value of similarity score is selected.

IV. Polynucleotides/Polypeptides of Interest

Any polynucleotide of interest (i.e., the "polypeptide of interest") may be used with the CTP-encoding sequences disclosed herein. Such polynucleotides/polypeptides of interest include, but are not limited to, herbicide-tolerance coding sequences, insecticidal coding sequences, nematicidal coding sequences, antimicrobial coding sequences, antifungal coding sequences, antiviral coding sequences, abiotic and biotic stress tolerance coding sequences, or sequences modifying plant traits such as yield, grain quality, nutrient content, starch quality and quantity, nitrogen fixation and/or utilization, and oil content and/or composition. More specific polynucleotides of interest for the present invention include, but are not limited to, genes that improve crop yield, polypeptides that improve desirability of crops, genes encoding proteins conferring resistance to abiotic stress, such as drought, nitrogen, temperature, salinity, toxic metals or trace elements, or those conferring resistance to toxins such as pesticides and herbicides, or to biotic stress, such as attacks by fungi, viruses, bacteria, insects, and nematodes, and development of diseases associated with these organisms. It is recognized that any polypeptides of interest can be operably linked to the CTP-encoding sequences of the invention and expressed in a plant, so long as the polypeptide encoded by the polynucleotide is functional in chloroplasts.

These nucleotide sequences of interest may encode proteins involved in providing disease or pest resistance. By "disease resistance" or "pest resistance" is intended that the plants avoid the harmful symptoms that are the outcome of the plant-pathogen interactions. Disease resistance and insect resistance genes such as lysozymes or cecropins for antibacterial protection, or proteins such as defensins, glucanases or chitinases for antifungal protection, or *Bacillus thuringiensis* endotoxins, protease inhibitors, collagenases, lectins, or glycosidases for controlling nematodes or insects are all examples of useful gene products.

"Pest" includes, but is not limited to, insects, fungi, bacteria, viruses, nematodes, mites, ticks, and the like. Insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera, Lepidoptera, and Diptera. Viruses include but are not limited to tobacco or cucumber mosaic virus, ringspot virus, necrosis virus, maize dwarf mosaic virus, etc. Nematodes include but are not limited to parasitic nematodes such as root knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include but are not limited to *Pratylenchus* spp. Fungal pests include those that cause leaf, yellow, stripe and stem rusts.

An "herbicide resistance protein" or a protein resulting from expression of an "herbicide resistance-encoding nucleic acid molecule" includes proteins that confer upon a cell the ability to tolerate a higher concentration of an herbicide than cells that do not express the protein, or to tolerate a certain concentration of an herbicide for a longer period of time than cells that do not express the protein. Herbicide resistance traits may be introduced into plants by genes coding for resistance to herbicides that act to inhibit the action of acetolactate synthase (ALS), in particular the sulfonylurea-type herbicides, genes coding for resistance to herbicides that act to inhibit the action of glutamine synthase, such as phosphinothricin or basta (e.g., the bar gene), glyphosate (e.g., the EPSP synthase gene), HPPD inhibitors (e.g, the HPPD gene) or other such genes known in the art. See, for example, U.S. Pat. Nos. 7,626,077, 5,310,667, 5,866,775, 6,225,114, 6,248,876, 7,169,970, and 6,867,293, each of which is herein incorporated by reference.

Polynucleotides that improve crop yield include dwarfing genes, such as Rht1 and Rht2 (Peng et al. (1999) *Nature* 400:256-261), and those that increase plant growth, such as ammonium-inducible glutamate dehydrogenase. Polynucleotides that improve desirability of crops include, for example, those that allow plants to have a reduced saturated fat content, those that boost the nutritional value of plants, and those that increase grain protein. Polynucleotides that improve salt tolerance are those that increase or allow plant growth in an environment of higher salinity than the native environment of the plant into which the salt-tolerant gene(s) has been introduced.

Polynucleotides/polypeptides that influence amino acid biosynthesis include, for example, anthranilate synthase (AS; EC 4.1.3.27) which catalyzes the first reaction branching from the aromatic amino acid pathway to the biosynthesis of tryptophan in plants, fungi, and bacteria. In plants, the chemical processes for the biosynthesis of tryptophan are compartmentalized in the chloroplast. See, for example, US Pub. 20080050506, herein incorporated by reference. Additional sequences of interest include Chorismate Pyruvate Lyase (CPL) which refers to a gene encoding an enzyme which catalyzes the conversion of chorismate to pyruvate and pHBA. The most well characterized CPL gene has been isolated from *E. coli* and bears the GenBank accession number M96268. See, U.S. Pat. No. 7,361,811, herein incorporated by reference. Additional sequences of interest are discussed in more detail below.

a. Hydroxyphenylpyruvate Dioxygenase (HPPD) Polynucleotides and Polypeptides

In one embodiment, the CTP-encoding sequence is operably linked to a heterologous polynucleotide encoding a hydroxphenylpyruvate dioxygenase (HPPD) polypeptide. Various HPPD polypeptides and active variants and fragments thereof are known, as discussed below.

Hydroxyphenylpyruvate dioxygenase (HPPD) converts hydroxyphenylpyruvate, derived from the aromatic amino acid biosynthesis pathway, to homogentisate. In plants, homogentisate is a precursor of tocopherols and plastoquinones, an electron carrier essential in the biosynthesis of carotenoids. Consequently, when HPPD is inhibited by herbicide inhibitors, the plant can not protect itself from the radicals generated by light activation of chlorophyll. More specifically, inhibition of HPPD polypeptide leads to the depletion of protective pigments in the plant tissue resulting in bleaching of tissues which leaves the plants vulnerable to damage by light. HPPD inhibitors are an important class of herbicides. Transgenes that confer crop tolerance to HPPD inhibitors would be of significant value, especially for managing weed resistance to glyphosate.

As used herein, "Hydroxyphenylpyruvate dioxygenase" and "HPPD" "4-hydroxy phenyl pyruvate (or pyruvic acid) dioxygenase (4-HPPD)" and "p-hydroxy phenyl pyruvate (or pyruvic acid) dioxygenase (p-OHPP)" are synonymous and refer to a non-heme iron-dependent oxygenase that catalyzes the conversion of 4-hydroxyphenylpyruvate to homogentisate. In organisms that degrade tyrosine, the reaction catalyzed by HPPD is the second step in the pathway. In plants, formation of homogentisate is necessary for the synthesis of plastoquinone, an essential redox cofactor, and tocopherol. The structures of various HPPD polypeptides are known. See, for example, FIG. 1 which provides the phylogenetic diversity of several monocot HPPD polypeptides, including sequences from *Hordeum vulgare, Avena sativa, Oryza sativa, Triticum aestivum*, and *Zea mays*. FIG. 2 provides the phylogenetic diversity of several dicot HPPD polypeptides including *Daucus carota, Solenosteman sautellarioides, Picea sitchensis, Abutilon theophrasti, Arabidopsis thaliana, Brassica rapa, Coptis japonica, Vitis vinifera, Glycine max*, and *Medicago truncatula*. HPPD polypeptides from microbes and mammals are also known and non-limiting examples of these sequences appear in FIG. 7.

Various variants of HPPD sequences are also known. See, for example, U.S. Provisional Application 61/401,456, filed Aug. 13, 2010, *Compositions and Methods Comprising*

Sequences having Hydroxyphenylpyruvate Dioxygenase (HPPD) Activity, herein incorporated by reference in it entirety. See, also, US 2003/0066102, WO97/49816, US 2010/0197503, U.S. Pat. No. 7,312,379, U.S. Pat. No. 6,768, 044, U.S. Pat. No. 6,245,698, U.S. Pat. No. 6,268,549, and U.S. Pat. No. 6,118,050, the contents of each is herein incorporated by reference in its entirety. A review of the various structures of HPPD polypeptides from microbes, mammals and plants can be found, for example, in Moran et al. (2005) *Archives of Biochemistry and Biophysics* 433:117-128, herein incorporated by reference in its entirety.

As used herein, "hydroxyphenylpyruvate dioxygenase activity" or "HPPD activity" refers to the conversion of 4-hydroxyphenylpyruvate to homogentisate. As used herein, a polypeptide having "HPPD activity" comprises an HPPD polypeptide or an active variant or fragment thereof that retains sufficient HPPD activity such that (i) when expressed at sufficient levels in a cell that requires HPPD activity for viability, the HPPD polypeptide or active variant or fragment thereof exhibits sufficient HPPD activity to maintain viability of the cell in which it is expressed; or (ii) when expressed in a cell that requires HPPD activity for viability, the HPPD polypeptide or active variant or fragment thereof, when expressed in combination with one or more additional HPPD polypeptides results in the viability of the cell. Methods to determine such kinetic parameters (i.e., $K_m$, $k_{cat}$, $k_{cat}/K_m$) are known. See, for example, U.S. Provisional Application 61/401,456, filed Aug. 13, 2010 Compositions and Methods Comprising Sequences having Hydroxyphenylpyruvate Dioxygenase (HPPD) Activity, herein incorporated by reference.

In order to provide plants with tolerance to commercially useful application rates of at least one desired HPPD inhibitor, it is advantageous to use polynucleotides which encode HPPD polypeptides having sufficient HPPD activity and having an insensitivity to inhibition by at least one or more HPPD inhibitor.

As used herein, an "HPPD inhibitor" comprises any compound or combinations of compounds which decrease the ability of HPPD to catalyze the conversion of 4-hydroxyphenylpyruvate to homogentisate. In specific embodiments, the HPPD inhibitor comprises a herbicidal inhibitor of HPPD. Non-limiting examples of HPPD inhibitors include, triketones (such as, mesotrione, sulcotrione, topramezone, and tembotrione); isoxazoles (such as, pyrasulfotole and isoxaflutole); pyrazoles (such as, benzofenap, pyrazoxyfen, and pyrazolynate); and benzobicyclon. Agriculturally acceptable salts of the various inhibitors include salts, the cations or anions of which are known and accepted in the art for the formation of salts for agricultural or horticultural use. See, for example, WO2005/053407 herein incorporated by reference.

The insensitivity of an HPPD inhibitor can be determined by assaying the insensitivity of a cell, a plant, a plant cell expressing the HPPD polypeptide or active fragment or variant thereof. In such instances, the cell, plant, or plant cell expressing an HPPD sequence displays an insensitivity to an HPPD inhibitor or to a combination of HPPD inhibitors when compared to a control cell, plant or plant cell not expressing the HPPD sequence. "Increased tolerance" to a herbicide is demonstrated when plants which display the increased tolerance to a herbicide are subjected to the HPPD inhibitor and a dose/response curve is shifted to the right when compared with that provided by an appropriate control plant. Such dose/response curves have "dose" plotted on the x-axis and "percentage injury", "herbicidal effect" etc. plotted on the y-axis. Plants which are substantially "resistant" or "tolerant" to the herbicide exhibit few, if any, bleached, necrotic, lytic, chlorotic or other lesions and are not stunted, wilted or deformed when subjected to the herbicide at concentrations and rates which are typically employed by the agricultural community to kill weeds in the field.

V. Novel Hydroxyphenylpyruvate Dioxygenase (HPPD) Sequences

Compositions are further provided comprising a novel HPPD polypeptide comprising the CTP set forth in SEQ ID NO: 58 and active variants and fragments thereof. In specific embodiments, such HPPD encoding sequences include the polynucleotide set forth in SEQ ID NO: 60 and the polypeptide set forth in SEQ ID NO: 57, and active variants and fragments thereof. Such polypeptides are capable of being transported into the chloroplast of a plant cell. In some embodiments, the polynucleotide set forth in SEQ ID NO: 60 or an active variant or fragment thereof is operably linked to a heterologous promoter.

In specific embodiments, active fragments and variants of the HPPD sequence as set forth in SEQ ID NO: 60 are provided. Such fragments comprise at least 16, 20, 50, 75, 100, 150, 200, 250, 300, 350, 400, 450, 500, 550, 600, 650, 700, 800, 900, 1,000, 1,100, 1,200, 1,300, or 1,450 contiguous nucleotides, or up to the number of nucleotides present in SEQ ID NO: 60. Generally, variants of SEQ ID NO: 60 will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to SEQ ID NO: 60 as determined by sequence alignment programs and parameters described elsewhere herein. Active fragments and variants of SEQ ID NO: 60 will continue to encode a polypeptide having HPPD activity and which can be transported into the chloroplast of a plant cell.

The HPPD promoter as described in SEQ ID NO:1 of U.S. Provisional Application No. 61/501,042 leads to the production of at least two major transcripts from at least two transcription start sites (TSS1 and TSS2, see FIG. 5 of U.S. Provisional Application No. 61/501,042). The longer transcript initiates SEQ ID NO: 60 (encoding SEQ ID NO: 57). Parts of the genomic sequence transcribed to produce the longer transcript also act to promote transcriptional regulatory activity for the shorter transcript. Various polynucleotide sequences are known in the art which comprise multiple transcriptional start sites that encode products targeted to multiple cellular compartments. See for example, Small (1998) *Plant Mol. Biol.* 38:265-277 and Thatcher (2007) *J of Biol. Chem.* 282:28915-28928. The polypeptide set forth in SEQ ID NO: 57 is localized to the chloroplast, while the polypeptide encoded by the shorter transcript is localized to the cytosol.

Further provided are variant HPPD proteins as set forth in SEQ ID NO: 57. "Variant" protein is intended to mean a protein derived from the native protein by deletion or addition of one or more amino acids at one or more internal sites in the native protein and/or substitution of one or more amino acids at one or more sites in the native protein. Variant proteins encompassed by the present invention are biologically active, that is they continue to possess the desired biological activity of the native protein, that is, HPPD activity and wherein the protein is transported into the chloroplast of a plant cell. Such variants may result from, for example, genetic polymorphism or from human manipulation. Biologically active variants of a HPPD proteins disclosed herein will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence set forth in SEQ ID NO: 57 as determined by sequence alignment programs and parameters described elsewhere herein. A biologically active variant of a protein of the invention may differ from SEQ ID NO: 57 by as few as 1-15 amino acid residues, as few as 1-10, such as 6-10, as few as 5, as few as 4, 3, 2, or even 1 amino acid residue.

Fragments of amino acid sequences include peptides comprising amino acid sequences sufficiently identical to or derived from the amino acid sequence of a HPPD protein, or a partial-length protein and exhibiting HPPD activity but which include fewer amino acids than the full-length HPPD-related proteins disclosed herein. A biologically active portion of a HPPD protein can be a polypeptide that is, for example, 10, 25, 50, 100, 150, 200 contiguous amino acids in length, or up to the total number of amino acids present in a full-length HPPD protein of the current invention (i.e., of SEQ ID NO: 57). Such biologically active portions can be prepared by recombinant techniques and evaluated for one or more of the functional activities of a native HPPD protein, including but not limited to transport into the chloroplast of a plant cell. As used herein, a fragment comprises at least 5 contiguous amino acids of SEQ ID NO: 57. The invention encompasses other fragments, however, such as any fragment in the protein greater than 6, 7, 8, or 9 amino acids.

The polynucleotide encoding SEQ ID NO: 57 or active fragments and variants thereof can be provided in an expression cassette for expression in a plant or organism of interest. The expression cassette can include 5' and 3' regulatory sequences operably linked to the polynucleotide of the invention. An operable linkage between a polynucleotide of interest and a regulatory sequence (i.e., a promoter) is a functional link that allows for expression of the polynucleotide of interest. Operably linked elements may be contiguous or non-contiguous. In some embodiments, the polynucleotide set forth in SEQ ID NO: 60 can be operably linked to a heterologous promoter. When used to refer to the joining of two protein coding regions, by operably linked is intended that the coding regions are in the same reading frame. The cassette may additionally contain at least one additional polynucleotide to be cotransformed into the organism. Alternatively, the additional polypeptide(s) can be provided on multiple expression cassettes. Expression cassettes can be provided with a plurality of restriction sites and/or recombination sites for insertion of the polynucleotide to be under the transcriptional regulation of the regulatory regions. The expression cassette may additionally contain selectable marker genes.

Further provided are plants, plant cells, and seeds having a heterologous polynucleotide construct comprising an expression cassette having a promoter operably linked to a polynucleotide encoding the polypeptide set forth in SEQ ID NO: 57 or an active variant or fragment thereof, wherein the promoter is heterologous to said polynucleotide.

VI. Plants

Plants, plant cells, plant parts and seeds, and grain having the polynucleotide comprising the CTP-encoding sequence operably linked to a heterologous polynucleotide encoding a polypeptide of interest are provided. In specific embodiments, the plants and/or plant parts have stably incorporated at least one of the chimeric polynucleotides disclosed herein or an active variant or fragment thereof. Thus, plants, plant cells, plant parts and seed are provided which comprise at least one polynucleotide comprising a CTP-encoding sequence operably linked to a heterologous polynucleotide encoding a polypeptide of interest, wherein the chloroplast transit peptide comprises any one of SEQ ID NOS: 1, 2, 3, 4, 5, 6, 7, 8, 58 or active variants and fragments thereof, or a CTP-encoding sequence of any one of the N-terminal regions (about amino acids 1-53, 1-20, 1-23, 1-17, 1-30, 1-40, 1-60, 1-70, 1-80, 1-85) of an HPPD polypeptide set forth in FIG. 2 or 7 or an active variant or fragment thereof. Further provided are plants, plant cells and seeds comprising the HPPD encoding sequences as set forth in SEQ ID NO: 57 and the polypeptide set forth in SEQ ID NO: 60, and active variants and fragments thereof.

Further provided are plants, plant cells, plant parts and seeds and grain having stably incorporated into their genome, the polynucleotide comprising a CTP-encoding sequence operably linked to a heterologous polynucleotide encoding a polypeptide of interest.

In specific embodiments, the chimeric polynucleotide or the HPPD encoding sequences in the plant or plant part is operably linked to a constitutive, tissue-preferred, or other promoter for expression in plants.

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

The chimeric polynucleotides, the HPPD encoding sequences and active variant and fragments thereof disclosed herein may be used for transformation of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifblia*), almond (*Prunus amygdalus*), sugar beets (*Beta vulgaris*), sugarcane (*Saccharum* spp.), oats, barley, vegetables, ornamentals, and conifers.

Vegetables include, but not limited to, tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include, but not limited to, azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pukherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*), and Poplar and Eucalyptus. In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

In some embodiments, the polynucleotides comprising the CTP-encoding sequence operably linked to the polynucleotide encoding the polypeptide of interest are engineered into a molecular stack. Thus, the various plants, plant cells and seeds disclosed herein can further comprise one or more traits of interest, and in more specific embodiments, the plant, plant part or plant cell is stacked with any combination of polynucleotide sequences of interest in order to create plants with a desired combination of traits. As used herein, the term "stacked" includes having the multiple traits present in the same plant.

These stacked combinations can be created by any method including, but not limited to, breeding plants by any conventional methodology, or genetic transformation. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

A "subject plant or plant cell" is one in which genetic alteration, such as transformation, has been affected as to a gene of interest, or is a plant or plant cell which is descended from a plant or cell so altered and which comprises the alteration. A "control" or "control plant" or "control plant cell" provides a reference point for measuring changes in phenotype of the subject plant or plant cell.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

VII. Polynucleotide Constructs

The use of the term "polynucleotide" is not intended to limit the present invention to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

The chimeric polynucleotides or the HPPD encoding sequences disclosed herein can be provided in expression cassettes for expression in the plant of interest. The cassette can include 5' and 3' regulatory sequences operably linked to the chimeric polynucleotide or active variant or fragment thereof. "Operably linked" is intended to mean a functional linkage between two or more elements. For example, an operably linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the chimeric polynucleotide or active variant or fragment thereof to be under the transcriptional regulation of the regulatory regions. The expression cassette may additionally contain selectable marker genes.

The expression cassette can include in the 5'-3' direction of transcription, a transcriptional and translational initiation region (i.e., a promoter), a CTP-encoding sequence or active variant or fragment thereof operably linked to a polynucleotide encoding a polypeptide of interest and a transcriptional and translational termination region (i.e., termination region) functional in plants. The regulatory regions (i.e., promoters, transcriptional regulatory regions, and translational termination regions) and/or the CTP-encoding sequence and/or the polynucleotide encoding the polypeptide of interest may be native/analogous to the host cell or to each other. Alternatively, the regulatory regions and/or the CTP-encoding sequence and/or the polynucleotide encoding the polypeptide of interest may be heterologous to the host cell or to each other. In specific embodiments, the CTP-encoding sequenced is operably linked to the 5' end of the polynucleotide of interest, such that, in the resulting chimeric polypeptide, the CTP is operably linked to the N-terminal region of the polypeptide of interest.

As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

The termination region may be native with the transcriptional initiation region, may be native with the operably linked polynucleotide sequence of interest, may be native with the plant host, or may be derived from another source (i.e., foreign or heterologous) to the promoter, the CTP, the polynucleotide sequence of interest, the plant host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Where appropriate, the polynucleotides may be optimized for increased expression in the transformed plant. That is, the polynucleotides can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (*Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385. See also, Della-Cioppa et al. (1987) *Plant Physiol.* 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used to express the various sequences of interest including the native promoter of the polynucleotide sequence of interest. The promoters can be selected based on the desired outcome. Such promoters include, for example, constitutive, tissue-preferred, or other promoters for expression in plants.

Constitutive promoters include, for example, the core promoter of the Rsyn7/synthetic core 11 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Bioi.* 12:619-632 and Christensen et al. 20 (1992) *Plant Mol. Bioi.* 18:675-689); pEMU (Last et al. (1991) *Theor. Appl. Genet.* 81:581-588); MAS (Velten et al. (1984) *EMBO J* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611. Additional promoters of interest are set forth in U.S. Utility application Ser. No. 13/209,017, now issued U.S. Pat. No. 8,993,837, entitled "Chimeric Promoters And Methods of Use" filed concurrently herewith and herein incorporated by reference in its entirety.

Tissue-preferred promoters can be utilized to target enhanced HPPD expression within a particular plant tissue. Tissue-preferred promoters include those described in Yamamoto et al. (1997) *Plant J.* 12(2):255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Synthetic promoters can be used to express the polynucleotide sequences of interest or biologically active variants and fragments thereof.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glyphosate, glufosinate ammonium, bromoxynil, sulfonylureas, dicamba, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004)

*Plant Cell* 16:215-28), cyan florescent protein (CYP) (Bolte et al. (2004) *J Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Bairn et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference. The above list of selectable marker genes is not meant to be limiting. Any selectable marker gene can be used in the present invention, including for example, DsRed as described in Example 3, 4, 6 or 9 and FIG. 5.

IIX. Method of Introducing

Various methods can be used to introduce a sequence of interest into a plant or plant part. "Introducing" is intended to mean presenting to the plant, plant cell or plant part the polynucleotide or polypeptide in such a manner that the sequence gains access to the interior of a cell of the plant. The methods of the invention do not depend on a particular method for introducing a sequence into a plant or plant part, only that the polynucleotide or polypeptides gains access to the interior of at least one cell of the plant. Methods for introducing polynucleotide or polypeptides into plants are known in the art including, but not limited to, stable transformation methods, transient transformation methods, and virus-mediated methods.

"Stable transformation" is intended to mean that the nucleotide construct introduced into a plant integrates into the genome of the plant and is capable of being inherited by the progeny thereof "Transient transformation" is intended to mean that a polynucleotide is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. No. 5,563,055 and U.S. Pat. No. 5,981,840), direct gene transfer (Paszkowski et al. (1984) *EMBO J.* 3:2717-2722), and ballistic particle acceleration (see, for example, U.S. Pat. No. 4,945,050; U.S. Pat. No. 5,879,918; U.S. Pat. No. 5,886,244; and, 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In specific embodiments, the polynucleotide comprising the CTP-encoding sequence operably linked to a heterologous polynucleotide encoding the polypeptide of interest or the sequence encoding the HPPD polypeptide can be provided to a plant using a variety of transient transformation methods. Such transient transformation methods include, but are not limited to, the introduction of the protein or active variants and fragments thereof directly into the plant. Such methods include, for example, microinjection or particle bombardment. See, for example, Crossway et al. (1986) *Mol. Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107:775-784, all of which are herein incorporated by reference.

In other embodiments, the polynucleotide may be introduced into plants by contacting plants with a virus or viral nucleic acids. Generally, such methods involve incorporating a nucleotide construct of the invention within a DNA or RNA molecule. It is recognized that a protein sequence may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the invention can be contained in a transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome. Other methods to target polynucleotides are set forth in WO 2009/114321 (herein incorporated by reference), which describes "custom" meganucleases produced to modify plant genomes, in particular the genome of maize. See, also, Gao et al. (2010) *Plant Journal* 1:176-187.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide of the invention, for example, an expression cassette of the invention, stably incorporated into their genome.

IX. Methods of Use

Methods of the present invention are directed to the proper expression, translocation, and processing of chloroplast-targeted sequences in plants and plant cells under the control of the CTP sequences disclosed herein. For the purposes of the present invention, a "processed" chloroplast targeted protein is one in which the CTP has been removed. At the time of translocation of a chloroplast targeted protein into the chloroplast of a plant cell, the CTP is removed from the targeted protein by cleavage at a particular "cleavage site" between the CTP and the mature protein. The cleavage site can be determined experimentally, or may be predicted based on sequence structure (e.g., by alignment of the unprocessed protein with chloroplast targeted proteins in which the cleavage site is known, by analyzing the sequence for the presence of characteristic CTP domains, and the like) or by using one or more algorithms for cleavage site prediction as discussed elsewhere herein (e.g., SignalP).

Thus, methods for targeting a polypeptide of interest to the chloroplast are provided. Such methods comprise introducing a chimeric polynucleotide comprising a CTP-encoding sequence operably linked to a polynucleotide encoding a polypeptide of interest into a plant cell and expressing the chimeric polynucleotide in the plant cell.

Depending on the polypeptide of interest targeted to the chloroplast, the transgenic plants may have a change in phenotype, including, but not limited to, an altered pathogen or insect defense mechanism, an increased resistance to one or more herbicides, an increased ability to withstand stressful environmental conditions, a modified ability to produce starch, a modified level of starch production, a modified oil content and/or composition, a modified ability to utilize, partition and/or store nitrogen, and the like. These results can be achieved through the expression and targeting of a polypeptide of interest to chloroplasts in plants, wherein the polypeptide of interest functions in the chloroplast. The CTP sequences of the invention are useful for targeting native sequences as well as heterologous (non-native) sequences in plants.

X. Stacking Other Traits of Interest

In specific embodiments, the HPPD polynucleotides or active variants and fragments thereof disclosed herein or the various sequences encoding the chimeric polypeptides are engineered into a molecular stack. Thus, the various plants, plant cells and seeds disclosed herein can further comprise one or more traits of interest, and in more specific embodiments, the plant, plant part or plant cell is stacked with any combination of polynucleotide sequences of interest in order to create plants with a desired combination of traits. As used herein, the term "stacked" includes having the multiple traits present in the same plant (i.e., both traits are incorporated into the nuclear genome, one trait is incorporated into the nuclear genome and one trait is incorporated into the genome of a plastid, or both traits are incorporated into the genome of a plastid). In one non-limiting example, "stacked traits" comprise a molecular stack where the sequences are physically adjacent to each other. A trait, as used herein, refers to the phenotype derived from a particular sequence or groups of sequences. In one embodiment, the molecular stack comprises at least one additional polynucleotide that also confers tolerance to at least one HPPD inhibitor and/or at least one additional polynucleotide that confers tolerance to a second herbicide.

Thus, in one embodiment, the plants, plant cells or plant part having the HPPD polynucleotide or active variants or fragments thereof disclosed herein or a sequence encoding the chimeric polypeptides is stacked with at least one other HPPD sequence. Such HPPD sequence include the HPPD sequence and variants and fragment thereof disclosed herein, as well as other HPPD sequence, which include but are not limited to the HPPD sequences set forth in U.S. Pat. Nos. 6,245,968 B1; 6,268,549; and 6,069,115; international publication WO 99/23886, each of which is herein incorporated by reference, and those disclosed in U.S. Utility application Ser. No. 13/208,966 entitled "Compositions and Methods Comprising Sequences Having Hydroxyphenylpyruvate Dioxygenase (HPPD) Activity" filed concurrently herewith and incorporated by reference in its entirety.

In still other embodiments, plants, plant cells, explants and expression cassettes comprising the HPPD sequences, the various sequences encoding the chimeric polypeptides, or active variants and fragments thereof are stacked with a sequence that confers tolerance to HPPD inhibitors through a different mechanism than the HPPD polypeptide. For example, a P450 sequence could be employed which provides tolerance to HPPD-inhibitors by metabolism of the herbicide. Such sequences including, but are not limited to, the NSF1 gene. See, US 2007/0214515 and US 2008/0052797 both of which are herein incorporated by reference in their entirety.

Known genes that confer tolerance to herbicides such as e.g., auxin, HPPD, glyphosate, dicamba, glufosinate, sulfonylurea, bromoxynil and norflurazon herbicides can be stacked either as a molecular stack or a breeding stack with plants expressing the traits disclosed herein. Polynucleotide molecules encoding proteins involved in herbicide tolerance include, but are not limited to, a polynucleotide molecule encoding 5-enolpyruvylshikimate-3-phosphate synthase (EPSPS) disclosed in U.S. Pat. Nos. 39,247; 6,566,587 for imparting glyphosate tolerance; polynucleotide molecules encoding a glyphosate oxidoreductase (GOX) disclosed in U.S. Pat. No. 5,463,175 and a glyphosate-N-acetyl transferase (GAT) disclosed in U.S. Pat. Nos. 7,622,641; 7,462,481; 7,531,339; 7,527,955; 7,709,709; 7,714,188 and 7,666, 643 also for providing glyphosate tolerance; dicamba monooxygenase disclosed in U.S. Pat. No. 7,022,896 and WO2007146706A2 for providing dicamba tolerance; a polynucleotide molecule encoding AAD12 disclosed in U.S. Pat. App. Pub. No. 2005731044 or WO2007053482A2 or encoding AAD1 disclosed in US20110124503A1 or U.S. Pat. No. 7,838,733 for providing tolerance to auxin herbicides (2,4-D); a polynucleotide molecule encoding hydroxyphenylpyruvate dioxygenase (HPPD) for providing tolerance to HPPD inhibitors (e.g., hydroxyphenylpyruvate dioxygenase) disclosed in e.g., U.S. Pat. No. 7,935,869; US20090055976A1; and US20110023180A1; each publication is herein incorporated by reference in its entirety.

In some embodiments, the plant or plant cells having the HPPD polynucleotides, the various sequences encoding the chimeric polypeptides or active variants or fragments thereof may be stacked with other herbicide-tolerance traits to create a transgenic plant of the invention with further improved properties. Other herbicide-tolerance polynucleotides that could be used in such embodiments include those conferring tolerance to glyphosate such as, for example, glyphosate N-acetyltransferase. See, for example, WO02/36782, US Publication 2004/0082770 and WO 2005/012515, U.S. Pat. No. 7,462,481, U.S. Pat. No. 7,405,074, each of which is herein incorporated by reference.

Additional glyphosate-tolerance traits include a sequence that encodes a glyphosate oxido-reductase enzyme as described more fully in U.S. Pat. Nos. 5,776,760 and 5,463,175. Other traits that could be combined with the HPPD sequence disclosed herein include those derived from polynucleotides that confer on the plant the capacity to produce a higher level or glyphosate insensitive 5-enolpyruvylshikimate-3-phosphate synthase (EPSPS), for example, as more fully described in U.S. Pat. Nos. 6,248,876 B1; 5,627,061; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E; and 5,491,288; and international publications WO 97/04103; WO 00/66746; WO 01/66704; and WO 00/66747. Other traits that could be combined with the HPPD sequences disclosed herein include those conferring tolerance to sulfonylurea and/or imidazolinone, for example, as described more fully in U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270.

In other embodiments, the plants or plant cell or plant part having the HPPD sequence or an active variant or fragment thereof is stacked with, for example, a sequence which confers tolerance to an ALS inhibitor. As used herein, an "ALS inhibitor-tolerant polypeptide" comprises any polypeptide which when expressed in a plant confers tolerance to at least one ALS inhibitor. A variety of ALS inhibitors are known and include, for example, sulfonylurea, imidazolinone, triazolopyrimidines, pryimidinyloxy(thio)benzoates, and/or sulfonylaminocarbonyltriazolinone herbicides. Additional ALS inhibitors are known and are disclosed elsewhere herein. It is known in the art that ALS mutations fall into different classes with regard to tolerance to sulfonylureas, imidazolinones, triazolopyrimidines, and pyrimidinyl(thio)benzoates, including mutations having the following characteristics: (1) broad tolerance to all four of these groups; (2) tolerance to imidazolinones and pyrimidinyl(thio)benzoates; (3) tolerance to sulfonylureas and triazolopyrimidines; and (4) tolerance to sulfonylureas and imidazolinones.

Various ALS inhibitor-tolerant polypeptides can be employed. In some embodiments, the ALS inhibitor-tolerant polynucleotides contain at least one nucleotide mutation resulting in one amino acid change in the ALS polypeptide. In specific embodiments, the change occurs in one of seven substantially conserved regions of acetolactate synthase. See, for example, Hattori et al. (1995) *Molecular Genetics and Genomes* 246:419-425; Lee et al. (1998) *EMBO Journal* 7:1241-1248; Mazur et al. (1989) *Ann. Rev. Plant Phys.* 40:441-470; and U.S. Pat. No. 5,605,011, each of which is incorporated by reference in their entirety. The ALS inhibitor-tolerant polypeptide can be encoded by, for example, the SuRA or SuRB locus of ALS. In specific embodiments, the ALS inhibitor-tolerant polypeptide comprises the C3 ALS mutant, the HRA ALS mutant, the S4 mutant or the S4/HRA mutant or any combination thereof. Different mutations in ALS are known to confer tolerance to different herbicides and groups (and/or subgroups) of herbicides; see, e.g., Tranel and Wright (2002) *Weed Science* 50:700-712. See also, U.S. Pat. Nos. 5,605,011, 5,378,824, 5,141,870, and 5,013,659, each of which is herein incorporated by reference in their entirety. The soybean, maize, and *Arabidopsis* HRA sequences are disclosed, for example, in WO2007/024782, herein incorporated by reference.

In some embodiments, the ALS inhibitor-tolerant polypeptide confers tolerance to sulfonylurea and imidazolinone herbicides. The production of sulfonylurea-tolerant plants and imidazolinone-tolerant plants is described more fully in U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270, which are incorporated herein by reference in their entireties for all purposes. In specific embodiments, the ALS inhibitor-tolerant polypeptide comprises a sulfonamide-tolerant acetolactate synthase (otherwise known as a sulfonamide-tolerant acetohydroxy acid synthase) or an imidazolinone-tolerant acetolactate synthase (otherwise known as an imidazolinone-tolerant acetohydroxy acid synthase).

In further embodiments, the plants or plant cell or plant part having the HPPD sequence or an active variant or fragment thereof is stacked with, for example, a sequence which confers tolerance to an ALS inhibitor and glyphosate tolerance. In one embodiment, the HPPD sequence or active variant or fragment thereof is stacked with HRA and a glyphosate N-acetyltransferase. See, WO2007/024782, 2008/0051288 and WO 2008/112019, each of which is herein incorporated by reference.

In still other embodiments, the plant or plant cell or plant part having the HPPD sequence or an active variant or fragment thereof may be stacked with, for example, aryloxyalkanoate dioxygenase polynucleotides (which confer tolerance to 2,4-D and other phenoxy auxin herbicides as well as to aryloxyphenoxypropionate herbicides as described, for example, in WO2005/107437) and dicamba-tolerance polynucleotides as described, for example, in Herman et al. (2005) *J. Biol. Chem.* 280: 24759-24767, auxin polypeptides and an acetyl coenzyme A carboxylase (ACCase) polypeptides.

Other examples of herbicide-tolerance traits that could be combined with the plant or plant cell or plant part having the HPPD sequence, the various sequences encoding the chimeric polypeptides or an active variants or fragments thereof include those conferred by polynucleotides encoding an exogenous phosphinothricin acetyltransferase, as described in U.S. Pat. Nos. 5,969,213; 5,489,520; 5,550,318; 5,874,265; 5,919,675; 5,561,236; 5,648,477; 5,646,024; 6,177,616; and 5,879,903. Plants containing an exogenous phosphinothricin acetyltransferase can exhibit improved tolerance to glufosinate herbicides, which inhibit the enzyme glutamine synthase. Other examples of herbicide-tolerance traits that could be combined with the plants or plant cell or plant part having the HPPD sequence or an active variant or fragment thereof include those conferred by polynucleotides conferring altered protoporphyrinogen oxidase (protox) activity, as described in U.S. Pat. Nos. 6,288,306 B1; 6,282,837 B1; and 5,767,373; and international publication WO 01/12825. Plants containing such polynucleotides can exhibit improved tolerance to any of a variety of herbicides which target the protox enzyme (also referred to as "protox inhibitors").

Other examples of herbicide-tolerance traits that could be combined with the plants or plant cell or plant part having the HPPD sequence, the various sequences encoding the chimeric polypeptides, or an active variant or fragment thereof include those conferring tolerance to at least one herbicide in a plant such as, for example, a maize plant or horseweed. Herbicide-tolerant weeds are known in the art, as are plants that vary in their tolerance to particular herbicides. See, e.g., Green and Williams (2004) "Correlation of Corn (Zea mays) Inbred Response to Nicosulfuron and Mesotrione," poster presented at the WSSA Annual Meeting in Kansas City, Mo., Feb. 9-12, 2004; Green (1998) Weed Technology 12: 474-477; Green and Ulrich (1993) Weed Science 41: 508-516. The trait(s) responsible for these tolerances can be combined by breeding or via other methods with the plants or plant cell or plant part having the HPPD sequence, the various sequences encoding the chimeric polypeptides or an active variants or fragments thereof to provide a plant of the invention as well as methods of use thereof.

In still further embodiments, the HPPD sequences, the various sequences encoding the chimeric polypeptides or active variants or fragments thereof can be stacked with at least one polynucleotide encoding a homogentisate solanesyltransferase (HST). See, for example, WO2010023911 herein incorporated by reference in its entirety. In such embodiments, classes of herbicidal compounds—which act wholly or in part by inhibiting HST can be applied over the plants having the HTS polypeptide.

The plant or plant cell or plant part having the HPPD sequence, the various sequences encoding the chimeric polypeptides, or an active variants or fragments thereof can also be combined with at least one other trait to produce plants that further comprise a variety of desired trait combinations including, but not limited to, traits desirable for animal feed such as high oil content (e.g., U.S. Pat. No. 6,232,529); balanced amino acid content (e.g., hordothionins (U.S. Pat. Nos. 5,990,389; 5,885,801; 5,885,802; and 5,703,409; U.S. Pat. No. 5,850,016); barley high lysine (Williamson et al. (1987) Eur. J. Biochem. 165: 99-106; and WO 98/20122) and high methionine proteins (Pedersen et al. (1986) J. Biol. Chem. 261: 6279; Kirihara et al. (1988) Gene 71: 359; and Musumura et al. (1989) Plant Mol. Biol. 12:123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)); the disclosures of which are herein incorporated by reference. Desired trait combinations also include LLNC (low linolenic acid content; see, e.g., Dyer et al. (2002) Appl. Microbiol. Biotechnol. 59: 224-230) and OLCH (high oleic acid content; see, e.g., Fernandez-Moya et al. (2005) J. Agric. Food Chem. 53: 5326-5330).

The plant or plant cell or plant part having the HPPD sequence, the various sequences encoding the chimeric polypeptides or an active variants or fragments thereof can also be combined with other desirable traits such as, for example, fumonisim detoxification genes (U.S. Pat. No. 5,792,931), avirulence and disease resistance genes (Jones et al. (1994) Science 266: 789; Martin et al. (1993) Science 262: 1432; Mindrinos et al. (1994) Cell 78: 1089), and traits desirable for processing or process products such as modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) J. Bacteriol. 170:5837-5847) facilitate expression of polyhydroxyalkanoates (PHAs)); the disclosures of which are herein incorporated by reference. One could also combine herbicide-tolerant polynucleotides with polynucleotides providing agronomic traits such as male sterility (e.g., see U.S. Pat. No. 5,583,210), stalk strength, flowering time, or transformation technology traits such as cell cycle regulation or gene targeting (e.g., WO 99/61619, WO 00/17364, and WO 99/25821); the disclosures of which are herein incorporated by reference.

In other embodiments, the plant or plant cell or plant part having the HPPD sequence, the various sequences encoding the chimeric polypeptides, or an active variants or fragments thereof may be stacked with any other polynucleotides encoding polypeptides having pesticidal and/or insecticidal activity, such as Bacillus thuringiensis toxic proteins (described in U.S. Pat. Nos. 5,366,892; 5,747,450; 5,737,514; 5,723,756; 5,593,881; Geiser et al. (1986) Gene 48: 109; Lee et al. (2003) Appl. Environ. Microbiol. 69: 4648-4657 (Vip3A); Galitzky et al. (2001) Acta Crystallogr. D. Biol. Crysiallogr. 57: 1101-1109 (Cry3Bbl); and Herman et al. (2004) J. Agric. Food Chem. 52: 2726-2734 (CrylF)), lectins (Van Damme et al. (1994) Plant Mol. Biol. 24: 825, pentin (described in U.S. Pat. No. 5,981,722), and the like. The combinations generated can also include multiple copies of any one of the polynucleotides of interest.

In another embodiment, the plant or plant cell or plant part having the HPPD sequence, the various sequences encoding the chimeric polypeptides, or an active variant or fragment thereof can also be combined with the Rcg1 sequence or biologically active variant or fragment thereof. The Rcg1 sequence is an anthracnose stalk rot resistance gene in corn. See, for example, U.S. patent application Ser. No. 11/397, 153, Ser. No. 11/397,275, and Ser. No. 11/397,247, each of which is herein incorporated by reference.

These stacked combinations can be created by any method including, but not limited to, breeding plants by any conventional methodology, or genetic transformation. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

Non-limiting embodiment include:

1. A chimeric polynucleotide comprising a nucleotide sequence encoding a chloroplast transit peptide operably linked to a heterologous polynucleotide encoding a polypeptide of interest, wherein said chloroplast transit peptide comprises
    a) an amino acid sequence comprising the amino acids of SEQ ID NO:1;
    b) an amino acid sequence having at least 90% sequence identity to SEQ ID NO: 2, 3, 4, 5, 6, 7, 8, or 58;
    c) an amino acid sequence having at least 17 consecutive amino acids of SEQ ID NO:1, 2, 3, 4, 5, 6, 7, 8, or 58; or,
    d) an amino acid sequence having at least 90% sequence identity to SEQ ID NO: 2, 3, 4, 5, 6, 7, 8, or 58 and having at least 17 consecutive amino acids of SEQ ID NO:1, 2, 3, 4, 5, 6, 7, 8, or 58.

2. The chimeric polynucleotide of embodiment 1, wherein said chloroplast transit peptide comprises SEQ ID NO: 2, 3, 4, 5, 6, 7, 8, or 58.

3. The chimeric polynucleotide of embodiment 1 or 2, wherein said polypeptide of interest comprises a 4-hydroxphenylpyruvate dioxygenase (HPPD) polypeptide having HPPD activity.

4. A nucleic acid construct comprising the chimeric polynucleotide of any one of embodiments 1-3.

5. The nucleic acid construct of embodiment 4, further comprising a promoter operably linked to said chimeric polynucleotide.

6. A cell comprising at least one chimeric polynucleotide of any of embodiments 1-3 or the nucleic acid construct of any one of embodiments 4 or 5.

7. The cell of embodiment 6, wherein said cell is a plant cell.

8. The cell of embodiment 7, wherein said polynucleotide or nucleic acid construct is stably incorporated into the genome of said plant cell.

9. The cell of any one of embodiments 7-8, wherein said plant cell is from a monocot.

10. The cell of embodiment 9, wherein said monocot is maize, wheat, rice, barley, sorghum, or rye.

11. The cell of any one of embodiments 7-8, wherein said plant cell is from a dicot.

12. The cell of embodiment 11, wherein the dicot is soybean, *Brassica*, sunflower, cotton, or alfalfa.

13. A plant comprising at least one plant cell of any one of embodiments 7-12.

14. A plant explant comprising at least one plant cell of any one of embodiments 7-12.

15. A transgenic seed produced by the plant of embodiment 13.

16. The plant, plant cell, or seed of any one of 11-15, wherein the plant, plant cell, or seed further comprises at least one polypeptide imparting tolerance to a herbicide.

17. The plant, plant cell, or seed of embodiment 16, wherein said at least one polypeptide imparting tolerance to a herbicide comprises:
    (a) a sulfonylurea-tolerant acetolactate synthase;
    (b) an imidazolinone-tolerant acetolactate synthase;
    (c) a glyphosate-tolerant 5-enolpyruvylshikimate-3-phosphate synthase;
    (d) a glyphosate-tolerant glyphosate oxido-reductase;
    (e) a glyphosate-N-acetyltransferase;
    (f) a phosphinothricin acetyl transferase;
    (g) a protoporphyrinogen oxidase.
    (h) an auxin enzyme or receptor;
    (i) a P450 polypeptide; or,
    (j) an acetyl coenzyme A carboxylase (ACCase).

18. A chimeric polypeptide encoded by the polynucleotide of any one of embodiments 1-3.

19. A method of targeting a polypeptide of interest to a chloroplast comprising expressing a chimeric polynucleotide of any one of embodiments 1-3 or the nucleic acid construct of embodiment 4 or 5 in a plant cell.

20. A method of targeting a polypeptide of interest to a chloroplast comprising introducing the chimeric polynucleotide of any one of embodiments 1-3 or the nucleic acid construct of embodiment 4 or 5 in a plant cell and expressing said chimeric polynucleotide in the plant cell.

21. The method of embodiment 19 or 20, wherein said method further comprises regenerating a transgenic plant from said plant cell.

22. The method of any one of embodiments 19-21, wherein said plant cell is from a dicot.

23. The method of embodiment 22, wherein said dicot is selected from the group consisting of soybean, *Brassica*, sunflower, cotton, or alfalfa.

24. The method of any one of embodiments 19-21, wherein said plant cell is from a monocot.

25. The method of embodiment 24, wherein said dicot is selected from the group consisting of maize, wheat, rice, barley, sorghum, or rye.

26. The method of any one of embodiments 19-25, wherein the plant cell further comprises at least one polypeptide imparting tolerance to a herbicide.

27. The plant, plant cell, or seed of embodiment 26, wherein said at least one polypeptide imparting tolerance to a herbicide comprises:
    (a) a sulfonylurea-tolerant acetolactate synthase;
    (b) an imidazolinone-tolerant acetolactate synthase;
    (c) a glyphosate-tolerant 5-enolpyruvylshikimate-3-phosphate synthase;
    (d) a glyphosate-tolerant glyphosate oxido-reductase;
    (e) a glyphosate-N-acetyltransferase;
    (f) a phosphinothricin acetyl transferase;
    (g) a protoporphyrinogen oxidase.
    (h) an auxin enzyme or receptor;
    (i) a P450 polypeptide; or,
    (j) an acetyl coenzyme A carboxylase (ACCase).

28. An expression cassette comprising a nucleic acid molecule operably linked to a heterologous promoter, wherein said heterologous promoter drives expression in a plant and wherein said nucleic acid molecule is selected from the group consisting of:
    a) a nucleic acid molecule comprising the nucleotide sequence of SEQ ID NO: 60;
    b) a nucleic acid molecule comprising a nucleotide sequence having at least 90% sequence identity to the nucleotide sequence of SEQ ID NO: 60, wherein said nucleotide sequence encodes a polypeptide that has HPPD activity and is transported into the chloroplast;
    c) a nucleic acid molecule that encodes a polypeptide comprising the amino acid sequence of SEQ ID NO: 57; and,
    d) a nucleic acid molecule that encodes a polypeptide comprising an amino acid sequence having at least 90% sequence identity to the amino acid sequence of SEQ ID NO: 57, wherein said nucleotide sequence encodes a polypeptide that has HPPD activity and is transported into the chloroplast; and,
    e) a complement of any of a)-d).

29. A plant cell comprising at least one expression cassette of embodiment 28.

30. The plant cell of embodiment 29, wherein said plant cell is a monocot.

31. The plant cell of embodiment 30, wherein said monocot is maize, wheat, rice, barley, sorghum, or rye.

32. The plant cell of embodiment 30, wherein said plant is from a dicot.

33. The plant cell of embodiment 32, wherein said dicot is soybean, Brassica, sunflower, cotton, or alfalfa.

34. A plant comprising at least one plant cell of any one of embodiments 29-33.

35. A transgenic seed produced by the plant of embodiment 34, wherein the seed comprises said expression cassette.

36. An isolated polypeptide selected from the group consisting of:
   a) a polypeptide comprising the amino acid sequence of SEQ ID NO:57; or,
   b) a polypeptide comprising an amino acid sequence having at least 90% sequence identity to the amino acid sequence of SEQ ID NO:57, wherein said polypeptide has HPPD activity and is transported into the chloroplast of a plant cell.

37. The plant, plant cell, or seed of any one of embodiments 29-35, wherein the plant, plant cell, or seed further comprises at least one polypeptide imparting tolerance to an additional herbicide.

38. The plant, plant cell, or seed of embodiment 37, wherein said at least one polypeptide imparting tolerance to an additional herbicide comprises:
   (a) a sulfonylurea-tolerant acetolactate synthase;
   (b) an imidazolinone-tolerant acetolactate synthase;
   (c) a glyphosate-tolerant 5-enolpyruvylshikimate-3-phosphate synthase;
   (d) a glyphosate-tolerant glyphosate oxido-reductase;
   (e) a glyphosate-N-acetyltransferase;
   (f) a phosphinothricin acetyl transferase;
   (g) a protoporphyrinogen oxidase.
   (h) an auxin enzyme or receptor;
   (i) a P450 polypeptide; or,
   (j) an acetyl coenzyme A carboxylase (ACCase).

39. The plant, plant cell, or seed of embodiment 37, wherein said at least one polypeptide imparting tolerance to an additional herbicide comprises a high resistance allele of acetolactate synthase (HRA) and/or a glyphosate-N-acetyltransferase polypeptide.

EXPERIMENTAL

Example 1

Maize HPPD has a Chloroplast Targeting Sequence

Bioinformatic Analysis of Maize HPPD:

Maize HPPD proteins are not predicted to have a chloroplast targeting peptide N-terminal sequence by ProtComp 6.1 (http://linux1.softberry.com/berry.phtml), a widely used program for detecting organellar targeting sequences. ProtComp 6.1 indicates a cytosolic location of maize HPPD. The results returned by the search are as follows:
   Significant similarity in Location: Cytoplasmic
   Cytoplasmic score=14470
   Chloroplastic score=1.4
   Similarly, WoLF PSORT (Horton et al. (2007) NAR 35:W585-W587) and TargetP (Emanuelsson et al., (2000) J. Mol. Biol. 300:1005-1016) predict a cytosolic location of the HPPD protein. Protein Prowler (Hawkins and Boden (2006) J>Bioinf. Comp. Bio. 4:1-18) predicts either a mitochondrial (0.34) or chloroplast (0.39) location and Multiloc (Hoglund et. al. (2006) Bioinformatics 22:1158-1165) predicts an extracellular (0.74) localization with the first 50 amino acids of maize HPPD but a chloroplast localization (0.97) for the full maize HPPD sequence (SEQ ID NO 10). However, MultiLoc fails to predict a CTP function for the first N-terminal 50 amino acids of maize HPPD, suggesting that additional sequences may be important for full function.

Evaluation of the Glycine max HPPD protein (SEQ ID NO: 23) gave similarly variable results with the various prediction programs with predictions of peroxisomal, cytoplasmic, extracellular and chloroplast localization.

Example 2

Activity of Truncated Forms of Maize HPPD

Organellar targeting sequences are usually cleaved after the peptide enters the organelle. Previous investigators (Fritze I et al. (2004) Plant Physiology 134:1388-1400; Yang C et al. (2004) Biochemistry 43: 10414-10423) have shown that native mature maize HPPD begins at either ala17 or ala23. Variants of the wild-type maize HPPD protein coding region were created with various lengths of the amino terminus removed. The sequences were expressed in E. coli and tested for activity and stability. In each case a methionine start codon was added to the truncated sequence. Proteins were designated by the position of their N-terminal amino acid (all alanines) as in SEQ ID NO: 9. All N-terminal truncated proteins retained the HPPD activity. Differences in the measured $k_{cat}$ may not be significantly different as only a single measurement was taken for this experiment. Assaying HPPD activity was carried out as described in Example 1 of Provisional Application 61/401,456, filed Aug. 13, 2010, Compositions and Methods Comprising Sequences having Hydroxyphenylpyruvate Dioxygenase (HPPD) Activity, herein incorporated by reference in it entirety.

TABLE 1a

Activity of N-terminal truncated-variants of maize wild-type HPPD.

| Truncation | kcat, min−1 |
|---|---|
| Maize wt | 166 |
| Ala12 | 230 |
| Ala15 | 177 |
| Ala17 | 180 |
| Ala20 | 128 |
| Ala23 | 184 |

Replicated data with two shuffled variants clearly showed that when the proteins were truncated such that their second amino acid (after the N-terminal methionine) is ala20, no significant differences in kinetic parameters were found.

TABLE 1b

Kinetic parameters of variants truncated to ala20

|  | Km, mM | kcat, min−1 | kcat/Km |
|---|---|---|---|
| Full-length var A | 6.61 ± 0.84 | 247 ± 47.1 | 37.2 ± 2.39 |
| Truncated var. A | 6.86 ± 0.37 | 206 ± 20.5 | 30.2 ± 4.64 |
| Full-length var. B | 11.80 ± 0.99 | 106 ± 12.4 | 9.00 ± 0.29 |
| Truncated var. B | 11.38 ± 0.96 | 93.3 ± 5.41 | 8.22 ± 0.36 |

To test stability, the variants were heated at various temperatures in the range of 20° C. to 54° C. for 30 minutes. The remaining activity was determined by the coupled assay described in Example 1 of Provisional Application 61/401, 456, filed Aug. 13, 2010, Compositions and Methods Comprising Sequences having Hydroxyphenylpyruvate Dioxygenase (HPPD) Activity, herein incorporated by reference in it entirety. All variants were stable at 20° C., but activity declined with incubation temperatures over 30° C. to nearly nil at 54° C. There were no differences in stability among wild-type and all truncated variants. Thus, maize HPPD does not require the N-terminal region of the protein for full enzymatic function in vitro.

Example 3

The N-Terminus of Maize HPPD Fused to DsRed is Targeted to Chloroplasts when Transiently Expressed in Maize Leaf A vector was constructed in which the portion of the maize HPPD (SEQ ID NO: 9) gene coding for the N-terminal 50 amino acids was fused to the gene coding for *Discosoma* sp. red fluorescence protein 2 (DsRed2) and inserted into a binary expression vector under control of the maize Rubisco activase promoter (Liu et al. (1996) *Plant Physiol.* 112(1): 43-51) and terminated with the *Solanum tuberosum* proteinase inhibitor II (pinII) terminator region (An et al. (1989) *Plant Cell* 1:115-122) with a hygromycin selection cassette. Both genes are between left and right border sequences from *Agrobacterium*.

A positive control vector was identical to the vector having the N-terminal 50 amino acids of maize HPPD described above except that the HPPD CTP was removed and the DsRed2 insert was fused to the chloroplast targeting peptide of *Zea maize* rubisco activase, while a negative control was DsRed2 with no targeting sequence. The plasmids were transformed into *Agrobacterium tumefaciens* AGL-1 and Agro-infiltration was used to introduce the constructs into plant cells. Agro-infiltration is a well described method (Kapila et. al. (1997) *Plant Science,* 122:101-108) of introducing an *Agrobacterium* cell suspension to plant cells of intact tissues so that reproducible infection and subsequent plant derived trans-gene expression may be measured or studied.

Leaves of 3-week old maize seedlings were infiltrated with the *Agrobacterium*, and examined by fluorescence microscopy two days later (Nikon Eclipse 80i, DsRed filter set). With the vector where DsRed2 was fused to Rubisco activase CTP, the red fluorescence was seen in discrete packets in a pattern resembling peri-nuclear chloroplasts, as expected. A similar pattern was seen when DsRed2 was fused to the N-terminal 50 amino acids of maize HPPD. Without targeting, fluorescence was diffuse with some concentration in the nucleus. See FIG. 5.

In another experiment, maize leaf tissue was co-bombarded with DNA from both the DsRed-containing test plasmids and a plasmid encoding untargeted cycle 3 green fluorescence protein (C3GFP) using the PDS-1000 He biolistic particle delivery system (Bio-Rad, Hercules Calif.). Initial examination was conducted at approximately 24 h post-bombardment with a Lumar fluorescence stereomicroscope (Carl Zeiss Inc., Thornwood N.Y.) equipped with both a UV-exciting (Zeiss Set 01) and red-emitting (Zeiss Set 43 HE) filter set to image the C3GFP and the DsRed2, respectively. C3GFP fluorescence was captured using a 488 nm argon laser for excitation and a 500-550 nm band pass emission filter. DsRed fluorescence was imaged using a 561 nm diode laser for excitation and a 575-615 nm band pass emission filter. Chlorophyll fluorescence was captured by combining 561 nm excitation and a 650-710 nm band pass emission filter.

The majority of maize leaf cells transformed were epidermal cells but because of the relatively low chlorophyll content of epidermal plastids it was difficult to verify plastid targeting of DsRed based on chlorophyll co-localization. Guard cell plastids, however, contained sufficient chlorophyll to be imaged via chlorophyll autofluorescence. Moderate to low-expressing guard cell pairs were chosen to illustrate plastid targeting (FIG. 6).

Transformation with vectors encoding RCA CTP-DsRed and the N-terminal 50 amino acids of maize HPPD fused to DsRed2 resulted in plastid targeting of the DsRed reporter. When fused to the known chloroplast targeting sequence of Rubisco activase, DsRed co-localized with chlorophyll autofluorescence (FIGS. 6B and 6C), whereas untargeted C3CFP showed no overlap with the Ds Red signal (FIG. 6A). Guard cell plastids could also be discerned by the exclusion of the C3GFP signal (FIGS. 6A, 6D, 6E, 6G and 6J) or the untargeted DsRed signal (FIGS. 6H and 6I). Plastid targeting of DsRed linked to the N-terminal 50 amino acids of maize HPPD was evident by a lack of overlap between the cytosolic C3GFP signal and the DsRed signal (Figs. F and G).

Example 4

0, 17, 20, 23, 30, 40 and 60 Amino Acid Fusions of *Zea mays* HPPD N-Terminal Region to Ds-Red and Visualization of Red Fluorescence in the Chloroplast Vectors are constructed in which the portion of the maize HPPD gene (SEQ ID NO: 10) coding for the N-terminal 0, 17, 20, 23, 30, 40 or 60 amino acids are fused to the gene coding for *Discosoma* sp. red fluorescence protein 2 (DsRed2) and inserted into a binary expression vector under control of the maize Rubisco activase promoter (Liu et al. (1996) *Plant Physiol.* 112(1): 43-51) and terminated with the *Solanum tuberosum* proteinase inhibitor II (pinII) terminator region (An et al. (1989) *Plant Cell* 1:115-122) with a hygromycin selection cassette. Both genes are between left and right border sequences from *Agrobacterium*.

A positive control vector is identical except that the insert was DsRed2 fused to the chloroplast targeting peptide of *Arabidopsis* rubisco activase, while a negative control is DsRed2 with no targeting sequence. The plasmids are transformed into *Agrobacterium tumefaciens* AGL-1 and Agro-infiltration used to introduce the constructs into plant cells. Agro-infiltration is a well described method (Kapila, et. al., (1997) *Plant Science,* 122:101-108) of introducing an *Agrobacterium* cell suspension to plant cells of intact tissues so that reproducible infection and subsequent plant derived trans-gene expression may be measured or studied.

Leaves of 3-week old maize seedlings are infiltrated with the *Agrobacterium*, and examined by fluorescence microscopy two days later (Nikon Eclipse 80i, DsRed filter set).

Example 5

Alignment of Monocot N-Terminal Regions to Show Similarity

FIG. 4 provides an N terminal alignment of monocot HPPD proteins with identities highlighted. The % identity table shows the relatedness of the fragments as shown. The proposed CTP activity is expected to be in the first 17-30 amino acids of each, although the sequences beyond the cleaved fragments may be important for localization. In view of the sequence of the monocot HPPD proteins, a consensus monocot HPPD chloroplast targeting peptide sequences was determined and provided in SEQ ID NO:1, where the * represents gaps in the alignment such that those position may be absent in a variant of the consensus sequence SEQ ID NO 2.

```
                                                                    (SEQ ID NO: 1)
MPPTP(T/A)(T/P/A)(T/P/A)(A/T)(G/T/A)(G/T/A)(G/A/*)(A/*)(G/V/*)(A/S/V)AA(A/S)

(A/S/V)(T/A)(P/G/*)E(H/N/Q)A(A/G/R)(F/P/R)(R/*)(L/*)(V/*)(G/S/*)(H/F/*)(R/H/P)

(R/N)(F/M/V)VR(F/A/V)NPRSDRF(H/Q/P)(T/A/V)L(A/S)FHHVE
```

A synthetic consensus monocot CTP from HPPD is further provided comprising the sequence set forth in SEQ ID NO: 2.

```
                                                   (SEQ ID NO: 2)
MPPTPTTAAATGAGAAAAVTPEHAAFRLVGHRRFVRFNPRSDRFHTLAF
HHVE.
```

Example 6

Fusion of Other Monocot N-Terminal Regions to Ds-Red and Visualization of Red Fluorescence in Maize Chloroplasts Vectors are constructed in which N-terminal fragments (any amino acids from 1-20 or 1-60 or any region in between) of monocot HPPD proteins (SEQ ID NOS 10, 11, 12, 13, 14, 54) and the synthetic consensus peptide of SEQ ID NO: 2 is fused to the gene coding for *Discosoma* sp. red fluorescence protein 2 (DsRed2) and inserted into a binary expression vector under control of the maize Rubisco activase promoter (Liu et al. (1996) *Plant Physiol.* 112(1): 43-51) and terminated with the *Solanum tuberosum* proteinase inhibitor II (pinII) terminator region (An et al. (1989) *Plant Cell* 1:115-122) with a hygromycin selection cassette. Both genes are between left and right border sequences from *Agrobacterium*.

A positive control vector is identical except that the insert was DsRed2 fused to the chloroplast targeting peptide of *Arabidopsis* rubisco activase, while a negative control is DsRed2 with no targeting sequence. The plasmids are transformed into *Agrobacterium tumefaciens* AGL-1 and Agro-infiltration used to introduce the constructs into plant cells. Agro-infiltration is a well described method (Kapila et. al. (1997) *Plant Science*, 122:101-108) of introducing an *Agrobacterium* cell suspension to plant cells of intact tissues so that reproducible infection and subsequent plant derived trans-gene expression may be measured or studied.

Leaves of 3-week old maize seedlings are infiltrated with the *Agrobacterium*, and examined by fluorescence microscopy two days later (Nikon Eclipse 80i, DsRed filter set).

Example 7

Recovery of Mature HPPD Protein from Maize Cells and Sequence of N-Terminus Showing the Cleavage Site after CTP Removal Purified native HPPD was obtained from maize leaves by affinity chromatography on a column of immobilized anti-maize HPPD antibodies. Serum containing anti-maize HPPD antibodies was raised in rabbits antigenized with recombinant maize wild type 6x-his-HPPD produced in *E coli* and purified by nickel chelate affinity chromatography. The serum was passed through Protein A Ceramin Hyper DF to adsorb the IgG fraction. After washing, IgG was eluted with citrate buffer, pH 2.55, with a yield of 50 mg of IgG per gram of serum protein. Ten mg of IgG protein were subjected to the manufacturer's linkage protocol for Affi-Gel Hz (Bio-Rad), which resulted in the capture of 2 mg of IgG, 20% of which was anti-maize HPPD.

Maize leaf tissue was frozen in liquid nitrogen and pulverized in a mortar cooled with liquid nitrogen. The powder was mixed with 5 ml of 50 mM potassium phosphate, pH 7.3, 100 mM KCl, 10% ethylene glycol and 2 mM DTT. When thawed, the debris was removed by screening and the liquid centrifuged at 14,000×g, 15 min. The soluble protein fraction was desalted by passage through a gel-filtration column equilibrated with 50 mM potassium phosphate, 100 mM KCl, 10% ethylene glycol and the solution passed through the Affigel-anti-HPPD column. After extensive washing, pure native maize HPPD was eluted with 2 bed volumes of 0.5 M formic acid, then immediately neutralized. The preparation was subjected to Edman sequencing to determine the N-terminal sequence of mature maize HPPD protein.

Example 8

Function of Maize HPPD N-Terminal Sequence in Localizing Proteins to the Chloroplasts of Dicot Plant Cells A vector is constructed in which the portion of the maize HPPD gene coding for the N-terminal 50 amino acids was fused to the gene coding for *Discosoma* sp. red fluorescence protein 2 (DsRed2) and inserted into a binary expression vector under control of the *Arabidopsis* Ubiquitin 10 promoter (Norris, et al. (1993) *Plant Mol. Biol.* 21, 895-906) and terminated with the *Solanum tuberosum* proteinase inhibitor II (pinII) terminator region (An et al. (1989) *Plant Cell* 1:115-122) with a hygromycin selection cassette. Both genes are between left and right border sequences from *Agrobacterium*.

Leaf tissue of bush bean (common bean, *Phaseolus vulgaris*), are agro-infiltrated with *Agrobacterium* bacterial cell cultures of test and control strains. Infiltrated leaf samples are derived from plants of uniform developmental stage grown under the same conditions. Protoplasts are made from the infiltrated leaves 2-3 days after infection. Protoplasts can be isolated with proper osmoticum and enzyme digestion as by the method described by Rao and Prakash (1995) *J. Biosci.* 20:645-655. Protoplasts are examined using fluorescence microscopy using a Nikon Eclipse 80i, DsRed filter set to localize the N-terminal fusion proteins.

Example 9

Localization of Proteins Fused to the N-Terminal Fragments of Dicot HPPD Proteins Vectors are constructed in which N-terminal fragments (20-60 amino acids) of dicot plant HPPD proteins (SEQ ID NOS 15-24) are fused to the gene coding for *Discosoma* sp. red fluorescence protein 2 (DsRed2) and inserted into a binary expression vector under control of the maize Rubisco activase promoter (Liu et al. (1996) *Plant Physiol.* 112(1): 43-51) or the *Arabidopsis* Ubiquitin 10 promoter (Norris et al. (1993) *Plant Mol. Biol.* 21, 895-906) and terminated with the

*Solanum tuberosum* proteinase inhibitor II (pinII) terminator region (An et al. (1989) *Plant Cell* 1:115-122) with a hygromycin selection cassette. Both genes are between left and right border sequences from *Agrobacterium*. Such vectors can be used for either stable or transient gene expression in plant cells.

A positive control vector is identical except that the insert was DsRed2 fused to the chloroplast targeting peptide of *Arabidopsis* rubisco activase, while a negative control is DsRed2 with no targeting sequence. The plasmids are transformed into *Agrobacterium tumefaciens* AGL-1 and Agro-infiltration used to introduce the constructs into plant cells. Agro-infiltration is a well described method (Kapila, et. al., (1997) *Plant Science*, 122:101-108) of introducing an *Agrobacterium* cell suspension to plant cells of intact tissues so that reproducible infection and subsequent plant derived trans-gene expression may be measured or studied.

Leaves of 3-week old maize seedlings are infiltrated with the *Agrobacterium*, and examined by fluorescence microscopy two days later (Nikon Eclipse 80i, DsRed filter set).

Leaf tissue of bush bean (common bean, *Phaseolus vulgaris*), are agro-infiltrated with *Agrobacterium* bacterial cell cultures of test and control strains. Infiltrated leaf samples are derived from plants of uniform developmental stage grown under the same conditions. Protoplasts are made from the infiltrated leaves 2-3 days after infection. Protoplasts can be isolated with proper osmoticum and enzyme digestion as by the method described by Rao and Prakash (1995) *J. Biosci*. 20:645-655. Protoplasts are examined using fluorescence microscopy using a Nikon Eclipse 80i, DsRed filter set to localize the N-terminal fusion proteins.

Example 10

Transformation and Regeneration of Transgenic Maize Plants

Immature maize embryos from greenhouse donor plants are bombarded with a plasmid containing an expression cassette comprising a CTP-encoding sequence disclosed herein operably linked to a polynucleotide encoding a polypeptide of interest operably linked to a promoter and the selectable marker gene PAT (Wohlleben et al. (1988) *Gene* 70:25-37), which confers resistance to the herbicide Bialaphos. Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5 cm target zone in preparation for bombardment.

A plasmid vector comprising the CTP-encoding sequence operably linked to a polynucleotide encoding a polypeptide of interest is made. This plasmid DNA plus plasmid DNA containing a PAT selectable marker is precipitated onto 1.1 µm (average diameter) tungsten pellets using a $CaCl_2$ precipitation procedure as follows: 100 µl prepared tungsten particles in water; 10 µl (1 µg) DNA in Tris EDTA buffer (1 µg total DNA); 100 µl 2.5 M $CaCl_2$; and, 10 µl 0.1 M spermidine.

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 µl 100% ethanol is added to the final tungsten particle pellet. For particle gun bombardment, the tungsten/DNA particles are briefly sonicated and 10 µl spotted onto the center of each macrocarrier and allowed to dry about 2 minutes before bombardment.

The sample plates are bombarded at level #4 in a particle gun. All samples receive a single shot at 650 PSI, with a total of ten aliquots taken from each tube of prepared particles/DNA.

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for the translocation of the polypeptide of interest to the chloroplast of the plant cell.

Bombardment medium (560Y) comprises 4.0 g/l N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000×SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l bacto-agar (added after bringing to volume with polished D-I $H_2O$), sterilized and cooled to 60° C.

Bombardment and Culture Media

Bombardment medium (560Y) comprises 4.0 g/l N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/l 2,4-D, and 2.88 g/l L-proline (brought to volume with D-I H$_2$O following adjustment to pH 5.8 with KOH); 2.0 g/l Gelrite (added after bringing to volume with D-I H$_2$O); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000×SIGMA-1511), 0.5 mg/l thiamine HCl, 30.0 g/l sucrose, and 2.0 mg/l 2,4-D (brought to volume with D-I H$_2$O following adjustment to pH 5.8 with KOH); 3.0 g/l Gelrite (added after bringing to volume with D-I H$_2$O); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I H$_2$O) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I H$_2$O after adjusting to pH 5.6); 3.0 g/l Gelrite (added after bringing to volume with D-I H$_2$O); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I H$_2$O), 0.1 g/l myo-inositol, and 40.0 g/l sucrose (brought to volume with polished D-I H$_2$O after adjusting pH to 5.6); and 6 g/l bacto-agar (added after bringing to volume with polished D-I H$_2$O), sterilized and cooled to 60° C.

Example 11

*Agrobacterium*-Mediated Transformation of Maize Plants

For *Agrobacterium*-mediated transformation of maize with a CTP-encoding sequence operably linked to a polynucleotide encoding a polypeptide of interest, the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of *Agrobacterium*, where the bacteria are capable of transferring a CTP-encoding sequence operably linked to a polynucleotide encoding a polypeptide of interest to at least one cell of at least one of the immature embryos (step 1: the infection step). In this step the immature embryos are immersed in an *Agrobacterium* suspension for the initiation of inoculation. The embryos are co-cultured for a time with the *Agrobacterium* (step 2: the co-cultivation step). The immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). The immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium are cultured on solid medium to regenerate the plants.

Example 12

Soybean Embryo Stable Transformation

Soybean embryos are transformed with an expression cassette comprising a CTP-encoding sequence disclosed herein operably linked to a polynucleotide encoding a polypeptide of interest operably linked to a promoter and the selectable marker gene. Transformation is performed as follows.

Soybean embryogenic suspension cultures (cv. Jack) are maintained in 35 ml liquid medium SB196 (see recipes below) on rotary shaker, 150 rpm, 26° C. with cool white fluorescent lights on 16:8 hr day/night photoperiod at light intensity of 60-85 µE/m2/s. Cultures are subcultured every 7 days to two weeks by inoculating approximately 35 mg of tissue into 35 ml of fresh liquid SB196 (the preferred subculture interval is every 7 days).

Soybean embryogenic suspension cultures are transformed with the plasmids and DNA fragments by the method of particle gun bombardment (Klein et al. (1987) *Nature*, 327:70).

Soybean Embryogenic Suspension Culture Initiation

Soybean cultures are initiated twice each month with 5-7 days between each initiation.

Pods with immature seeds from available soybean plants 45-55 days after planting are picked, removed from their shells and placed into a sterilized magenta box. The soybean seeds are sterilized by shaking them for 15 minutes in a 5% Clorox solution with 1 drop of ivory soap (95 ml of autoclaved distilled water plus 5 ml Clorox and 1 drop of soap). Mix well. Seeds are rinsed using 2 1-liter bottles of sterile distilled water and those less than 4 mm are placed on individual microscope slides. The small end of the seed are cut and the cotyledons pressed out of the seed coat. Cotyledons are transferred to plates containing SB1 medium (25-30 cotyledons per plate). Plates are wrapped with fiber tape and stored for 8 weeks. After this time secondary embryos are cut and placed into SB196 liquid media for 7 days.

Preparation of DNA for Bombardment

Either an intact plasmid or a DNA plasmid fragment containing the genes of interest and the selectable marker gene are used for bombardment. Plasmid DNA for bombardment are routinely prepared and purified using the method described in the Promega™ Protocols and Applications Guide, Second Edition (page 106). Fragments of the plasmids carrying a CTP-encoding sequence operably linked to a polynucleotide encoding a polypeptide of interest are obtained by gel isolation of double digested plasmids. In each case, 100 ug of plasmid DNA is digested in 0.5 ml of the specific enzyme mix that is appropriate for the plasmid of interest. The resulting DNA fragments are separated by gel electrophoresis on 1% SeaPlaque GTG agarose (BioWhitaker Molecular Applications) and the DNA fragments containing a CTP-encoding sequence operably linked to a polynucleotide encoding a polypeptide of interest are cut from the agarose gel. DNA is purified from the agarose using the GELase digesting enzyme following the manufacturer's protocol.

A 50 µl aliquot of sterile distilled water containing 3 mg of gold particles (3 mg gold) is added to 5 µl of a 1 µg/0 DNA solution (either intact plasmid or DNA fragment prepared as described above), 50 µl 2.5M CaCl$_2$ and 20 µl of 0.1 M spermidine. The mixture is shaken 3 min on level 3 of a vortex shaker and spun for 10 sec in a bench microfuge. After a wash with 400 µl 100% ethanol the pellet is suspended by sonication in 40 µl of 100% ethanol. Five µl of DNA suspension is dispensed to each flying disk of the Biolistic PDS1000/HE instrument disk. Each 5 µl aliquot contains approximately 0.375 mg gold per bombardment (i.e. per disk).

Tissue Preparation and Bombardment with DNA

Approximately 150-200 mg of 7 day old embryonic suspension cultures are placed in an empty, sterile 60×15 mm petri dish and the dish covered with plastic mesh. Tissue is bombarded 1 or 2 shots per plate with membrane rupture pressure set at 1100 PSI and the chamber evacuated to a vacuum of 27-28 inches of mercury. Tissue is placed approximately 3.5 inches from the retaining/stopping screen.

Selection of Transformed Embryos

Transformed embryos were selected either using hygromycin (when the hygromycin phosphotransferase, HPT, gene was used as the selectable marker) or chlorsulfuron (when the acetolactate synthase, ALS, gene was used as the selectable marker).

Hygromycin (HPT) Selection

Following bombardment, the tissue is placed into fresh SB196 media and cultured as described above. Six days post-bombardment, the SB196 is exchanged with fresh SB196 containing a selection agent of 30 mg/L hygromycin. The selection media is refreshed weekly. Four to six weeks post selection, green, transformed tissue may be observed growing from untransformed, necrotic embryogenic clusters. Isolated, green tissue is removed and inoculated into multiwell plates to generate new, clonally propagated, transformed embryogenic suspension cultures.

Chlorsulfuron (ALS) Selection

Following bombardment, the tissue is divided between 2 flasks with fresh SB196 media and cultured as described above. Six to seven days post-bombardment, the SB196 is exchanged with fresh SB196 containing selection agent of 100 ng/ml Chlorsulfuron. The selection media is refreshed weekly. Four to six weeks post selection, green, transformed tissue may be observed growing from untransformed, necrotic embryogenic clusters. Isolated, green tissue is removed and inoculated into multiwell plates containing SB196 to generate new, clonally propagated, transformed embryogenic suspension cultures.

Regeneration of Soybean Somatic Embryos into Plants

In order to obtain whole plants from embryogenic suspension cultures, the tissue must be regenerated.

Embryo Maturation

Embryos are cultured for 4-6 weeks at 26° C. in SB196 under cool white fluorescent (Phillips cool white Econowatt F40/CW/RS/EW) and Agro (Phillips F40 Agro) bulbs (40 watt) on a 16:8 hr photoperiod with light intensity of 90-120 uE/m2s. After this time embryo clusters are removed to a solid agar media, SB166, for 1-2 weeks. Clusters are then subcultured to medium SB103 for 3 weeks. During this period, individual embryos can be removed from the clusters and screened for the presence of the polypeptide of interest in the chloroplast. It should be noted that any detectable phenotype, resulting from the expression of the genes of interest, could be screened at this stage.

Embryo Desiccation and Germination

Matured individual embryos are desiccated by placing them into an empty, small petri dish (35×10 mm) for approximately 4-7 days. The plates are sealed with fiber tape (creating a small humidity chamber). Desiccated embryos are planted into SB71-4 medium where they were left to germinate under the same culture conditions described above. Germinated plantlets are removed from germination medium and rinsed thoroughly with water and then planted in Redi-Earth in 24-cell pack tray, covered with clear plastic dome. After 2 weeks the dome is removed and plants hardened off for a further week. If plantlets looked hardy they are transplanted to 10" pot of Redi-Earth with up to 3 plantlets per pot. After 10 to 16 weeks, mature seeds are harvested, chipped and analyzed for proteins.

Media Recipes

| SB 196 - FN Lite liquid proliferation medium (per liter) - | |
|---|---|
| MS FeEDTA - 100x Stock 1 | 10 ml |
| MS Sulfate - 100x Stock 2 | 10 ml |
| FN Lite Halides - 100x Stock 3 | 10 ml |
| FN Lite P,B,Mo - 100x Stock 4 | 10 ml |
| B5 vitamins (1 ml/L) | 1.0 ml |
| 2,4-D (10 mg/L final concentration) | 1.0 ml |
| $KNO_3$ | 2.83 gm |
| $(NH4)2 SO 4$ | 0.463 gm |
| Asparagine | 1.0 gm |
| Sucrose (1%) | 10 gm |
| pH 5.8 | |

FN Lite Stock Solutions

| Stock # | | 1000 ml | 500 ml |
|---|---|---|---|
| 1 | MS Fe EDTA 100x Stock | | |
| | $Na_2$ EDTA* | 3.724 g | 1.862 g |
| | $FeSO_4$—$7H_2O$ | 2.784 g | 1.392 g |
| 2 | MS Sulfate 100x stock | | |
| | $MgSO_4$—$7H_2O$ | 37.0 g | 18.5 g |
| | $MnSO_4$—$H_2O$ | 1.69 g | 0.845 g |
| | $ZnSO_4$—$7H_2O$ | 0.86 g | 0.43 g |
| | $CuSO_4$—$5H_2O$ | 0.0025 g | 0.00125 g |
| 3 | FN Lite Halides 100x Stock | | |
| | $CaCl_2$—$2H_2O$ | 30.0 g | 15.0 g |
| | KI | 0.083 g | 0.0715 g |
| | $CoCl_2$—$6H_2O$ | 0.0025 g | 0.00125 g |
| 4 | FN Lite P,B,Mo 100x Stock | | |
| | $KH_2PO_4$ | 18.5 g | 9.25 g |
| | $H_3BO_3$ | 0.62 g | 0.31 g |
| | $Na_2MoO_4$—$2H_2O$ | 0.025 g | 0.0125 g |

*Add first, dissolve in dark bottle while stirring

SB1 solid medium (per liter) comprises: 1 pkg. MS salts (Gibco/BRL-Cat#11117-066); 1 ml B5 vitamins 1000× stock; 31.5 g sucrose; 2 ml 2,4-D (20 mg/L final concentration); pH 5.7; and, 8 g TC agar.

SB 166 solid medium (per liter) comprises: 1 pkg. MS salts (Gibco/BRL-Cat#11117-066); 1 ml B5 vitamins 1000× stock; 60 g maltose; 750 mg MgCl2 hexahydrate; 5 g activated charcoal; pH 5.7; and, 2 g gelrite.

SB 103 solid medium (per liter) comprises: 1 pkg. MS salts (Gibco/BRL-Cat#11117-066); 1 ml B5 vitamins 1000× stock; 60 g maltose; 750 mg MgCl2 hexahydrate; pH 5.7; and, 2 g gelrite.

SB 71-4 solid medium (per liter) comprises: 1 bottle Gamborg's B5 salts w/sucrose (Gibco/BRL-Cat#21153-036); pH 5.7; and, 5 g TC agar.

2,4-D stock is obtained premade from Phytotech cat#D 295-concentration is 1 mg/ml.

B5 Vitamins Stock (per 100 ml) which is stored in aliquots at −20 C comprises: 10 g myo-inositol; 100 mg nicotinic acid; 100 mg pyridoxine HCl; and, 1 g thiamine. If the solution does not dissolve quickly enough, apply a low level of heat via the hot stir plate. Chlorsulfuron Stock comprises 1 mg/ml in 0.01 N Ammonium Hydroxide.

Example 13

*Glycine max* HPPD has a Chloroplast Targeting Sequence

The *G. max* HPPD protein has been previously annotated as a 449 amino acid protein with N-terminal sequence MPIP-MCNEIQ (SEQ ID NO:55) (See, U.S. Pat. No. 7,226,745 SEQ ID NO: 36) and as a 443 amino acid protein with N-terminal sequence MCNEIQAQAQ (SEQ ID NO: 56) (Genbank ABQ96868). Our analysis of *G. max* EST data revealed that an in-frame N-terminal extension of the previously annotated coding region exists, adding 41-amino acids to produce a 488 amino acid full-length HPPD protein (SEQ ID NO:57).

Bioinformatic and in-planta evaluation of the shorter *G. max* HPPD sequences did not reveal a chloroplast or other targeting sequence by prediction or by localization (see Example 1 and Example 9). The longer N-terminal region was able to direct a fluorescent marker protein to the chloroplast in dicot cells. See, Example 14 below.

Bioinformatic analysis of the full-length *G. max* HPPD (SEQ ID NO: 57) revealed that a chloroplast targeting function is predicted. ProtComp 9.0 (http://linux1.softberry.com) returned the highest score for a membrane bound chloroplast localization based on the first 24 amino acids. WoLF P SORT (http://wolfpsort.org) also predicts a chloroplast location. TargetP (http://www.cbs.dtu.dk/services/TargetP) however only suggests a chloroplast localization, giving a higher score to 'other'.

Example 14

Transient Expression of Gm HPPD-AcGFP Fusion Proteins

Numerous genes have been found to have two or more in-frame ATGs at the 5' end. For review, see Small et al. (1998) *Plant Molecular Biology* 38: 265-277. Many of such genes are known to have multiple transcription starts to enable the production of two proteins from the same gene. Often, the "long" protein contains plastid targeting signal at the N-terminal while the "short" protein does not. Appropriate distribution of the "long" and "short" protein variants between two subcellular compartments is desired for the respective protein function to be carried out normally. The soy HPPD gene described here falls into this class of genes. No other HPPD gene is known to share the same description.

Figure 8:
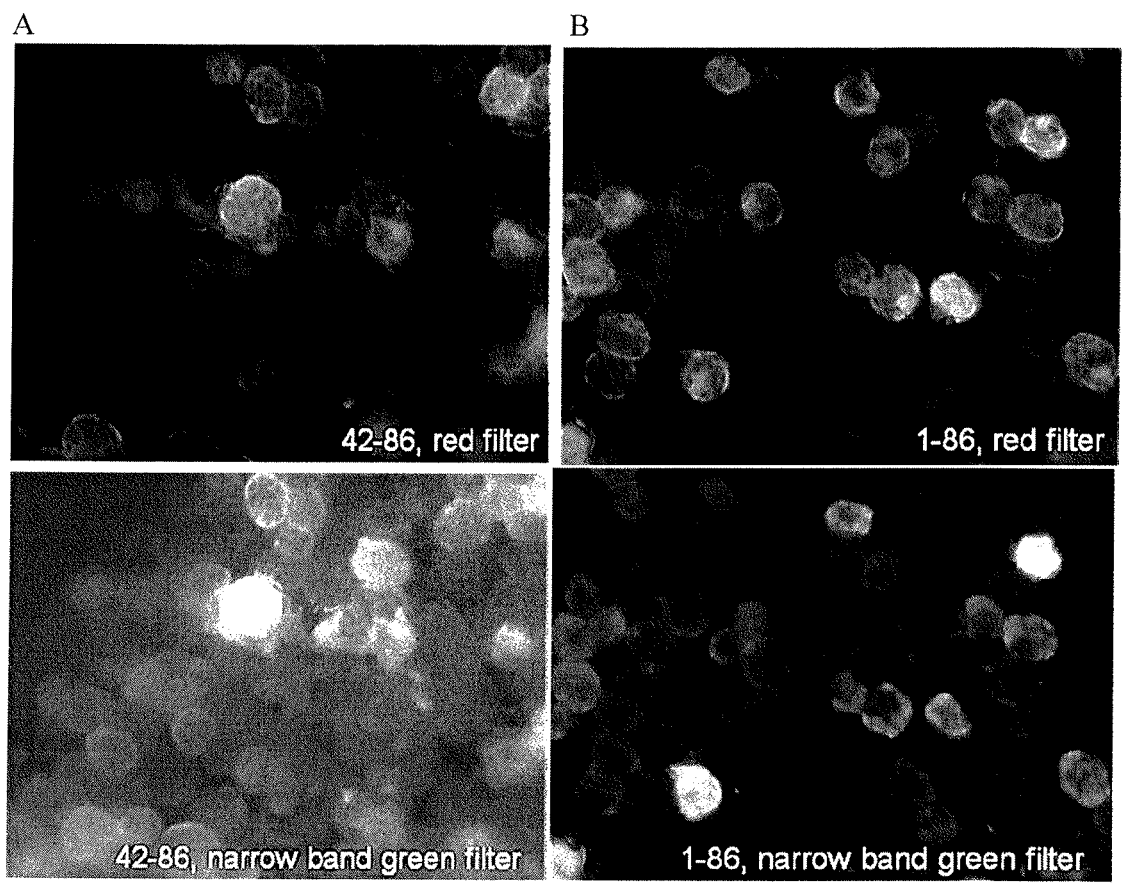
FIG. 8 shows transient expression of Gm HPPD-AcGFP fusion proteins in soy leaf cells. Epifluorescence micrographs of soy leaf sections infiltrated with both untargeted (cytoplasmic) DsRed2 and Gm-HPPD N terminus fusions to AcGFP. A and C. With both vectors red fluorescence is seen in the cytoplasm while plastids remain dark. B. When AcGFP is fused to Gm-HPPD amino acids 42-86 (from SEQ ID NO: 57), green fluorescence is seen in the cytoplasm and plastids remain dark. D. When AcGFP is fused to Gm HPPD amino acids 1-86 (from SEQ ID NO: 57), green fluorescence is clearly seen in plastids of infected cells.

Transient expression experiments indicate that the long HPPD protein (SEQ ID NO: 57) is imported to chloroplasts, while the short protein (SEQ ID NO: 59) remains in the cytosol. Plant expression cassettes were constructed fusing portions of the N terminus of Gm HPPD to an *Aequorea coerulescens* green fluorescent protein 1 (AcGFP1). One fusion contained amino acid residues 1-86 of the long Gm HPPD protein. Another contained residues 1-44 of the short HPPD protein (this corresponds to residues 42-86 of the long protein). These cassettes were incorporated into binary vectors which also contained an untargeted DsRed2 expression cassette and introduced into *A. tumefaciens* strain AGL 1 and then used to infect leaf discs of *G. max* as described in Example 3 of U.S. Utility application Ser. No. 13/209,017, now issued U.S. Pat. No. 8,993,837, entitled "Chimeric Promoter and Methods of Use", filed concurrently herewith and herein incorporated by reference in its entirety. As shown in FIG. 8, green fluorescence is clearly visible in the chloroplasts of infected cells when AcGFP is fused to amino acid residues 1-86 of Gm HPPD. When the fusion is made with residues 42-86, corresponding to the 44 N-terminus residues of the short protein, green fluorescence is visible only in the cytoplasm.

Example 15

The N-Terminal 0, 10, 20, 30, 40 or 50 Amino Acids of *Zea mays* HPPD Fused to Ds-Red; Visualization of Red Fluorescence in the *Z. Mays* Chloroplast Vectors were constructed in which the portion of the maize HPPD chloroplast targeting sequence (SEQ ID NO: 3) coding for the N-terminal 0, 10, 20, 30, 40 or 50 amino acids was fused to the gene coding for *Discosoma* sp. red fluorescence protein 2 (DsRed2) and inserted into a binary expression vector under control of the maize Rubisco activase promoter (Liu et al. (1996) *Plant Physiol.* 112(1): 43-51) and terminated with the *Solanum tuberosum* proteinase inhibitor II (pinII) terminator region (An et al. (1989) *Plant Cell* 1:115-122). The vector also contained an untargeted Zs Green cassette to provide cytoplasmic contrast and a kanamycin selection cassette. All three genes were between left and right border sequences of *Agrobacterium* T-DNA. A positive control vector was identical except that the insert was DsRed2 fused to the chloroplast targeting peptide of maize rubisco activase, while a negative control was DsRed2 with no targeting sequence. The plasmids were transformed into *Agrobacterium tumefaciens* AGL-1 and Agro-infiltration was used to introduce the constructs into plant cells. Agro-infiltration is a well described method (Kapila, et. al., (1997) *Plant Science*, 122:101-108) of introducing an *Agrobacterium* cell suspension to plant cells of intact tissues so that reproducible infection and subsequent plant derived trans-gene expression may be measured or studied. Leaves of 4-week old maize seedlings were infiltrated with the *Agrobacterium*, and examined by fluorescence microscopy four days later (Nikon Eclipse 80i, DsRed filter set).

Figure 9:
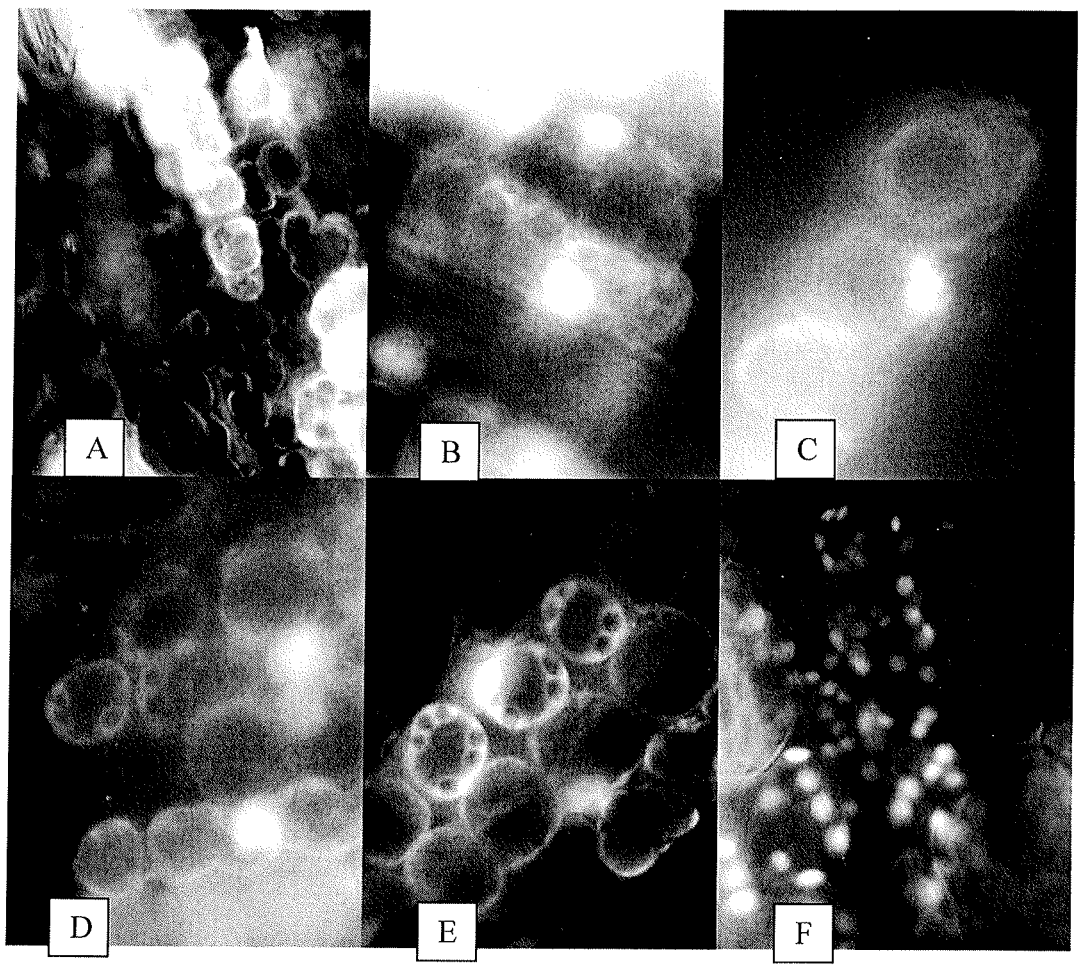
FIG. 9 shows that 50 amino acids of the maize HPPD N-terminus effectively targeted DsRed to plastids. N-terminal 0, 10, 20, 30, 40 or 50 amino acids of *Zea Mays* HPPD fused to Ds-Red. A-F: DsRed fluorescence micrographs A) 0aa, B) 10aa, C) 20aa, D) 30aa, E) 40aa F) 50aa.

Microscopy revealed that 50 amino acids of the maize HPPD N-terminus effectively targeted DsRed to plastids, but 40 amino acids or fewer failed to do so, with DsRed fluorescence visible only in the cytoplasm. See FIG. 9.

Example 16

Fusion of Other Monocot N-Terminal Regions to Ds-Red and Visualization of red fluorescence in maize and sorghum chloroplasts A vector was constructed in which the monocot HPPD N-terminal consensus sequence (53 amino acids SEQ ID NO: 2) was fused to the gene coding for DsRed2 and assayed as described in Example 4. Microscopy revealed that the 53 amino acid consensus sequence effectively targeted DsRed to maize plastids, as did the maize rubisco activase positive control, but the untargeted negative control failed to do so, with DsRed fluorescence visible only in the cytoplasm.

This vector incorporating the 53 amino acid monocot HPPD N terminal consensus sequence targeting DsRed, and the 0, 10, 20, 30, 40, and 50 amino acid maize HPPD N-terminal (SEQ ID NO: 3) vectors described in Example 15 were also tested by Agro-infiltration in sorghum leaves. The results matched those obtained in maize; ie the 53 amino acid consensus sequence and the 50 amino acid maize sequence efficiently targeted the DsRed reporter protein to plastids, but shorter fragments failed to do so with red fluorescence visible only in the cytoplasm.

A vector was constructed in which the *Oriza sativa* HPPD N-terminal sequence (SEQ ID NO: 5) was fused to the gene coding for DsRed2 and assayed as described in example 4. Microscopy revealed that the 53 amino acid rice N-terminal sequence effectively targeted DsRed to maize plastids, as did the maize rubisco activase positive control, and the untargeted negative control failed to do so, with DsRed fluorescence visible only in the cytoplasm.

Example 17

Figure 10:
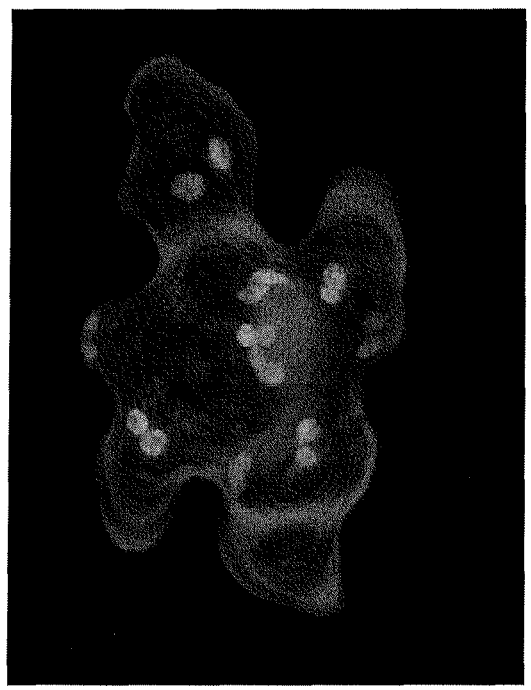
FIG. 10 shows AcGFP fluorescence confocal micrograph of soybean leaf epidermal cell transiently expressing AcGFP linked to 50 amino acids of maize HPPD N-terminus in both the chloroplasts and cytoplasm.

Function of Maize HPPD N-Terminal Sequence in Localizing Proteins to the Chloroplasts of Dicot Plant Cells The sequence encoding amino acids 1-50 of the maize HPPD protein (SEQ ID NO: 3) was fused to a gene encoding *Aequorea coerulescens* green fluorescent protein 1 (AcGFP1) and inserted into a binary expression vector under control of the *Arabidopsis* Ubiquitin 10 promoter (Norris et al. (1993) Plant Mol. Biol. 21, 895-906) and terminated with the *Glycine max* Kunitz trypsin inhibitor 3 terminator region (NCBI accession S45092). Both genes were between left and right border sequences from *Agrobacterium*. Such vectors can be used for either stable or transient gene expression in plant cells. A positive control vector was identical except that the AcGFP1 coding region was fused to the 6H1 synthetic chloroplast targeting peptide (U.S. Pat. No. 7,345,143 SEQ ID NO:1), while a negative control was AcGFP1 with no targeting sequence. The plasmids were transformed into *Agrobacterium tumefaciens* AGL-1 and Agro-infiltration used to introduce the constructs into plant cells. Agro-infiltration is a well described method (Kapila, et. al., (1997) *Plant Science,* 122:101-108) of introducing an *Agrobacterium* cell suspension to plant cells of intact tissues so that reproducible infection and subsequent plant derived transgene expression may be measured or studied. Infiltrated leaf samples were derived from plants of uniform developmental stage grown under the same conditions. Leaves of 4-week old *Nicotiana benthamiana,* 8-day old *Phaseolus vulgaris,* and 10-day old *Glycine max* seedlings were infiltrated with the *Agrobacterium*, and examined by fluorescence microscopy 4 and 5 days later (Nikon Eclipse 80i, DsRed filter set). The first 50 amino acids of maize HPPD were sufficient to drive chloroplast import of AcGFP in epidermal cells of *P. vulgaris,* although some green fluorescence remained in the cytoplasm. In *N. benthamiana* the AcGFP remained in the cytoplasm with none apparent in the chloroplasts. Results in *G. max* showed AcGFP in both plastids and cytoplasm. When similar constructs were introduced to soybean leaf epidermal cells and examined by confocal microscopy, green fluorescence was apparent in the cytosol and chloroplasts of transformed cells, with variable intensity in chloroplasts (see FIG. 10). This shows that the maize HPPD CTP is recognized in dicot plant cells.

Example 18

Localization of *Z. Mays* HPPD Protein in Stably Transformed Soybean Cells

Polyclonal antibodies were raised in rabbits against recombinant maize HPPD protein purified by nickel chelate affinity chromatography. Anti-HPPD antibodies were purified from serum by affinity chromatography on immobilized maize HPPD, and further purified by passage through a column of immobilized Rubisco, to remove a small fraction of antibodies that reacted with both HPPD and Rubisco. Leaf punches taken form stably transformed soybean plants expressing a gene encoding the maize HPPD protein (SEQ ID NO: 10) driven by an SCP1 synthetic promoter (U.S. Pat. No. 6,072,050) were fixed in 2% paraformaldehyde, 0.25% glutaraldehyde in 100 mM Na phosphate buffer, pH 7.0, for 3 hours at room temperature, dehydrated by passage through progressively higher concentrations of ethanol, embedded in LR White resin and cured at 55° C. for 48 hours. Sections (0.9 microns) were transferred onto Excell Adhesion glass microscope slides (Electron Microscopy Sciences). Immunolocalization was performed with the primary antibody being the double-purified anti-maize HPPD (1:200) and the secondary antibody goat anti-rabbit F(ab') conjugated with gold particles (Aurion ultrasmall gold). Gold labeling was followed by silver enhancement (Aurion R-GENT SE-EM). Sections were counterstained with 4% uranyl acetate (aqueous) followed by Reynold's lead citrate. Material was analyzed with a YAG detector for backscatter signal in a Hitachi 54800 scanning electron microscope. The clarity of the resulting images was enhanced by performing contrast inversion, using Adobe PhotoShop CS5.

Figure 11:
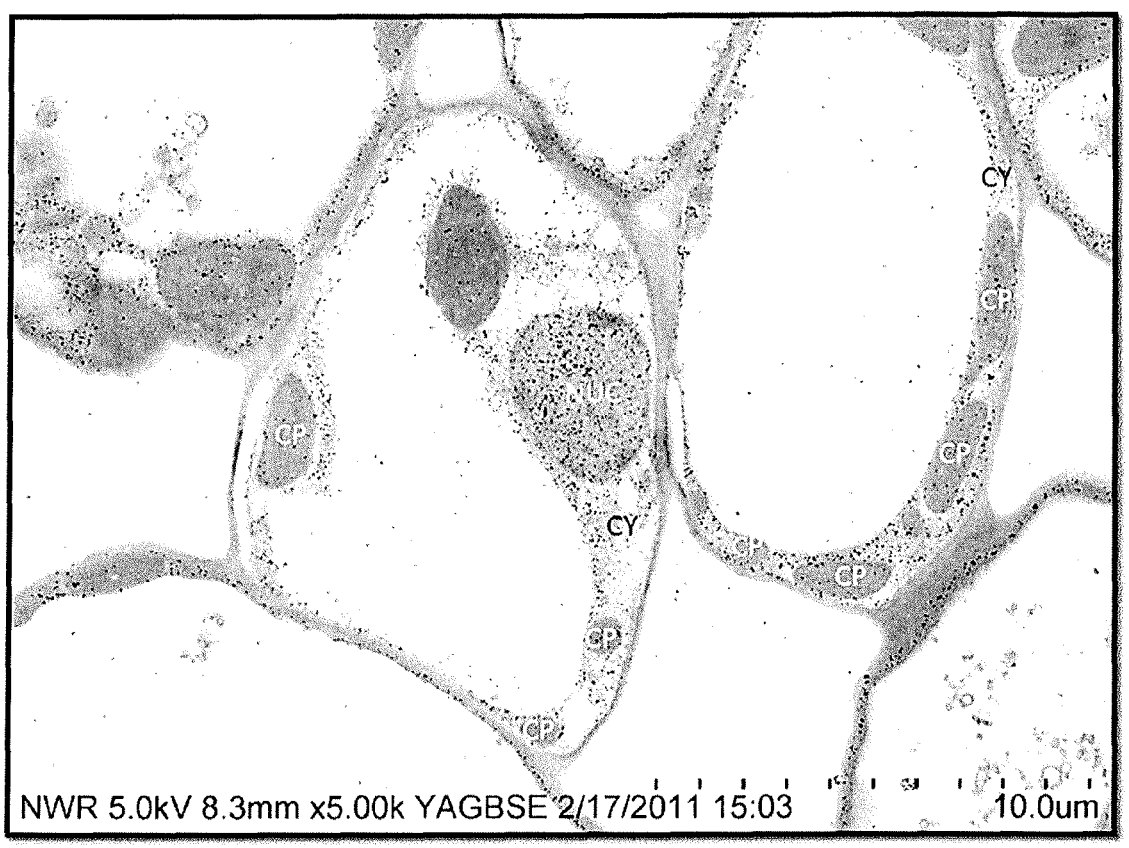
FIG. 11 shows a leaf section of stably transformed soybean leaf showing subcellular localization of *Z. mays* HPPD protein. CP: chloroplast; CY: cytosol; NUC: nucleus.

Gold labeling was observed mainly in cytosol and nuclei, but also in chloroplasts. See, FIG. 11. A small number of particles observed in other locations including voids are considered to be artifacts. This is consistent with transient expression experiments showing that the first 50 amino acids of the *Z. mays* HPPD N terminus did target a fluorescent reporter protein to the chloroplasts of *G. max* cells (see Example 17).

Example 19

*G. max* N-Terminus Targets Proteins to the Chloroplast in Maize Cells

Vectors were constructed in which a portion of the gene coding for the *G. max* HPPD N-terminus was fused to a gene encoding *Aequorea coerulescens* green fluorescent protein 1 (AcGFP1) and inserted into a binary expression vector under control of the *Arabidopsis* Ubiquitin 10 promoter (Norris et al. (1993) *Plant Mol. Biol.* 21, 895-906) and terminated with the *Glycine max* Kunitz trypsin inhibitor 3 terminator region (NCBI accession S45092). Both genes were between left and right border sequences from *Agrobacterium*. One fusion contained amino acid residues 1-86 of the long Gm HPPD protein (SEQ ID NO:57). Another contained residues 1-44 of the short HPPD protein (this corresponds to residues 42-86 of the long protein and SEQ ID NO:59).

A positive control vector was identical except that the AcGFP1 coding region was fused to the 6H1 synthetic chloroplast targeting peptide (U.S. Pat. No. 7,345,143), while a negative control was AcGFP1 with no targeting sequence. The plasmids were transformed into *Agrobacterium tumefaciens* AGL-1 and Agro-infiltration used to introduce the constructs into plant cells. Agro-infiltration is a well described method (Kapila et. al. (1997) *Plant Science,* 122:101-108) of introducing an *Agrobacterium* cell suspension to plant cells of intact tissues so that reproducible infection and subsequent plant trans-gene expression may be measured or studied.

Leaves of 4-week old maize seedlings were infiltrated with the *Agrobacterium*, and examined by fluorescence microscopy three days later (Nikon Eclipse 80i, Narrow band-pass GFP filter set). Transient expression indicated that the long *G. max* HPPD protein N-terminus (SEQ ID NO: 58) did target the marker protein to maize cell chloroplasts, while the short protein N-terminus (amino acids 1-44 of SEQ ID NO: 59)

delivered the protein to the cytosol. The dicot chloroplast targeting region of *G. max* HPPD is able to function in monocot cells.

TABLE 2

Summary of SEQ ID NOS

| SEQ ID NO | Description |
| --- | --- |
| 1 | Consensus Monocot CTP from HPPD |
| 2 | Synthetic consensus CTP from monocot HPPD |
| 3 | CTP of *Zea mays* HPPD |
| 4 | CTP of *sorghum bicolor* HPPD |
| 5 | CTP of *Oryza sativa* HPPD |
| 6 | CTP of *Triticum aestivum* HPPD |
| 7 | CTP of *Hordeum vulgare* HPPD |
| 8 | CTP of *Avena Sativa* HPPD |
| 9 | Full length *Zea mays* HPPD |
| 10 | Maize WT HPPD (from WO1997049816 SEQ ID NO: 11) |
| 11 | HPPD from *Hordeum vulgare* |
| 12 | HPPD from *Avena sativa* |
| 13 | HPPD from *Oryza sativa* |
| 14 | HPPD from *Triticum aestivum* |
| 15 | HPPD from *Daucus carota* |
| 16 | HPPD from *Solenosteman sautellarioides* |
| 17 | HPPD from *Picea sitchensis* |
| 18 | HPPD from *Abutilon theophrasti* |
| 19 | HPPD from *Arabidopsis thaliana* |
| 20 | HPPD from *Brassica rapa* |
| 21 | HPPD from *Coptis japonica* |
| 22 | HPPD from *Vitis vinifera* |
| 23 | HPPD from *Glycine max* |
| 24 | HPPD from *Medicago truncatula* |
| 26-53 | N-terminal regions of various HPPD polypeptides |
| 54 | HPPD from *Sorghum bicolor* |
| 55 | N-term amino acids of soy HPPD disclosed in U.S. Pat. No. 7,226,745 as SEQ ID NO: 36 |
| 56 | N-term amino acids of soy HPPD disclosed in Genbank ABQ96868 |
| 57 | Full length soybean HPPD |
| 58 | N-terminal region of SEQ ID NO: 57 comprising native soybean CTP |
| 59 | Soybean HPPD protein predicted from shorter transcript |
| 60 | Nucleotide sequence of the Full length soybean HPPD |

The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A chimeric polynucleotide comprising a nucleotide sequence encoding a chloroplast transit peptide operably linked to a heterologous polynucleotide encoding a polypeptide of interest, wherein the polypeptide of interest confers herbicide resistance, wherein said chloroplast transit peptide comprises
   an amino acid sequence having at least 90% sequence identity to SEQ ID NO: 58 and having at least 17 consecutive amino acids of SEQ ID NO: 58, wherein the 17 consecutive amino acids are from amino acids 1 to 41.

2. The chimeric polynucleotide of claim 1, wherein said chloroplast transit peptide comprises SEQ ID NO: 58.

3. The chimeric polynucleotide of claim 1, wherein said polypeptide of interest comprises a 4-hydroxphenylpyruvate dioxygenase (HPPD) polypeptide having HPPD activity.

4. A nucleic acid construct comprising the chimeric polynucleotide of claim 1.

5. The nucleic acid construct of claim 4, further comprising a promoter operably linked to said chimeric polynucleotide.

6. A cell comprising at least one chimeric polynucleotide of claim 1.

7. The cell of claim 6, wherein said cell is a plant cell.

8. The cell of claim 7, wherein said polynucleotide or nucleic acid construct is stably incorporated into the genome of said plant cell.

9. The cell of claim 7, wherein said plant cell is from a monocot.

10. The cell of claim 9, wherein said monocot is maize, wheat, rice, barley, sorghum, or rye.

11. The cell of claim 7, wherein said plant cell is from a dicot.

12. The cell of claim 11, wherein the dicot is soybean, *Brassica*, sunflower, cotton, or alfalfa.

13. A plant comprising at least one plant cell of claim 7.

14. A plant explant comprising at least one plant cell of claim 7.

15. A transgenic seed produced by the plant of claim 13, wherein said seed comprises said chimeric polynucleotide.

16. The plant cell of claim 7, wherein the plant cell further comprises at least one polypeptide imparting tolerance to a herbicide.

17. The plant cell of claim 16, wherein said at least one polypeptide imparting tolerance to a herbicide comprises:
   (a) a sulfonylurea-tolerant acetolactate synthase;
   (b) an imidazolinone-tolerant acetolactate synthase;
   (c) a glyphosate-tolerant 5-enolpyruvylshikimate-3-phosphate synthase;
   (d) a glyphosate-tolerant glyphosate oxido-reductase;
   (e) a glyphosate-N-acetyltransferase;
   (f) a phosphinothricin acetyl transferase;
   (g) a protoporphyrinogen oxidase;
   (h) an auxin enzyme or receptor;
   (i) a P450 polypeptide; or,
   (j) an acetyl coenzyme A carboxylase (ACCase).

18. A chimeric polypeptide encoded by the polynucleotide of claim 1.

19. A method of targeting a polypeptide of interest to a chloroplast comprising expressing a chimeric polynucleotide of claim 1 or the nucleic acid construct of claim 4 in a plant cell.

20. A method of targeting a polypeptide of interest to a chloroplast, comprising: introducing the chimeric polynucleotide of claim 1 or a nucleic acid construct comprising said chimeric polynucleotide in a plant cell and expressing said chimeric polynucleotide in the plant cell.

21. The method of claim 19, wherein said method further comprises regenerating a transgenic plant from said plant cell.

22. The method of claim 19, wherein said plant cell is from a dicot.

23. The method of claim 22, wherein said dicot is selected from the group consisting of soybean, *Brassica*, sunflower, cotton, and alfalfa.

24. The method of claim 19, wherein said plant cell is from a monocot.

25. The method of claim 24, wherein said dicot is selected from the group consisting of maize, wheat, rice, barley, sorghum, and rye.

26. The method of claim 19, wherein the plant cell further comprises at least one polypeptide imparting tolerance to a herbicide.

27. The method of claim 26, wherein said at least one polypeptide imparting tolerance to a herbicide comprises:
    (a) a sulfonylurea-tolerant acetolactate synthase;
    (b) an imidazolinone-tolerant acetolactate synthase;
    (c) a glyphosate-tolerant 5-enolpyruvylshikimate-3-phosphate synthase;
    (d) a glyphosate-tolerant glyphosate oxido-reductase;
    (e) a glyphosate-N-acetyltransferase;
    (f) a phosphinothricin acetyl transferase;
    (g) a protoporphyrinogen oxidase;
    (h) an auxin enzyme or receptor;
    (i) a P450 polypeptide; or,
    (j) an acetyl coenzyme A carboxylase (ACCase).

28. An expression cassette comprising a nucleic acid molecule operably linked to a heterologous promoter, wherein said heterologous promoter drives expression in a plant and wherein said nucleic acid molecule is selected from the group consisting of:
    a) a nucleic acid molecule comprising the nucleotide sequence of SEQ ID NO: 60;
    b) a nucleic acid molecule that encodes a polypeptide comprising the amino acid sequence of SEQ ID NO: 57;
    c) a nucleic acid molecule that encodes a polypeptide comprising an amino acid sequence having at least 90% sequence identity to the amino acid sequence of SEQ ID NO: 57, wherein said nucleotide sequence encodes a polypeptide that has HPPD activity and is transported into the chloroplast, wherein a polypeptide comprising an amino acid sequence having at least 90% sequence identity to the amino acid sequence of SEQ ID NO: 57 comprises 17 consecutive amino acids of SEQ ID NO:58, wherein the 17 consecutive amino acids are from amino acids 1 to 41; and,
    d) a full length complement of any of a)-c).

29. A plant cell comprising at least one expression cassette of claim 28.

30. The plant cell of claim 29, wherein said plant cell is a monocot.

31. The plant cell of claim 30, wherein said monocot is maize, wheat, rice, barley, sorghum, or rye.

32. The plant cell of claim 29, wherein said plant is from a dicot.

33. The plant cell of claim 32, wherein said dicot is soybean, *Brassica*, sunflower, cotton, or alfalfa.

34. A plant comprising at least one plant cell of claim 29.

35. A transgenic seed produced by the plant of claim 34, wherein the seed comprises said expression cassette.

36. The plant cell of claim 29, wherein the plant cell further comprises at least one polypeptide imparting tolerance to an additional herbicide.

37. The plant cell of claim 36, wherein said at least one polypeptide imparting tolerance to an additional herbicide comprises:
    (a) a sulfonylurea-tolerant acetolactate synthase;
    (b) an imidazolinone-tolerant acetolactate synthase;
    (c) a glyphosate-tolerant 5-enolpyruvylshikimate-3-phosphate synthase;
    (d) a glyphosate-tolerant glyphosate oxido-reductase;
    (e) a glyphosate-N-acetyltransferase;
    (f) a phosphinothricin acetyl transferase;
    (g) a protoporphyrinogen oxidase;
    (h) an auxin enzyme or receptor;
    (i) a P450 polypeptide; or,
    (j) an acetyl coenzyme A carboxylase (ACCase).

38. The plant cell of claim 36, wherein said at least one polypeptide imparting tolerance to an additional herbicide comprises a high resistance allele of acetolactate synthase, a glyphosate-N-acetyltransferase polypeptide, or both.

\* \* \* \* \*

SEQUENCE LISTING

```
<160> NUMBER OF SEQ ID NOS: 60

<210> SEQ ID NO 1
<211> LENGTH: 53
<212> TYPE: PRT
<213> ORGANISM: Artificial Sequence
<220> FEATURE:
<223> OTHER INFORMATION: consensus sequence for monocot HPPD CTP
<220> FEATURE:
<221> NAME/KEY: VARIANT
<222> LOCATION: 6
<223> OTHER INFORMATION: The amino acid at position 6 can also be A.
<220> FEATURE:
<221> NAME/KEY: VARIANT
<222> LOCATION: 7
<223> OTHER INFORMATION: The amino acid at position 7 can also be A or
      P.
<220> FEATURE:
<221> NAME/KEY: VARIANT
<222> LOCATION: 8
<223> OTHER INFORMATION: The amino acid at position 8 can also be A or
      P.
<220> FEATURE:
<221> NAME/KEY: VARIANT
<222> LOCATION: 9
<223> OTHER INFORMATION: The amino acid at position 9 can also be T.
<220> FEATURE:
<221> NAME/KEY: VARIANT
<222> LOCATION: 10
<223> OTHER INFORMATION: The amino acid at position 10 can also be T or
      A.
<220> FEATURE:
<221> NAME/KEY: VARIANT
<222> LOCATION: (11)...(11)
<223> OTHER INFORMATION: The amino acid at position 11 can also be A or
      T.
<220> FEATURE:
<221> NAME/KEY: VARIANT
<222> LOCATION: (12)...(12)
```

```
<223> OTHER INFORMATION: The amino acid at position 12 can also be A or
      the amino acid is absent.
<220> FEATURE:
<221> NAME/KEY: VARIANT
<222> LOCATION: (13)...(13)
<223> OTHER INFORMATION: The amino acid at position 13 can be absent.
<220> FEATURE:
<221> NAME/KEY: VARIANT
<222> LOCATION: (14)...(14)
<223> OTHER INFORMATION: The amino acid at position 14 can also be V or
      the amino acid is absent.
<220> FEATURE:
<221> NAME/KEY: VARIANT
<222> LOCATION: (15)...(15)
<223> OTHER INFORMATION: The amino acid at position 15 can also be S or
      V.
<220> FEATURE:
<221> NAME/KEY: VARIANT
<222> LOCATION: (18)...(18)
<223> OTHER INFORMATION: The amino acid at position 18 can also be S.
<220> FEATURE:
<221> NAME/KEY: VARIANT
<222> LOCATION: (19)...(19)
<223> OTHER INFORMATION: The amino acid at position 19 can also be S or
      V.
<220> FEATURE:
<221> NAME/KEY: VARIANT
<222> LOCATION: (20)...(20)
<223> OTHER INFORMATION: The amino acid at position 20 can also be A.
<220> FEATURE:
<221> NAME/KEY: VARIANT
<222> LOCATION: (21)...(21)
<223> OTHER INFORMATION: The amino acid at position 21 can also be G or
      the amino acid can be absent.
<220> FEATURE:
<221> NAME/KEY: VARIANT
<222> LOCATION: (23)...(23)
<223> OTHER INFORMATION: The amino acid at position 6 can also be  N or
      Q.
<220> FEATURE:
<221> NAME/KEY: VARIANT
<222> LOCATION: (25)...(25)
<223> OTHER INFORMATION: The amino acid at position 25 can also be G or
      R.
<220> FEATURE:
<221> NAME/KEY: VARIANT
<222> LOCATION: (26)...(26)
<223> OTHER INFORMATION: The amino acid at position 26 can also be P or
      R.

<400> SEQUENCE: 1

Met Pro Pro Thr Pro Thr Thr Thr Ala Gly Gly Gly Ala Gly Ala Ala
 1               5                  10                  15

Ala Ala Ala Thr Pro Glu His Ala Ala Phe Arg Leu Val Gly His Arg
                20                  25                  30

Arg Phe Val Arg Phe Asn Pro Arg Ser Asp Arg Phe His Thr Leu Ala
            35                  40                  45

Phe His His Val Glu
        50

<210> SEQ ID NO 2
<211> LENGTH: 53
<212> TYPE: PRT
<213> ORGANISM: Artificial Sequence
<220> FEATURE:
<223> OTHER INFORMATION: consensus sequence for monocot HPPD CTP

<400> SEQUENCE: 2

Met Pro Pro Thr Pro Thr Thr Ala Ala Ala Thr Gly Ala Gly Ala Ala
 1               5                  10                  15

Ala Ala Val Thr Pro Glu His Ala Ala Phe Arg Leu Val Gly His Arg
                20                  25                  30
```

Arg Phe Val Arg Phe Asn Pro Arg Ser Asp Arg Phe His Thr Leu Ala
            35                  40                  45

Phe His His Val Glu
        50

<210> SEQ ID NO 3
<211> LENGTH: 53
<212> TYPE: PRT
<213> ORGANISM: Zea mays

<400> SEQUENCE: 3

Met Pro Pro Thr Pro Thr Ala Ala Ala Gly Ala Ala Val Ala Ala
  1               5                  10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe His Thr Leu Ala Phe
            35                  40                  45

His His Val Glu Leu
        50

<210> SEQ ID NO 4
<211> LENGTH: 99
<212> TYPE: PRT
<213> ORGANISM: sorghum bicolor

<400> SEQUENCE: 4

Met Pro Pro Thr Pro Thr Thr Ala Ala Ala Thr Gly Ala Ala Val Ala
  1               5                  10                  15

Ala Ala Ser Ala Glu Gln Ala Ala Phe Arg Leu Val Gly His Arg Asn
            20                  25                  30

Phe Val Arg Val Asn Pro Arg Ser Asp Arg Phe His Thr Leu Ala Phe
            35                  40                  45

His His Val Glu Leu Trp Cys Ala Asp Ala Ala Ser Ala Ala Gly Arg
        50                  55                  60

Phe Ser Phe Gly Leu Gly Ala Pro Leu Ala Ala Arg Ser Asp Leu Ser
65                  70                  75                  80

Thr Gly Asn Thr Ala His Ala Ser Leu Leu Leu Arg Ser Gly Ala Leu
                85                  90                  95

Ala Phe Leu

<210> SEQ ID NO 5
<211> LENGTH: 53
<212> TYPE: PRT
<213> ORGANISM: Oryza sativa

<400> SEQUENCE: 5

Met Pro Pro Thr Pro Thr Pro Thr Ala Thr Thr Gly Ala Val Ser Ala
  1               5                  10                  15

Ala Ala Ala Ala Gly Glu Asn Ala Gly Phe Arg Leu Val Gly His Arg
            20                  25                  30

Arg Phe Val Arg Ala Asn Pro Arg Ser Asp Arg Phe Gln Ala Leu Ala
            35                  40                  45

Phe His His Val Glu
        50

<210> SEQ ID NO 6
<211> LENGTH: 48
<212> TYPE: PRT

-continued

<213> ORGANISM: Triticum aestivum

<400> SEQUENCE: 6

Met Pro Pro Thr Pro Thr Thr Pro Ala Ala Thr Gly Ala Gly Ala Ala
1               5                   10                  15

Ala Ala Val Thr Pro Glu His Ala Arg Pro Arg Arg Met Val Arg Phe
            20                  25                  30

Asn Pro Arg Ser Asp Arg Phe His Thr Leu Ser Phe His His Val Glu
        35                  40                  45

<210> SEQ ID NO 7
<211> LENGTH: 46
<212> TYPE: PRT
<213> ORGANISM: Hordeum vulgare

<400> SEQUENCE: 7

Met Pro Pro Thr Pro Thr Thr Pro Ala Ala Thr Gly Ala Ala Ala Ala
1               5                   10                  15

Val Thr Pro Glu His Ala Arg Pro His Arg Met Val Arg Phe Asn Pro
            20                  25                  30

Arg Ser Asp Arg Phe His Thr Leu Ser Phe His His Val Glu
        35                  40                  45

<210> SEQ ID NO 8
<211> LENGTH: 47
<212> TYPE: PRT
<213> ORGANISM: Avena Sativa

<400> SEQUENCE: 8

Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
            20                  25                  30

Pro Arg Ser Asp Arg Phe Pro Val Leu Ser Phe His His Val Glu
        35                  40                  45

<210> SEQ ID NO 9
<211> LENGTH: 444
<212> TYPE: PRT
<213> ORGANISM: Zea mays

<400> SEQUENCE: 9

Met Gly Pro Thr Pro Thr Ala Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe His Thr Leu Ala Phe
        35                  40                  45

His His Val Glu Leu Trp Cys Ala Asp Ala Ala Ser Ala Ala Gly Arg
    50                  55                  60

Phe Ser Phe Gly Leu Gly Ala Pro Leu Ala Ala Arg Ser Asp Leu Ser
65              70                  75                  80

Thr Gly Asn Ser Ala His Ala Ser Leu Leu Leu Arg Ser Gly Ser Leu
            85                  90                  95

Ser Phe Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
        115                 120                 125

Asp His Gly Leu Ala Val Arg Ala Val Ala Leu Arg Val Ala Asp Ala
130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
                180                 185                 190

Gly Glu Pro Phe Leu Pro Gly Glu Gly Val Ala Ser Pro Gly Ala
            195                 200                 205

Ala Asp Tyr Gly Leu Ser Arg Phe Asp His Ile Val Gly Asn Val Pro
210                 215                 220

Glu Leu Ala Pro Ala Ala Ala Tyr Phe Ala Gly Phe Thr Gly Phe His
225                 230                 235                 240

Glu Phe Ala Glu Phe Thr Thr Glu Asp Val Gly Thr Ala Glu Ser Gly
                245                 250                 255

Leu Asn Ser Met Val Leu Ala Asn Asn Ser Glu Asn Val Leu Leu Pro
            260                 265                 270

Leu Asn Glu Pro Val His Gly Thr Lys Arg Arg Ser Gln Ile Gln Thr
            275                 280                 285

Phe Leu Asp His His Gly Gly Pro Gly Val Gln His Met Ala Leu Ala
290                 295                 300

Ser Asp Asp Val Leu Arg Thr Leu Arg Glu Met Gln Ala Arg Ser Ala
305                 310                 315                 320

Met Gly Gly Phe Glu Phe Met Ala Pro Pro Thr Ser Asp Tyr Tyr Asp
                325                 330                 335

Gly Val Arg Arg Arg Ala Gly Asp Val Leu Thr Glu Ala Gln Ile Lys
            340                 345                 350

Glu Cys Gln Glu Leu Gly Val Leu Val Asp Arg Asp Gln Gly Val
            355                 360                 365

Leu Leu Gln Ile Phe Thr Lys Pro Val Gly Asp Arg Pro Thr Leu Phe
370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Ser Gln Leu Phe Lys Ser Ile Glu Asp Tyr Glu Lys Ser Leu Glu Ala
            420                 425                 430

Lys Gln Ala Ala Ala Ala Ala Ala Gln Gly Ser
            435                 440

<210> SEQ ID NO 10
<211> LENGTH: 444
<212> TYPE: PRT
<213> ORGANISM: Zea mays

<400> SEQUENCE: 10

Met Pro Pro Thr Pro Thr Ala Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe His Thr Leu Ala Phe
            35                  40                  45

His His Val Glu Leu Trp Cys Ala Asp Ala Ala Ser Ala Ala Gly Arg
50                  55                  60

```
Phe Ser Phe Gly Leu Gly Ala Pro Leu Ala Ala Arg Ser Asp Leu Ser
 65                  70                  75                  80

Thr Gly Asn Ser Ala His Ala Ser Leu Leu Leu Arg Ser Gly Ser Leu
             85                  90                  95

Ser Phe Leu Phe Thr Ala Pro Tyr Ala His Gly Ala Asp Ala Ala Thr
        100                 105                 110

Ala Ala Leu Pro Ser Phe Ser Ala Ala Ala Arg Arg Phe Ala Ala
        115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
                180                 185                 190

Gly Glu Pro Phe Leu Pro Gly Phe Glu Gly Val Ala Ser Pro Gly Ala
            195                 200                 205

Ala Asp Tyr Gly Leu Ser Arg Phe Asp His Ile Val Gly Asn Val Pro
    210                 215                 220

Glu Leu Ala Pro Ala Ala Ala Tyr Phe Ala Gly Phe Thr Gly Phe His
225                 230                 235                 240

Glu Phe Ala Glu Phe Thr Thr Glu Asp Val Gly Thr Ala Glu Ser Gly
                245                 250                 255

Leu Asn Ser Met Val Leu Ala Asn Asn Ser Glu Asn Val Leu Leu Pro
                260                 265                 270

Leu Asn Glu Pro Val His Gly Thr Lys Arg Arg Ser Gln Ile Gln Thr
                275                 280                 285

Phe Leu Asp His His Gly Gly Pro Gly Val Gln His Met Ala Leu Ala
    290                 295                 300

Ser Asp Asp Val Leu Arg Thr Leu Arg Glu Met Gln Ala Arg Ser Ala
305                 310                 315                 320

Met Gly Gly Phe Glu Phe Met Ala Pro Pro Thr Ser Asp Tyr Tyr Asp
                325                 330                 335

Gly Val Arg Arg Arg Ala Gly Asp Val Leu Thr Glu Ala Gln Ile Lys
            340                 345                 350

Glu Cys Gln Glu Leu Gly Val Leu Val Asp Arg Asp Gln Gly Val
    355                 360                 365

Leu Leu Gln Ile Phe Thr Lys Pro Val Gly Asp Arg Pro Thr Leu Phe
    370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Ser Gln Leu Phe Lys Ser Ile Glu Asp Tyr Glu Lys Ser Leu Glu Ala
            420                 425                 430

Lys Gln Ala Ala Ala Ala Ala Gln Gly Ser
            435                 440

<210> SEQ ID NO 11
<211> LENGTH: 434
<212> TYPE: PRT
<213> ORGANISM: Hordeum vulgare
```

<400> SEQUENCE: 11

```
Met Pro Pro Thr Pro Thr Thr Pro Ala Ala Thr Gly Ala Ala Ala Ala
1               5                   10                  15

Val Thr Pro Glu His Ala Arg Pro His Arg Met Val Arg Phe Asn Pro
            20                  25                  30

Arg Ser Asp Arg Phe His Thr Leu Ser Phe His His Val Glu Phe Trp
        35                  40                  45

Cys Ala Asp Ala Ala Ser Ala Ala Gly Arg Phe Ala Phe Ala Leu Gly
    50                  55                  60

Ala Pro Leu Ala Ala Arg Ser Asp Leu Ser Thr Gly Asn Ser Ala His
65                  70                  75                  80

Ala Ser Gln Leu Leu Arg Ser Gly Ser Leu Ala Phe Leu Phe Thr Ala
                85                  90                  95

Pro Tyr Ala Asn Gly Cys Asp Ala Thr Ala Ser Leu Pro Ser Phe
            100                 105                 110

Ser Ala Asp Ala Ala Arg Arg Phe Ser Ala Asp His Gly Ile Ala Val
        115                 120                 125

Arg Ser Val Ala Leu Arg Val Ala Asp Ala Ala Glu Ala Phe Arg Ala
130                 135                 140

Ser Arg Arg Gly Ala Arg Pro Ala Phe Ala Pro Val Asp Leu Gly
145                 150                 155                 160

Arg Gly Phe Ala Phe Ala Glu Val Glu Leu Tyr Gly Asp Val Val Leu
                165                 170                 175

Arg Phe Val Ser His Pro Asp Gly Thr Asp Val Pro Phe Leu Pro Gly
            180                 185                 190

Phe Glu Gly Val Thr Asn Pro Asp Ala Val Asp Tyr Gly Leu Thr Arg
        195                 200                 205

Phe Asp His Val Val Gly Asn Val Pro Glu Leu Ala Pro Ala Ala Ala
210                 215                 220

Tyr Ile Ala Gly Phe Thr Gly Phe His Glu Phe Ala Glu Phe Thr Ala
225                 230                 235                 240

Glu Asp Val Gly Thr Thr Glu Ser Gly Leu Asn Ser Val Val Leu Ala
                245                 250                 255

Asn Asn Ser Glu Gly Val Leu Leu Pro Leu Asn Glu Pro Val His Gly
            260                 265                 270

Thr Lys Arg Arg Ser Gln Ile Gln Thr Phe Leu Glu His His Gly Gly
        275                 280                 285

Pro Gly Val Gln His Ile Ala Val Ala Ser Ser Asp Val Leu Arg Thr
290                 295                 300

Leu Arg Lys Met Arg Ala Arg Ser Ala Met Gly Gly Phe Asp Phe Leu
305                 310                 315                 320

Pro Pro Pro Leu Pro Lys Tyr Tyr Glu Gly Val Arg Arg Leu Ala Gly
                325                 330                 335

Asp Val Leu Ser Glu Ala Gln Ile Lys Glu Cys Gln Glu Leu Gly Val
            340                 345                 350

Leu Val Asp Arg Asp Asp Gln Gly Val Leu Leu Gln Ile Phe Thr Lys
        355                 360                 365

Pro Val Gly Asp Arg Pro Thr Leu Phe Leu Glu Met Ile Gln Arg Ile
370                 375                 380

Gly Cys Met Glu Lys Asp Glu Arg Gly Glu Glu Tyr Gln Lys Gly Gly
385                 390                 395                 400

Cys Gly Gly Phe Gly Lys Gly Asn Phe Ser Glu Leu Phe Lys Ser Ile
                405                 410                 415
```

-continued

Glu Asp Tyr Glu Lys Ser Leu Glu Ala Lys Gln Ser Ala Ala Val Gln
            420                 425                 430

Gly Ser

<210> SEQ ID NO 12
<211> LENGTH: 440
<212> TYPE: PRT
<213> ORGANISM: Avena sativa

<400> SEQUENCE: 12

Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
            20                  25                  30

Pro Arg Ser Asp Arg Phe Pro Val Leu Ser Phe His His Val Glu Leu
        35                  40                  45

Trp Cys Ala Asp Ala Ala Ser Ala Ala Gly Arg Phe Ser Phe Ala Leu
    50                  55                  60

Gly Ala Pro Leu Ala Ala Arg Ser Asp Leu Ser Thr Gly Asn Ser Ala
65                  70                  75                  80

His Ala Ser Leu Leu Leu Arg Ser Gly Ala Leu Ala Phe Leu Phe Thr
                85                  90                  95

Ala Pro Tyr Ala Pro Pro Pro Gln Glu Ala Ala Thr Ala Ala Ala Thr
            100                 105                 110

Ala Ser Ile Pro Ser Phe Ser Ala Asp Ala Ala Arg Thr Phe Ala Ala
        115                 120                 125

Ala His Gly Leu Ala Val Arg Ser Val Gly Val Arg Val Ala Asp Ala
    130                 135                 140

Ala Glu Ala Phe Arg Val Ser Val Ala Gly Gly Ala Arg Pro Ala Phe
145                 150                 155                 160

Ala Pro Ala Asp Leu Gly His Gly Phe Gly Leu Ala Glu Val Glu Leu
                165                 170                 175

Tyr Gly Asp Val Val Leu Arg Phe Val Ser Tyr Pro Asp Glu Thr Asp
            180                 185                 190

Leu Pro Phe Leu Pro Gly Phe Glu Arg Val Ser Ser Pro Gly Ala Val
        195                 200                 205

Asp Tyr Gly Leu Thr Arg Phe Asp His Val Val Gly Asn Val Pro Glu
    210                 215                 220

Met Ala Pro Val Ile Asp Tyr Met Lys Gly Phe Leu Gly Phe His Glu
225                 230                 235                 240

Phe Ala Glu Phe Thr Ala Glu Asp Val Gly Thr Thr Glu Ser Gly Leu
                245                 250                 255

Asn Ser Val Val Leu Ala Asn Asn Ser Glu Ala Val Leu Leu Pro Leu
            260                 265                 270

Asn Glu Pro Val His Gly Thr Lys Arg Arg Ser Gln Ile Gln Thr Tyr
        275                 280                 285

Leu Glu Tyr His Gly Gly Pro Gly Val Gln His Ile Ala Leu Ala Ser
    290                 295                 300

Asn Asp Val Leu Arg Thr Leu Arg Glu Met Arg Ala Arg Thr Pro Met
305                 310                 315                 320

Gly Gly Phe Glu Phe Met Ala Pro Pro Gln Ala Lys Tyr Tyr Glu Gly
                325                 330                 335

Val Arg Arg Ile Ala Gly Asp Val Leu Ser Glu Glu Gln Ile Lys Glu
            340                 345                 350

```
Cys Gln Glu Leu Gly Val Leu Val Asp Arg Asp Asp Gln Gly Val Leu
            355                 360                 365

Leu Gln Ile Phe Thr Lys Pro Val Gly Asp Arg Pro Thr Phe Phe Leu
    370                 375                 380

Glu Met Ile Gln Arg Ile Gly Cys Met Glu Lys Asp Glu Val Gly Gln
385                 390                 395                 400

Glu Tyr Gln Lys Gly Gly Cys Gly Gly Phe Gly Lys Gly Asn Phe Ser
                405                 410                 415

Glu Leu Phe Lys Ser Ile Glu Asp Tyr Glu Lys Ser Leu Glu Val Lys
            420                 425                 430

Gln Ser Val Val Ala Gln Lys Ser
        435                 440

<210> SEQ ID NO 13
<211> LENGTH: 446
<212> TYPE: PRT
<213> ORGANISM: Oryza sativa

<400> SEQUENCE: 13

Met Pro Pro Thr Pro Thr Pro Thr Ala Thr Thr Gly Ala Val Ser Ala
1               5                   10                  15

Ala Ala Ala Gly Glu Asn Ala Gly Phe Arg Leu Val Gly His Arg
            20                  25                  30

Arg Phe Val Arg Ala Asn Pro Arg Ser Asp Arg Phe Gln Ala Leu Ala
            35                  40                  45

Phe His His Val Glu Leu Trp Cys Ala Asp Ala Ala Ser Ala Ala Gly
    50                  55                  60

Arg Phe Ala Phe Ala Leu Gly Ala Pro Leu Ala Ala Arg Ser Asp Leu
65                  70                  75                  80

Ser Thr Gly Asn Ser Ala His Ala Ser Leu Leu Arg Ser Ala Ser
                85                  90                  95

Val Ala Phe Leu Phe Thr Ala Pro Tyr Gly Gly Asp His Gly Val Gly
            100                 105                 110

Ala Asp Ala Ala Thr Thr Ala Ser Ile Pro Ser Phe Ser Pro Gly Ala
            115                 120                 125

Ala Arg Arg Phe Ala Ala Asp His Gly Leu Ala Val His Ala Val Ala
        130                 135                 140

Leu Arg Val Ala Asp Ala Ala Asp Ala Phe Arg Ala Ser Val Ala Ala
145                 150                 155                 160

Gly Ala Arg Pro Ala Phe Gln Pro Ala Asp Leu Gly Gly Gly Phe Gly
                165                 170                 175

Leu Ala Glu Val Glu Leu Tyr Gly Asp Val Val Leu Arg Phe Val Ser
            180                 185                 190

His Pro Asp Gly Ala Asp Ala Pro Phe Leu Pro Gly Phe Glu Gly Val
        195                 200                 205

Ser Asn Pro Gly Ala Val Asp Tyr Gly Leu Arg Arg Phe Asp His Val
    210                 215                 220

Val Gly Asn Val Pro Glu Leu Ala Pro Val Ala Ala Tyr Ile Ser Gly
225                 230                 235                 240

Phe Thr Gly Phe His Glu Phe Ala Glu Phe Thr Ala Glu Asp Val Gly
                245                 250                 255

Thr Ala Glu Ser Gly Leu Asn Ser Val Val Leu Ala Asn Asn Ala Glu
            260                 265                 270

Thr Val Leu Leu Pro Leu Asn Glu Pro Val His Gly Thr Lys Arg Arg
```

```
                275                 280                 285
Ser Gln Ile Gln Thr Tyr Leu Asp His His Gly Gly Pro Gly Val Gln
290                 295                 300

His Ile Ala Leu Ala Ser Asp Asp Val Leu Gly Thr Leu Arg Glu Met
305                 310                 315                 320

Arg Ala Arg Ser Ala Met Gly Gly Phe Glu Phe Leu Ala Pro Pro Pro
                325                 330                 335

Pro Asn Tyr Tyr Asp Gly Val Arg Arg Arg Ala Gly Asp Val Leu Ser
                340                 345                 350

Glu Glu Gln Ile Asn Glu Cys Gln Glu Leu Gly Val Leu Val Asp Arg
                355                 360                 365

Asp Asp Gln Gly Val Leu Leu Gln Ile Phe Thr Lys Pro Val Gly Asp
                370                 375                 380

Arg Pro Thr Phe Phe Leu Glu Met Ile Gln Arg Ile Gly Cys Met Glu
385                 390                 395                 400

Lys Asp Glu Ser Gly Gln Glu Tyr Gln Lys Gly Gly Cys Gly Gly Phe
                405                 410                 415

Gly Lys Gly Asn Phe Ser Glu Leu Phe Lys Ser Ile Glu Glu Tyr Glu
                420                 425                 430

Lys Ser Leu Glu Ala Lys Gln Ala Pro Thr Val Gln Gly Ser
                435                 440                 445

<210> SEQ ID NO 14
<211> LENGTH: 436
<212> TYPE: PRT
<213> ORGANISM: Triticum aestivum

<400> SEQUENCE: 14

Met Pro Pro Thr Pro Thr Thr Pro Ala Ala Thr Gly Ala Gly Ala Ala
1               5                   10                  15

Ala Ala Val Thr Pro Glu His Ala Arg Pro Arg Met Val Arg Phe
                20                  25                  30

Asn Pro Arg Ser Asp Arg Phe His Thr Leu Ser Phe His His Val Glu
                35                  40                  45

Phe Trp Cys Ala Asp Ala Ala Ser Ala Ala Gly Arg Phe Ala Phe Ala
                50                  55                  60

Leu Gly Ala Pro Leu Ala Ala Arg Ser Asp Leu Ser Thr Gly Asn Ser
65                  70                  75                  80

Val His Ala Ser Gln Leu Leu Arg Ser Gly Asn Leu Ala Phe Leu Phe
                85                  90                  95

Thr Ala Pro Tyr Ala Asn Gly Cys Asp Ala Ala Thr Ala Ser Leu Pro
                100                 105                 110

Ser Phe Ser Ala Asp Ala Arg Arg Phe Ser Ala Asp His Gly Leu
                115                 120                 125

Ala Val Arg Ser Ile Ala Leu Arg Val Ala Asp Ala Ala Glu Ala Phe
                130                 135                 140

Arg Ala Ser Val Asp Gly Ala Arg Pro Ala Phe Ser Pro Val Asp
145                 150                 155                 160

Leu Gly Arg Gly Phe Gly Phe Ala Glu Val Glu Leu Tyr Gly Asp Val
                165                 170                 175

Val Leu Arg Phe Val Ser His Pro Asp Asp Thr Asp Val Pro Phe Leu
                180                 185                 190

Pro Gly Phe Glu Gly Val Ser Asn Pro Asp Ala Val Asp Tyr Gly Leu
                195                 200                 205
```

```
Thr Arg Phe Asp His Val Val Gly Asn Val Pro Glu Leu Ala Pro Ala
    210                 215                 220

Ala Ala Tyr Val Ala Gly Phe Ala Gly Phe His Glu Phe Ala Glu Phe
225                 230                 235                 240

Thr Thr Glu Asp Val Gly Thr Ala Glu Ser Gly Leu Asn Ser Met Val
                245                 250                 255

Leu Ala Asn Asn Ser Glu Gly Val Leu Leu Pro Leu Asn Glu Pro Val
                260                 265                 270

His Gly Thr Lys Arg Arg Ser Gln Ile Gln Thr Phe Leu Glu His His
            275                 280                 285

Gly Gly Ser Gly Val Gln His Ile Ala Val Ala Ser Ser Asp Val Leu
290                 295                 300

Arg Thr Leu Arg Glu Met Arg Ala Arg Ser Ala Met Gly Gly Phe Asp
305                 310                 315                 320

Phe Leu Pro Pro Arg Cys Arg Lys Tyr Tyr Glu Gly Val Arg Arg Ile
                    325                 330                 335

Ala Gly Asp Val Leu Ser Glu Ala Gln Ile Lys Glu Cys Gln Glu Leu
                340                 345                 350

Gly Val Leu Val Asp Arg Asp Asp Gln Gly Val Leu Leu Gln Ile Phe
            355                 360                 365

Thr Lys Pro Val Gly Asp Arg Pro Thr Leu Phe Leu Glu Met Ile Gln
    370                 375                 380

Arg Ile Gly Cys Met Glu Lys Asp Glu Arg Gly Glu Tyr Gln Lys
385                 390                 395                 400

Gly Gly Cys Gly Gly Phe Gly Lys Gly Asn Phe Ser Glu Leu Phe Lys
                    405                 410                 415

Ser Ile Glu Asp Tyr Glu Lys Ser Leu Glu Ala Lys Gln Ser Ala Ala
                420                 425                 430

Val Gln Gly Ser
            435

<210> SEQ ID NO 15
<211> LENGTH: 316
<212> TYPE: PRT
<213> ORGANISM: Daucus carota

<400> SEQUENCE: 15

Met Gly Lys Lys Gln Ser Glu Ala Glu Ile Leu Ser Ser Asn Ser Ser
1               5                   10                  15

Asn Thr Ser Pro Ala Thr Phe Lys Leu Val Gly Phe Asn Asn Phe Val
                20                  25                  30

Arg Ala Asn Pro Lys Ser Asp His Phe Ala Val Lys Arg Phe His His
            35                  40                  45

Ile Glu Phe Trp Cys Gly Asp Ala Thr Asn Thr Ser Arg Arg Phe Ser
    50                  55                  60

Trp Gly Leu Gly Met Pro Leu Val Ala Lys Ser Asp Leu Ser Thr Gly
65                  70                  75                  80

Asn Ser Val His Ala Ser Tyr Leu Val Arg Ser Ala Asn Leu Ser Phe
                85                  90                  95

Val Phe Thr Ala Pro Tyr Ser Pro Ser Thr Thr Thr Ser Ser Gly Ser
                100                 105                 110

Ala Ala Ile Pro Ser Phe Ser Ala Ser Gly Phe His Ser Phe Ala Ala
            115                 120                 125

Lys His Gly Leu Ala Val Arg Ala Ile Ala Leu Glu Val Ala Asp Val
        130                 135                 140
```

Ala Ala Ala Phe Glu Ala Ser Val Ala Arg Gly Ala Arg Pro Ala Ser
145                 150                 155                 160

Ala Pro Val Glu Leu Asp Asp Gln Ala Trp Leu Ala Glu Val Glu Leu
                165                 170                 175

Tyr Gly Asp Val Val Leu Arg Phe Val Ser Phe Gly Arg Glu Glu Gly
            180                 185                 190

Leu Phe Leu Pro Gly Phe Glu Ala Val Glu Gly Thr Ala Ser Phe Pro
        195                 200                 205

Asp Leu Asp Tyr Gly Ile Arg Arg Leu Asp His Ala Val Gly Asn Val
    210                 215                 220

Thr Glu Leu Gly Pro Val Val Glu Tyr Ile Lys Gly Phe Thr Gly Phe
225                 230                 235                 240

His Glu Phe Ala Glu Phe Thr Ala Glu Asp Val Gly Thr Leu Glu Ser
                245                 250                 255

Gly Leu Asn Ser Val Val Leu Ala Asn Asn Glu Glu Met Val Leu Leu
            260                 265                 270

Pro Leu Asn Glu Pro Val Tyr Gly Thr Lys Arg Lys Ser Gln Ile Gln
        275                 280                 285

Thr Tyr Leu Glu His Asn Glu Gly Ala Gly Val Gln His Leu Ala Leu
    290                 295                 300

Val Ser Glu Asp Ile Phe Arg Thr Leu Arg Glu Met
305                 310                 315

<210> SEQ ID NO 16
<211> LENGTH: 436
<212> TYPE: PRT
<213> ORGANISM: Solenosteman sautellarioides

<400> SEQUENCE: 16

Met Gly Gln Glu Ser Thr Ala Ala Ala Val Val Pro Ala Glu Phe
1               5                   10                  15

Lys Leu Val Gly His Lys Asn Phe Val Arg Ser Asn Pro Met Ser Asp
            20                  25                  30

His Phe Pro Val His Arg Phe His His Val Glu Phe Trp Cys Gly Asp
        35                  40                  45

Ala Thr Asn Thr Ser Arg Arg Phe Ser Trp Gly Leu Gly Met Pro Leu
    50                  55                  60

Val Ala Lys Ser Asp Leu Ser Thr Gly Asn Ser Ala His Ala Ser Tyr
65                  70                  75                  80

Leu Leu Arg Ser Gly Glu Leu Ser Phe Val Phe Thr Ala Pro Tyr Ser
                85                  90                  95

Pro Ser Leu Ala Glu Pro Ser Ser Ala Ser Ile Pro Thr Phe Ser Phe
            100                 105                 110

Ser Asp His Arg Ala Phe Thr Ser Ser His Gly Leu Ala Val Arg Ala
        115                 120                 125

Val Ala Ile Gln Val Asp Ser Ala Ser Ser Ala Tyr Ser Ala Ala Val
    130                 135                 140

Ser Arg Gly Ala Lys Pro Val Ser Pro Val Val Leu Ala Asp Cys
145                 150                 155                 160

Glu Thr Ala Ile Ala Glu Val His Leu Tyr Gly Asp Thr Val Leu Arg
                165                 170                 175

Phe Val Ser Cys Gly Ser Gly Ala Asp Gly Trp Phe Leu Pro Gly Phe
            180                 185                 190

Glu Val Val Gly Asp Gly Val Ser Cys Gln Glu Leu Asp Tyr Gly Ile

```
                195                 200                 205
Arg Arg Leu Asp His Ala Val Gly Asn Val Pro Lys Leu Glu Pro Val
210                 215                 220

Val Asp Tyr Leu Lys Lys Phe Thr Gly Phe His Glu Phe Ala Glu Phe
225                 230                 235                 240

Thr Ala Glu Asp Val Gly Thr Ala Glu Ser Gly Leu Asn Ser Val Val
                245                 250                 255

Leu Ala Asn Asn Asn Glu Asn Val Leu Phe Pro Leu Asn Glu Pro Val
            260                 265                 270

Tyr Gly Thr Lys Arg Lys Ser Gln Ile Gln Thr Tyr Leu Asp His Asn
        275                 280                 285

Glu Gly Ala Gly Val Gln His Leu Ala Leu Ile Thr Glu Asp Ile Phe
    290                 295                 300

Arg Thr Leu Arg Glu Met Arg Lys Arg Ser Val Gly Gly Phe Glu
305                 310                 315                 320

Phe Met Pro Ser Pro Pro Thr Tyr Tyr Arg Asn Leu Lys Ser Arg
                325                 330                 335

Ala Gly Asp Val Leu Ser Asp Glu Gln Ile Glu Glu Cys Glu Lys Leu
            340                 345                 350

Gly Ile Leu Ile Asp Arg Asp Gln Gly Thr Leu Leu Gln Ile Phe
        355                 360                 365

Thr Lys Pro Val Gly Asp Arg Pro Thr Leu Phe Ile Glu Ile Ile Gln
    370                 375                 380

Arg Val Gly Cys Met Met Lys Asp Glu Glu Gly Lys Met Tyr Gln Lys
385                 390                 395                 400

Gly Gly Cys Gly Gly Phe Gly Lys Gly Asn Phe Ser Glu Leu Phe Lys
                405                 410                 415

Ser Ile Glu Glu Tyr Glu Lys Met Leu Glu Ser Lys Leu Val Thr Lys
            420                 425                 430

Thr Ala Met Ala
        435

<210> SEQ ID NO 17
<211> LENGTH: 142
<212> TYPE: PRT
<213> ORGANISM: Picea sitchensis

<400> SEQUENCE: 17

Met Ser Glu Val Lys Leu Tyr Gly Asp Val Val Leu Arg Phe Val Ser
1               5                   10                  15

Lys Asp Gly Phe Glu Gly Pro Phe Leu Pro Asn Tyr Glu Pro Val Gln
                20                  25                  30

Ser Ile Pro Leu Ser Tyr Gly Ile Ile Arg Val Asp His Ala Val Gly
            35                  40                  45

Asn Val Glu Lys Leu Glu Glu Ala Val Glu Tyr Val Ala Lys Phe Thr
        50                  55                  60

Gly Phe His Arg Phe Ala Glu Phe Thr Ala Glu Asp Val Gly Thr Ala
65                  70                  75                  80

Glu Ser Gly Leu Asn Ser Met Val Leu Ala Ser Asn Asn Glu Met Val
                85                  90                  95

Leu Leu Pro Met Asn Glu Pro Val Phe Gly Thr Lys Arg Lys Ser Gln
            100                 105                 110

Ile Gln Thr Tyr Leu Glu His Asn Glu Gly Pro Gly Leu Gln His Leu
        115                 120                 125
```

```
Ala Leu Ile Cys Ser Asp Ile Phe Ser Thr Leu Lys Glu Met
    130                 135                 140
```

<210> SEQ ID NO 18
<211> LENGTH: 363
<212> TYPE: PRT
<213> ORGANISM: Abutilon theophrasti

<400> SEQUENCE: 18

```
Cys Thr Asp Ala Thr Asn Ala Ala Cys Arg Phe Ser Trp Gly Leu Gly
  1               5                  10                  15

Met Gln Phe Val Ala Lys Ser Asp Leu Ser Thr Gly Asn Leu Ser His
             20                  25                  30

Ala Ser Tyr Leu Leu Arg Ser Asp His Leu Ser Leu Leu Phe Thr Ala
         35                  40                  45

Pro Tyr Ser Pro Ser Ile Ala Leu Ser Gln Asn Ile Ser Pro His Ser
     50                  55                  60

Thr Ala Ser Ile Pro Ser Phe Asp His Thr Leu Cys Arg Ser Phe Ser
 65                  70                  75                  80

Ser Ser His Gly Leu Val Val Arg Ala Ile Ala Leu Glu Val Glu Asp
                 85                  90                  95

Ser Glu Thr Ala Phe Ala Thr Ser Ile Ser Asn Gly Ala Leu Pro Ser
            100                 105                 110

Ser Pro Pro Ile Leu Leu Asp Gly Ala Thr Ile Ser Glu Val Lys Leu
        115                 120                 125

Tyr Gly Asp Val Val Leu Arg Tyr Val Ser Tyr Ser Lys Asn Thr Asn
    130                 135                 140

Pro His His Phe Leu Pro Gly Phe Glu Lys Val Glu Asp Asn Leu Ser
145                 150                 155                 160

Tyr Pro Leu Asp Tyr Gly Ile Arg Arg Leu Asp His Ala Val Cys Cys
                165                 170                 175

Val Pro Glu Leu Gly Pro Ala Ile Ser Tyr Val Lys Ser Phe Thr Gly
            180                 185                 190

Phe His Asp Leu Ala Glu Phe Thr Ala Glu Asp Val Gly Thr Ser Glu
        195                 200                 205

Ser Gly Leu Asn Ser Val Ile Leu Ala Asn Asn Glu Met Val Leu
    210                 215                 220

Met Pro Ile Ala Glu Pro Val Tyr Gly Thr Lys Arg Lys Ser Gln Val
225                 230                 235                 240

Gln Thr Tyr Leu Glu His Asn Glu Gly Ala Gly Val Gln His Leu Ala
                245                 250                 255

Leu Leu Ser Glu Asp Ile Phe Arg Thr Leu Arg Glu Met Arg Lys Arg
            260                 265                 270

Ser Phe Val Gly Gly Phe Glu Phe Met Pro Ser Pro Pro Thr Tyr
        275                 280                 285

Tyr Glu Lys Leu Lys Gln Arg Val Gly Asp Ile Leu Ser Asp Glu Gln
    290                 295                 300

Ile Lys Glu Cys Glu Glu Leu Gly Ile Met Val Asp Arg Asp Gln
305                 310                 315                 320

Gly Thr Leu Leu Gln Ile Phe Thr Lys Pro Ile Gly Asp Arg Pro Thr
                325                 330                 335

Ile Leu Leu Glu Ile Ile Gln Arg Ile Gly Cys Met Val Lys Asp Glu
            340                 345                 350

Glu Gly Lys Gln Tyr Gln Lys Gly Gly Cys Gly
        355                 360
```

<210> SEQ ID NO 19
<211> LENGTH: 473
<212> TYPE: PRT
<213> ORGANISM: Arabidopsis thaliana

<400> SEQUENCE: 19

```
Met Cys Leu Ser Leu Ala Ser Thr Ala Gln Arg Asn Thr Lys Phe Arg
  1               5                  10                  15

Ser Arg Val Leu Val Leu Ala Glu Leu Val Lys Ser Met Gly His Gln
             20                  25                  30

Asn Ala Ala Val Ser Glu Asn Gln Asn His Asp Asp Gly Ala Ala Ser
         35                  40                  45

Ser Pro Gly Phe Lys Leu Val Gly Phe Ser Lys Phe Val Arg Lys Asn
     50                  55                  60

Pro Lys Ser Asp Lys Phe Lys Val Lys Arg Phe His His Ile Glu Phe
 65                  70                  75                  80

Trp Cys Gly Asp Ala Thr Asn Val Ala Arg Arg Phe Ser Trp Gly Leu
                 85                  90                  95

Gly Met Arg Phe Ser Ala Lys Ser Asp Leu Ser Thr Gly Asn Met Val
            100                 105                 110

His Ala Ser Tyr Leu Leu Thr Ser Gly Asp Leu Arg Phe Leu Phe Thr
        115                 120                 125

Ala Pro Tyr Ser Pro Ser Leu Ser Ala Gly Glu Ile Lys Pro Thr Thr
    130                 135                 140

Thr Ala Ser Ile Pro Ser Phe Asp His Gly Ser Cys Arg Ser Phe Phe
145                 150                 155                 160

Ser Ser His Gly Leu Gly Val Arg Ala Val Ala Ile Glu Val Glu Asp
                165                 170                 175

Ala Glu Ser Ala Phe Ser Ile Ser Val Ala Asn Gly Ala Ile Pro Ser
            180                 185                 190

Ser Pro Pro Ile Val Leu Asn Glu Ala Val Thr Ile Ala Glu Val Lys
        195                 200                 205

Leu Tyr Gly Asp Val Val Leu Arg Tyr Val Ser Tyr Lys Ala Glu Asp
    210                 215                 220

Thr Glu Lys Ser Glu Phe Leu Pro Gly Phe Glu Arg Val Glu Asp Ala
225                 230                 235                 240

Ser Ser Phe Pro Leu Asp Tyr Gly Ile Arg Arg Leu Asp His Ala Val
                245                 250                 255

Gly Asn Val Pro Glu Leu Gly Pro Ala Leu Thr Tyr Val Ala Gly Phe
            260                 265                 270

Thr Gly Phe His Gln Phe Ala Glu Phe Thr Ala Asn Asp Val Gly Thr
        275                 280                 285

Ala Glu Ser Gly Leu Asn Ser Ala Val Leu Ala Ser Asn Asp Glu Met
    290                 295                 300

Val Leu Leu Pro Ile Asn Glu Pro Val His Gly Thr Lys Arg Lys Ser
305                 310                 315                 320

Gln Ile Gln Thr Tyr Leu Glu His Asn Glu Gly Ala Gly Leu Gln His
                325                 330                 335

Leu Ala Leu Met Ser Glu Asp Ile Phe Arg Thr Leu Arg Glu Met Arg
            340                 345                 350

Lys Arg Ser Ser Ile Gly Gly Phe Asp Phe Met Pro Ser Pro Pro Pro
        355                 360                 365

Thr Tyr Tyr Gln Asn Leu Lys Lys Arg Val Gly Asp Val Leu Ser Asp
```

```
                    370                 375                 380
Asp Gln Ile Lys Glu Cys Glu Leu Gly Ile Leu Val Asp Arg Asp
385                 390                 395                 400

Asp Gln Gly Thr Leu Leu Gln Ile Phe Thr Lys Pro Leu Gly Asp Arg
                405                 410                 415

Pro Thr Ile Phe Ile Glu Ile Ile Gln Arg Val Gly Cys Met Met Lys
                420                 425                 430

Asp Glu Glu Gly Lys Ala Tyr Gln Ser Gly Gly Cys Gly Gly Phe Gly
                435                 440                 445

Lys Gly Asn Phe Ser Glu Leu Phe Lys Ser Ile Glu Glu Tyr Glu Lys
                450                 455                 460

Thr Leu Glu Ala Lys Gln Leu Val Gly
465                 470

<210> SEQ ID NO 20
<211> LENGTH: 443
<212> TYPE: PRT
<213> ORGANISM: Brassica rapa

<400> SEQUENCE: 20

Met Gly His Glu Asn Ala Ala Val Ser Glu Asn Gln His His Asp Asp
 1               5                  10                  15

Ala Ala Thr Thr Ser Ala Ser Pro Gly Phe Lys Leu Val Gly Phe Ser
                20                  25                  30

Lys Phe Val Arg Lys Asn Pro Lys Ser Asp Lys Phe Lys Val Lys Arg
                35                  40                  45

Phe His His Ile Glu Phe Trp Cys Gly Asp Ala Thr Asn Val Ala Arg
                50                  55                  60

Arg Phe Ser Trp Gly Leu Gly Met Arg Phe Ser Ala Lys Ser Asp Leu
65                  70                  75                  80

Ser Thr Gly Asn Met Val His Ala Ser Tyr Leu Leu Thr Ser Gly Asp
                    85                  90                  95

Leu Arg Phe Leu Phe Thr Ala Pro Tyr Ser Pro Ser Leu Ser Ala Gly
                100                 105                 110

Glu Asn Pro Pro Thr Thr Thr Ala Ser Ile Pro Ser Phe Asp His Val
                115                 120                 125

Thr Tyr Arg Ser Phe Phe Ser Ser His Gly Leu Gly Val Arg Ala Val
                130                 135                 140

Ala Val Glu Val Glu Asp Ala Glu Ala Ala Phe Ser Ile Ser Val Ser
145                 150                 155                 160

Asn Gly Ala Val Pro Ser Ser Pro Ile Val Leu Asn Asp Ala Val
                165                 170                 175

Thr Ile Ala Glu Val Lys Leu Tyr Gly Asp Val Leu Arg Tyr Val
                180                 185                 190

Ser Tyr Lys Val Ala Thr Val Phe Leu Pro Arg Phe Glu Thr Val Asp
                195                 200                 205

Asp Thr Ser Ser Phe Pro Leu Asp Tyr Gly Ile Arg Arg Leu Asp His
                210                 215                 220

Ala Val Gly Asn Val Pro Glu Leu Gly Pro Ala Leu Thr Tyr Leu Ser
225                 230                 235                 240

Arg Leu Thr Gly Phe His Gln Phe Ala Glu Phe Thr Ala Asp Asp Val
                245                 250                 255

Gly Thr Ala Glu Ser Gly Leu Asn Ser Ala Val Leu Ala Asn Asn Asp
                260                 265                 270
```

```
Glu Thr Val Leu Leu Pro Val Asn Glu Pro Val His Gly Thr Lys Arg
            275                 280                 285

Lys Ser Gln Ile Gln Thr Tyr Leu Glu His Asn Glu Gly Ala Gly Val
        290                 295                 300

Gln His Leu Ala Leu Met Ser Glu Asp Ile Phe Arg Thr Leu Arg Glu
305                 310                 315                 320

Met Arg Lys Arg Ser Gly Val Gly Gly Phe Asp Phe Met Pro Ser Pro
                325                 330                 335

Pro Pro Thr Tyr Tyr Lys Asn Leu Lys Asn Arg Val Gly Asp Val Leu
            340                 345                 350

Ser Glu Glu Gln Ile Glu Glu Cys Glu Glu Leu Gly Ile Leu Val Asp
        355                 360                 365

Arg Asp Asp Gln Gly Thr Leu Leu Gln Ile Phe Thr Lys Pro Leu Gly
    370                 375                 380

Asp Arg Pro Thr Ile Phe Ile Glu Ile Ile Gln Arg Ile Gly Cys Met
385                 390                 395                 400

Lys Lys Asp Glu Glu Gly Arg Val Tyr Gln Ser Gly Gly Cys Gly Gly
                405                 410                 415

Phe Gly Lys Gly Asn Phe Ser Glu Leu Phe Lys Ser Ile Glu Glu Tyr
            420                 425                 430

Glu Lys Thr Leu Glu Ala Lys Gln Leu Val Gly
        435                 440

<210> SEQ ID NO 21
<211> LENGTH: 430
<212> TYPE: PRT
<213> ORGANISM: Coptis japonica

<400> SEQUENCE: 21

Met Val Pro Ser Thr Ala Ser Asn Leu Lys Leu Val Gly His Thr Asn
1               5                   10                  15

Phe Val His Asn Asn Pro Lys Ser Asp Lys Phe His Val Lys Lys Phe
                20                  25                  30

His His Ile Glu Phe Trp Ser Thr Asp Ala Thr Asn Thr Ala Arg Arg
            35                  40                  45

Phe Ser Trp Gly Leu Gly Met Pro Met Val Ala Lys Ser Asp Leu Ser
    50                  55                  60

Thr Gly Asn Met Val His Ala Ser Tyr Leu Leu Arg Ser Gly Glu Leu
65                  70                  75                  80

Asn Phe Leu Phe Thr Ala Pro Tyr Ser Pro Ser Ile Ala Gly Asn Thr
                85                  90                  95

Leu Thr His Thr Ala Ser Ile Pro Thr Tyr Ser His Asn Leu Ala Arg
            100                 105                 110

Leu Phe Ala Ser Thr His Gly Leu Ala Val Arg Ala Ile Ala Ile Glu
    115                 120                 125

Val Gln Asp Ala Glu Leu Ala Tyr Asn Ile Ser Val Ala Asn Gly Ala
130                 135                 140

Lys Pro Ser Ser Ser Pro Ile Lys Leu Asp Glu Gly Val Val Leu Ser
145                 150                 155                 160

Glu Ile Gln Leu Tyr Gly Asp Val Val Leu Arg Tyr Leu Ser Phe Lys
                165                 170                 175

Asn Thr Asn Gln Ser Cys Pro Phe Leu Pro Gly Phe Glu Glu Val Gly
            180                 185                 190

Glu Val Ser Ser Ser Arg Gly Leu Asp Phe Gly Ile Arg Arg Leu Asp
    195                 200                 205
```

His Ala Val Gly Asn Val Pro Asn Leu Ala Glu Ala Ile Gly Tyr Leu
    210                 215                 220

Lys Glu Phe Thr Gly Phe His Glu Phe Ala Glu Phe Thr Ala Glu Asp
225                 230                 235                 240

Val Gly Thr Thr Glu Ser Gly Leu Asn Ser Ile Val Leu Ala Ser Asn
                    245                 250                 255

Asp Glu Met Val Leu Leu Pro Met Asn Glu Pro Val Tyr Gly Thr Lys
                260                 265                 270

Arg Lys Ser Gln Ile Gln Thr Tyr Leu Glu His Asn Glu Gly Ala Gly
            275                 280                 285

Val Gln His Leu Ala Leu Val Ser Glu Asp Ile Phe Thr Thr Leu Arg
        290                 295                 300

Glu Met Arg Arg Arg Ser Gly Val Gly Gly Phe Glu Phe Met Pro Ser
305                 310                 315                 320

Pro Pro Pro Thr Tyr Tyr Lys Asn Leu Lys Asn Arg Ala Gly Asp Val
                    325                 330                 335

Leu Ser Asp Glu Gln Ile Lys Glu Cys Glu Glu Leu Gly Ile Leu Val
                340                 345                 350

Asp Arg Asp Ala Gln Gly Thr Leu Leu Gln Ile Phe Thr Lys Pro Val
            355                 360                 365

Gly Asp Arg Pro Thr Ile Phe Val Glu Ile Ile Gln Arg Leu Gly Cys
        370                 375                 380

Met Leu Lys Asp Glu Glu Gly Lys Thr Tyr Gln Lys Ala Gly Cys Gly
385                 390                 395                 400

Gly Phe Gly Lys Gly Asn Phe Ser Glu Leu Phe Lys Ser Ile Glu Glu
                    405                 410                 415

Tyr Glu Lys Thr Leu Glu Ala Lys Ala Asn Val Val Ala Ala
                420                 425                 430

<210> SEQ ID NO 22
<211> LENGTH: 445
<212> TYPE: PRT
<213> ORGANISM: Vitis vinifera

<400> SEQUENCE: 22

Met Gly Lys Gln Asn Thr Thr Asn Asn Pro Ala Pro Gly Phe Lys
1               5                   10                  15

Leu Val Gly Phe Ser Asn Phe Leu Arg Thr Asn Pro Met Ser Asp Arg
                    20                  25                  30

Phe Gly Val Lys Arg Phe His His Ile Glu Phe Trp Ser Thr Asp Ala
            35                  40                  45

Thr Asn Leu Ala Arg Arg Phe Ser Trp Gly Leu Gly Met Pro Ile Val
        50                  55                  60

Ala Lys Ser Asp Leu Ser Thr Gly Asn Val Ile His Ala Ser Tyr Leu
65              70                  75                  80

Thr Arg Ser Gly Asp Leu Asn Phe Leu Phe Thr Ala Pro Tyr Ser Pro
                    85                  90                  95

Ser Ile Ala Gly Asp Leu Glu Asn Ala Ala Thr Ala Ser Ile Pro
                100                 105                 110

Ser Phe Asp His Ser Ala Cys His Ala Phe Ala Ala Ser His Gly Leu
            115                 120                 125

Gly Val Arg Ala Ile Ala Ile Glu Val Asp Asp Ala Glu Gly Ala Phe
        130                 135                 140

His Thr Ser Val Ala His Gly Ala Arg Pro Met Ser Pro Pro Val Thr

```
                145                 150                 155                 160
Met Gly Gly Ser Val Val Ile Ser Glu Val His Leu Tyr Gly Asp Ala
                    165                 170                 175

Val Leu Arg Tyr Val Ser Tyr Lys Asn Pro Asn Pro Asn Ala Thr Ser
                    180                 185                 190

Asp Pro Ser Ser Trp Phe Leu Pro Gly Phe Glu Ala Val Asp Glu Gly
                    195                 200                 205

Ser Ser Phe Pro Val Asp Phe Gly Leu Arg Arg Val Asp His Thr Val
210                 215                 220

Gly Asn Val Pro Lys Leu Ala Pro Val Val Thr Tyr Leu Lys Gln Phe
225                 230                 235                 240

Thr Gly Phe His Glu Phe Ala Glu Phe Thr Ala Glu Asp Val Gly Thr
                    245                 250                 255

Ser Glu Ser Gly Leu Asn Ser Val Val Leu Ala Ser Asn Asn Glu Met
                    260                 265                 270

Val Leu Leu Pro Leu Asn Glu Pro Val Phe Gly Thr Lys Arg Lys Ser
                    275                 280                 285

Gln Ile Gln Thr Tyr Leu Glu His Asn Glu Gly Pro Gly Val Gln His
                    290                 295                 300

Leu Ala Leu Met Ser Asp Asp Ile Phe Arg Thr Leu Arg Glu Met Arg
305                 310                 315                 320

Arg Arg Ser Gly Val Gly Gly Phe Asp Phe Met Pro Ser Pro Pro Pro
                    325                 330                 335

Thr Tyr Tyr Arg Asn Val Lys Lys Arg Ala Gly Asp Val Leu Thr Asp
                    340                 345                 350

Asp Gln Ile Lys Glu Cys Glu Glu Leu Gly Ile Leu Val Asp Lys Asp
                    355                 360                 365

Asp Gln Gly Thr Leu Leu Gln Ile Phe Thr Lys Pro Leu Gly Asp Arg
                    370                 375                 380

Pro Thr Ile Phe Ile Glu Ile Ile Gln Arg Leu Gly Cys Met Val Lys
385                 390                 395                 400

Asp Asp Glu Gly Lys Val Ser Gln Lys Gly Cys Gly Gly Phe Gly
                    405                 410                 415

Lys Gly Asn Phe Ser Glu Leu Phe Lys Ser Ile Glu Glu Tyr Glu Lys
                    420                 425                 430

Thr Leu Gly Ala Lys Arg Ile Val Asp Pro Ala Pro Val
                    435                 440                 445

<210> SEQ ID NO 23
<211> LENGTH: 449
<212> TYPE: PRT
<213> ORGANISM: Glycine max

<400> SEQUENCE: 23

Met Pro Ile Pro Met Cys Asn Glu Ile Gln Ala Gln Ala Gln Ala Gln
1               5                   10                  15

Ala Gln Ala Gln Pro Gly Phe Lys Leu Val Gly Phe Lys Asn Phe Val
                    20                  25                  30

Arg Thr Asn Pro Lys Ser Asp Arg Phe Gln Val Asn Arg Phe His His
                    35                  40                  45

Ile Glu Phe Trp Cys Thr Asp Ala Thr Asn Ala Ser Arg Arg Phe Ser
                    50                  55                  60

Trp Gly Leu Gly Met Pro Ile Val Ala Lys Ser Asp Leu Ser Thr Gly
65                  70                  75                  80
```

```
Asn Gln Ile His Ala Ser Tyr Leu Leu Arg Ser Gly Asp Leu Ser Phe
                 85                  90                  95

Leu Phe Ser Ala Pro Tyr Ser Pro Ser Leu Ser Ala Gly Ser Ser Ala
            100                 105                 110

Ala Ser Ser Ala Ser Ile Pro Ser Phe Asp Ala Ala Thr Cys Leu Ala
            115                 120                 125

Phe Ala Ala Lys His Gly Phe Gly Val Arg Ala Ile Ala Leu Glu Val
            130                 135                 140

Ala Asp Ala Glu Ala Ala Phe Ser Ala Ser Val Ala Lys Gly Ala Glu
145                 150                 155                 160

Pro Ala Ser Pro Pro Val Leu Val Asp Asp Arg Thr Gly Phe Ala Glu
                165                 170                 175

Val Arg Leu Tyr Gly Asp Val Val Leu Arg Tyr Val Ser Tyr Lys Asp
                180                 185                 190

Ala Ala Pro Gln Ala Pro His Ala Asp Pro Ser Arg Trp Phe Leu Pro
                195                 200                 205

Gly Phe Glu Ala Ala Ala Ser Ser Ser Phe Pro Glu Leu Asp Tyr
            210                 215                 220

Gly Ile Arg Arg Leu Asp His Ala Val Gly Asn Val Pro Glu Leu Ala
225                 230                 235                 240

Pro Ala Val Arg Tyr Leu Lys Gly Phe Ser Gly Phe His Glu Phe Ala
                245                 250                 255

Glu Phe Thr Ala Glu Asp Val Gly Thr Ser Glu Ser Gly Leu Asn Ser
                260                 265                 270

Val Val Leu Ala Asn Asn Ser Glu Thr Val Leu Leu Pro Leu Asn Glu
                275                 280                 285

Pro Val Tyr Gly Thr Lys Arg Lys Ser Gln Ile Glu Thr Tyr Leu Glu
                290                 295                 300

His Asn Glu Gly Ala Gly Val Gln His Leu Ala Leu Val Thr His Asp
305                 310                 315                 320

Ile Phe Thr Thr Leu Arg Glu Met Arg Lys Arg Ser Phe Leu Gly Gly
                325                 330                 335

Phe Glu Phe Met Pro Ser Pro Pro Thr Tyr Tyr Ala Asn Leu His
            340                 345                 350

Asn Arg Ala Ala Asp Val Leu Thr Val Asp Gln Ile Lys Gln Cys Glu
                355                 360                 365

Glu Leu Gly Ile Leu Val Asp Arg Asp Gln Gly Thr Leu Leu Gln
            370                 375                 380

Ile Phe Thr Lys Pro Val Gly Asp Arg Pro Thr Ile Phe Ile Glu Ile
385                 390                 395                 400

Ile Gln Arg Ile Gly Cys Met Val Glu Asp Glu Glu Gly Lys Val Tyr
                405                 410                 415

Gln Lys Gly Ala Cys Gly Gly Phe Gly Lys Gly Asn Phe Ser Glu Leu
            420                 425                 430

Phe Lys Ser Ile Glu Glu Tyr Glu Lys Thr Leu Glu Ala Lys Arg Thr
            435                 440                 445

Ala
```

<210> SEQ ID NO 24
<211> LENGTH: 437
<212> TYPE: PRT
<213> ORGANISM: Medicago truncatula

<400> SEQUENCE: 24

```
Met Ala Ile Glu Thr Glu Thr Gln Thr Gln Thr Gly Phe Lys
 1               5                  10                  15

Leu Val Gly Phe Lys Asn Phe Val Arg Ala Asn Pro Lys Ser Asp Arg
            20                  25                  30

Phe Asn Val Lys Arg Phe His His Val Glu Phe Trp Cys Thr Asp Ala
            35                  40                  45

Thr Asn Thr Ala Arg Arg Phe Ser His Gly Leu Gly Met Pro Ile Val
 50                      55                  60

Ala Lys Ser Asp Leu Ser Thr Gly Asn Leu Thr His Ala Ser Tyr Leu
 65                  70                  75                  80

Leu Arg Ser Gly Asp Leu Asn Phe Leu Phe Ser Ala Ala Tyr Ser Pro
                85                  90                  95

Ser Ile Ser Leu Ser Ser Pro Ser Ser Thr Ala Ala Ile Pro Thr Phe
                100                 105                 110

Ser Ala Ser Thr Cys Phe Ser Phe Ser Ala Ser His Gly Leu Ala Val
                115                 120                 125

Arg Ala Val Ala Val Glu Val Glu Asp Ala Glu Val Ala Phe Thr Thr
            130                 135                 140

Ser Val Asn Leu Gly Ala Ile Pro Ser Ser Pro Pro Val Ile Leu Glu
145                 150                 155                 160

Asn Asn Val Lys Leu Ala Glu Val His Leu Tyr Gly Asp Val Val Leu
                165                 170                 175

Arg Tyr Val Ser Tyr Asn Asp Leu Asn Pro Asn Gln Asn Pro Asn Leu
                180                 185                 190

Phe Phe Leu Pro Gly Phe Glu Arg Val Ser Asp Glu Ser Ser Asn Ser
                195                 200                 205

Ser Leu Asp Phe Gly Ile Arg Arg Leu Asp His Ala Val Gly Asn Val
        210                 215                 220

Pro Glu Leu Ser Ser Ala Val Lys Tyr Val Lys Gln Phe Thr Gly Phe
225                 230                 235                 240

His Glu Phe Ala Glu Phe Thr Ala Glu Asp Val Gly Thr Ser Glu Ser
                245                 250                 255

Gly Leu Asn Ser Val Val Leu Ala Asn Asn Glu Glu Thr Val Leu Leu
            260                 265                 270

Pro Met Asn Glu Pro Val Tyr Gly Thr Lys Arg Lys Ser Gln Ile Glu
        275                 280                 285

Thr Tyr Leu Glu His Asn Glu Gly Ala Gly Leu Gln His Leu Ala Leu
        290                 295                 300

Met Ser Ala Asp Ile Phe Arg Thr Leu Arg Glu Met Arg Lys Arg Ser
305                 310                 315                 320

Gly Val Gly Gly Phe Glu Phe Met Pro Ser Pro Pro Val Thr Tyr Tyr
                325                 330                 335

Arg Asn Leu Lys Asn Arg Val Gly Asp Val Leu Ser Asp Glu Gln Ile
                340                 345                 350

Lys Glu Cys Glu Glu Leu Gly Ile Leu Val Asp Arg Asp Gln Gly
            355                 360                 365

Thr Leu Leu Gln Ile Phe Thr Lys Pro Ile Gly Asp Arg Pro Thr Ile
        370                 375                 380

Phe Ile Glu Ile Ile Gln Arg Val Gly Cys Met Leu Lys Asp Glu Glu
385                 390                 395                 400

Gly Lys Glu Tyr Gln Lys Gly Gly Cys Gly Gly Phe Gly Lys Gly Asn
                405                 410                 415

Phe Ser Glu Leu Phe Lys Ser Ile Glu Glu Tyr Glu Lys Thr Leu Glu
```

Thr Arg Arg Thr Ala
              435

<210> SEQ ID NO 25
<211> LENGTH: 152
<212> TYPE: PRT
<213> ORGANISM: Zea mays

<400> SEQUENCE: 25

Met Pro Pro Thr Pro Thr Ala Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe His Thr Leu Ala Phe
            35                  40                  45

His His Val Glu Leu Trp Cys Ala Asp Ala Ala Ser Ala Ala Gly Arg
        50                  55                  60

Phe Ser Phe Gly Leu Gly Ala Pro Leu Ala Ala Arg Ser Asp Leu Ser
65                  70                  75                  80

Thr Gly Asn Ser Ala His Ala Ser Leu Leu Arg Ser Gly Ser Leu
                85                  90                  95

Ser Phe Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
            115                 120                 125

Asp His Gly Leu Ala Val Arg Ala Val Ala Leu Arg Val Ala Asp Ala
            130                 135                 140

Glu Asp Ala Phe Arg Ala Ser Val
145                 150

<210> SEQ ID NO 26
<211> LENGTH: 158
<212> TYPE: PRT
<213> ORGANISM: Oryza sativa

<400> SEQUENCE: 26

Met Pro Pro Thr Pro Thr Pro Thr Ala Thr Thr Gly Ala Val Ser Ala
1               5                   10                  15

Ala Ala Ala Ala Gly Glu Asn Ala Gly Phe Arg Leu Val Gly His Arg
            20                  25                  30

Arg Phe Val Arg Ala Asn Pro Arg Ser Asp Arg Phe Gln Ala Leu Ala
            35                  40                  45

Phe His His Val Glu Leu Trp Cys Ala Asp Ala Ala Ser Ala Ala Gly
        50                  55                  60

Arg Phe Ala Phe Ala Leu Gly Ala Pro Leu Ala Ala Arg Ser Asp Leu
65                  70                  75                  80

Ser Thr Gly Asn Ser Ala His Ala Ser Leu Leu Arg Ser Ala Ser
                85                  90                  95

Val Ala Phe Leu Phe Thr Ala Pro Tyr Gly Gly Asp His Gly Val Gly
            100                 105                 110

Ala Asp Ala Ala Thr Thr Ala Ser Ile Pro Ser Phe Ser Pro Gly Ala
            115                 120                 125

Ala Arg Arg Phe Ala Ala Asp His Gly Leu Ala Val His Ala Val Ala
            130                 135                 140

Leu Arg Val Ala Asp Ala Ala Asp Ala Phe Arg Ala Ser Val

```
145                 150                 155

<210> SEQ ID NO 27
<211> LENGTH: 152
<212> TYPE: PRT
<213> ORGANISM: Avena sativa

<400> SEQUENCE: 27

Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
            20                  25                  30

Pro Arg Ser Asp Arg Phe Pro Val Leu Ser Phe His His Val Glu Leu
        35                  40                  45

Trp Cys Ala Asp Ala Ala Ser Ala Ala Gly Arg Phe Ser Phe Ala Leu
50                  55                  60

Gly Ala Pro Leu Ala Ala Arg Ser Asp Leu Ser Thr Gly Asn Ser Ala
65                  70                  75                  80

His Ala Ser Leu Leu Leu Arg Ser Gly Ala Leu Ala Phe Leu Phe Thr
                85                  90                  95

Ala Pro Tyr Ala Pro Pro Gln Glu Ala Ala Thr Ala Ala Ala Ala Thr
            100                 105                 110

Ala Ser Ile Pro Ser Phe Ser Ala Asp Ala Ala Arg Thr Phe Ala Ala
        115                 120                 125

Ala His Gly Leu Ala Val Arg Ser Val Gly Val Arg Val Ala Asp Ala
    130                 135                 140

Ala Glu Ala Phe Arg Val Ser Val
145                 150

<210> SEQ ID NO 28
<211> LENGTH: 146
<212> TYPE: PRT
<213> ORGANISM: Hordeum vulgare

<400> SEQUENCE: 28

Met Pro Pro Thr Pro Thr Thr Pro Ala Ala Thr Gly Ala Ala Ala Ala
1               5                   10                  15

Val Thr Pro Glu His Ala Arg Pro His Arg Met Val Arg Phe Asn Pro
            20                  25                  30

Arg Ser Asp Arg Phe His Thr Leu Ser Phe His His Val Glu Phe Trp
        35                  40                  45

Cys Ala Asp Ala Ala Ser Ala Ala Gly Arg Phe Ala Phe Ala Leu Gly
50                  55                  60

Ala Pro Leu Ala Ala Arg Ser Asp Leu Ser Thr Gly Asn Ser Ala His
65                  70                  75                  80

Ala Ser Gln Leu Leu Arg Ser Gly Ser Leu Ala Phe Leu Phe Thr Ala
                85                  90                  95

Pro Tyr Ala Asn Gly Cys Asp Ala Thr Ala Ser Leu Pro Ser Phe
            100                 105                 110

Ser Ala Asp Ala Ala Arg Arg Phe Ser Ala Asp His Gly Ile Ala Val
        115                 120                 125

Arg Ser Val Ala Leu Arg Val Ala Asp Ala Ala Glu Ala Phe Arg Ala
    130                 135                 140

Ser Arg
145
```

<210> SEQ ID NO 29
<211> LENGTH: 148
<212> TYPE: PRT
<213> ORGANISM: Triticum aestivum

<400> SEQUENCE: 29

Met Pro Pro Thr Pro Thr Thr Pro Ala Ala Thr Gly Ala Gly Ala Ala
1               5                   10                  15

Ala Ala Val Thr Pro Glu His Ala Arg Pro Arg Arg Met Val Arg Phe
            20                  25                  30

Asn Pro Arg Ser Asp Arg Phe His Thr Leu Ser Phe His His Val Glu
        35                  40                  45

Phe Trp Cys Ala Asp Ala Ala Ser Ala Ala Gly Arg Phe Ala Phe Ala
50                  55                  60

Leu Gly Ala Pro Leu Ala Ala Arg Ser Asp Leu Ser Thr Gly Asn Ser
65                  70                  75                  80

Val His Ala Ser Gln Leu Leu Arg Ser Gly Asn Leu Ala Phe Leu Phe
                85                  90                  95

Thr Ala Pro Tyr Ala Asn Gly Cys Asp Ala Ala Thr Ala Ser Leu Pro
            100                 105                 110

Ser Phe Ser Ala Asp Ala Ala Arg Arg Phe Ser Ala Asp His Gly Leu
        115                 120                 125

Ala Val Arg Ser Ile Ala Leu Arg Val Ala Asp Ala Ala Glu Ala Phe
130                 135                 140

Arg Ala Ser Val
145

<210> SEQ ID NO 30
<211> LENGTH: 94
<212> TYPE: PRT
<213> ORGANISM: Acinetobacter sp

<400> SEQUENCE: 30

Met Asp Ile Leu Glu Asn Pro Leu Glu Leu Cys Gly Phe Ala Phe Ile
1               5                   10                  15

Glu Phe Val Ser Lys Glu Asn Glu Leu Asp Pro Ile Phe Glu Thr Ile
            20                  25                  30

Gly Phe Ser Lys Val Ala Lys His Lys Ser Lys Ala Tyr Leu Trp
        35                  40                  45

Arg Gln Gly Asn Ile Asn Ile Leu Asn Tyr Gln Pro Glu Ser Tyr
50                  55                  60

Ala Ser Phe Phe Phe Asn Glu His Gly Pro Ser Ala Cys Ala Met Gly
65                  70                  75                  80

Phe Lys Thr Arg Asp Ala Ala Lys Ala Phe Lys Lys Ala Val
                85                  90

<210> SEQ ID NO 31
<211> LENGTH: 101
<212> TYPE: PRT
<213> ORGANISM: Pseudomonas syringae

<400> SEQUENCE: 31

Met Ala Asp Leu Tyr Glu Ala Asp Lys Tyr Glu Asn Pro Met Gly Leu
1               5                   10                  15

Met Gly Phe Glu Phe Ile Glu Phe Ala Ser Pro Thr Pro Asn Ser Leu
            20                  25                  30

Glu Pro Val Phe Gln Met Met Gly Phe Thr Lys Val Ala Thr His Arg
        35                  40                  45

```
Ser Lys Asp Val Thr Leu Tyr Arg Gln Gly Ala Ile Asn Leu Ile Leu
    50                  55                  60

Asn Asn Glu Pro His Ser Leu Ala Ser Tyr Phe Ala Ala Glu His Gly
65                  70                  75                  80

Pro Ser Val Cys Gly Met Ala Phe Arg Val Lys Asp Ala Gln His Ala
                85                  90                  95

Tyr Asn Arg Ala Leu
            100

<210> SEQ ID NO 32
<211> LENGTH: 94
<212> TYPE: PRT
<213> ORGANISM: Legionella pneumophila

<400> SEQUENCE: 32

Met Gln Asn Asn Asn Pro Cys Gly Leu Asp Gly Phe Ala Phe Leu Glu
 1               5                  10                  15

Phe Ser Gly Pro Asp Arg Asn Lys Leu His Gln Gln Phe Ser Glu Met
            20                  25                  30

Gly Phe Gln Ala Val Ala His His Lys Asn Gln Asp Ile Thr Leu Phe
        35                  40                  45

Lys Gln Gly Glu Ile Gln Phe Ile Val Asn Ala Ala Ser His Cys Gln
    50                  55                  60

Ala Glu Ala His Ala Ser Thr His Gly Pro Gly Ala Cys Ala Met Gly
65                  70                  75                  80

Phe Lys Val Lys Asp Ala Lys Ala Ala Phe Gln His Ala Ile
                85                  90

<210> SEQ ID NO 33
<211> LENGTH: 87
<212> TYPE: PRT
<213> ORGANISM: Ralstonia solanacearum

<400> SEQUENCE: 33

Met Ser Ala Val Thr Thr Ala Gly Phe Ala Phe Val Glu Phe Val Cys
 1               5                  10                  15

Ala Glu Pro Asn Glu Leu Val Ala Leu Phe Gly Lys Leu Gly Phe Lys
            20                  25                  30

Ala Leu Gly Gln His Ala Gln Thr Gly Ala Val Leu Leu Arg Gln Asn
        35                  40                  45

Glu Ala Val Leu Ile Val Asn Pro Ala Pro Asn Pro Phe Arg Asp Val
    50                  55                  60

His Gly Ala Ser Ala Arg Ala Ile Ala Ile Asn Val Asp Asn Ala Ala
65                  70                  75                  80

Asn Ala Leu Ala Gln Ala Leu
                85

<210> SEQ ID NO 34
<211> LENGTH: 130
<212> TYPE: PRT
<213> ORGANISM: Bacillus thuringiensis

<400> SEQUENCE: 34

Met Val Leu Ser Met Asn His Leu Ile Tyr Leu Gln Gly Asp Glu Asp
 1               5                  10                  15

Phe Met Lys Gln Lys Ser Met Asp Thr Leu Ala Ala Gln Met Glu Asp
            20                  25                  30
```

```
Phe Phe Pro Val Arg Asp Val Asp His Leu Glu Phe Tyr Val Gly Asn
         35                  40                  45

Ala Lys Gln Ser Ser Tyr Tyr Leu Ala Arg Ala Phe Gly Phe Lys Ile
 50                  55                  60

Val Ala Tyr Ser Gly Leu Glu Thr Gly Asn Arg Glu Lys Val Ser Tyr
 65                  70                  75                  80

Val Leu Val Gln Lys Asn Met Arg Phe Val Val Ser Gly Ala Leu Ser
                 85                  90                  95

Ser Asp Asn Arg Ile Ala Glu Phe Val Lys Thr His Gly Asp Gly Val
                100                 105                 110

Lys Asp Val Ala Leu Leu Val Asp Asp Val Asp Lys Ala Tyr Ser Glu
            115                 120                 125

Ala Val
    130

<210> SEQ ID NO 35
<211> LENGTH: 103
<212> TYPE: PRT
<213> ORGANISM: Chloroflexus aurantiacus

<400> SEQUENCE: 35

Met Cys Ser Ala Asp Pro Leu Glu Leu Leu Gly Ile Asp Tyr Val Glu
 1               5                  10                  15

Phe Tyr Val Ser Asn Ala Arg Gln Ala Ala His Phe Tyr Arg Thr Thr
                20                  25                  30

Leu Gly Leu Arg Pro Val Ala Tyr Ala Gly Leu Glu Thr Gly Val Arg
             35                  40                  45

Asp Arg Ala Ser Tyr Val Leu Glu Arg Arg Asn Val Arg Phe Val Leu
 50                  55                  60

Thr Ala Pro Leu Leu Pro Asp His Pro Ile Ala Gln His Ile Ala His
 65                  70                  75                  80

His Gly Asp Gly Val Lys Asp Ile Ala Leu Arg Val Arg Asp Ala Val
                 85                  90                  95

Thr Ala Tyr Glu Thr Ala Val
                100

<210> SEQ ID NO 36
<211> LENGTH: 115
<212> TYPE: PRT
<213> ORGANISM: Catenulispora acidphila

<400> SEQUENCE: 36

Met Thr Glu Thr Ala Thr Ala Ser Ala Ala Ser Ala Thr Ala Thr Lys
 1               5                  10                  15

Asp Pro Phe Pro Val Lys Gly Met Asp Ala Val Val Phe Ala Val Gly
                20                  25                  30

Asn Ala Lys Gln Ala Ala His Tyr Tyr Ser Thr Ala Phe Gly Met Arg
             35                  40                  45

Val Val Ala Tyr Ser Gly Pro Glu Thr Gly Arg Ala Asp Arg Val Ala
 50                  55                  60

Tyr Val Leu Glu Ser Gly Ser Ala Arg Phe Val Phe Lys Gly Ser Val
 65                  70                  75                  80

Arg Pro Gly Thr Glu Ile Ala Leu His Val Ala Glu His Gly Asp Gly
                 85                  90                  95

Val Thr Asp Leu Ala Ile Ala Val Pro Asp Val Tyr Ala Tyr Glu
                100                 105                 110
```

```
Tyr Ala Val
        115

<210> SEQ ID NO 37
<211> LENGTH: 128
<212> TYPE: PRT
<213> ORGANISM: Micromonospora aurantiaca

<400> SEQUENCE: 37

Met Thr Gln Ala Ile Asp Arg Pro Gln Ser Thr Glu Glu Val Asp Val
 1               5                  10                  15

Asp Ala Leu Val Gly Ala Val Asp His Asp Ile Thr Arg Asp Pro Phe
            20                  25                  30

Pro Val Lys Gly Met Asp His Val His Phe Leu Val Gly Asn Ala Lys
        35                  40                  45

Gln Ala Ala His Tyr Tyr Ser Thr Ala Phe Gly Met Thr Cys Val Ala
    50                  55                  60

Tyr Arg Gly Pro Glu Gln Gly Tyr Arg Asp His Ala Gln Tyr Val Leu
65                  70                  75                  80

Thr Ser Gly Ser Ala Arg Phe Val Leu Thr Gly Ala Val Arg Pro Asp
                85                  90                  95

Ala Asp Gly Ala Glu His Val Ala Lys His Ser Asp Gly Val Ser Asp
            100                 105                 110

Ile Ala Leu Glu Val Pro Asp Val Asp Ala Ala Tyr Ala His Ala Val
        115                 120                 125

<210> SEQ ID NO 38
<211> LENGTH: 128
<212> TYPE: PRT
<213> ORGANISM: Salinispora tropica

<400> SEQUENCE: 38

Met Thr Gln Ala Ile Asp Arg Pro Gln Thr Ser Asp Glu Val Asp Ala
 1               5                  10                  15

Asp Leu Leu Val Gly Ala Val Asp His Asp Ile Ser His Asp Pro Phe
            20                  25                  30

Pro Val Lys Gly Leu Asp His Val Gln Phe Leu Val Gly Asn Ala Lys
        35                  40                  45

Gln Ala Ala His Tyr Tyr Ser Thr Ala Phe Gly Met Thr Cys Val Ala
    50                  55                  60

Tyr Arg Gly Pro Glu Gln Gly Tyr Arg Asp His Ala Gln Tyr Val Leu
65                  70                  75                  80

Thr Ser Gly Ser Ala Arg Phe Val Leu Thr Gly Ala Val Arg Pro Asp
                85                  90                  95

Ala Ala Gly Ala Glu Gln Val Ala Arg His Ser Asp Gly Val Cys Asp
            100                 105                 110

Ile Ala Leu Glu Val Pro Asp Val Asp Ala Ala His Ala His Ala Ile
        115                 120                 125

<210> SEQ ID NO 39
<211> LENGTH: 133
<212> TYPE: PRT
<213> ORGANISM: Geodermatophilus obscurus

<400> SEQUENCE: 39

Met Ser Leu Glu Gln Ala Leu Asn Asp Asp Glu Arg Leu Ala Gln Leu
 1               5                  10                  15

Asp Leu Asp Gln Leu Lys Gln Leu Val Gly Leu Val Glu Tyr Asp Ala
```

```
            20                  25                  30
Ser Gly Asp Pro Phe Pro Val Ser Gly Trp Asp Ala Leu Val Trp Val
        35                  40                  45

Val Gly Asn Ala Thr Gln Ala Ala His Phe His Gln Ser Ala Phe Gly
    50                  55                  60

Met Glu Leu Val Ala Tyr Ser Gly Pro Glu Thr Gly Asn Arg Asp His
65                  70                  75                  80

Leu Ala Tyr Val Leu Glu Ser Gly Ala Ala Arg Phe Val Val Arg Gly
                85                  90                  95

Ala Tyr Asp Pro Ala Ser Pro Leu Ala Asp His His Arg Lys His Gly
            100                 105                 110

Asp Gly Ile Val Asp Ile Ala Leu Ser Val Pro Asp Val Asp Arg Cys
        115                 120                 125

Ile Ala His Ala Ala
        130

<210> SEQ ID NO 40
<211> LENGTH: 132
<212> TYPE: PRT
<213> ORGANISM: Kribbella flavida

<400> SEQUENCE: 40

Met Thr Ser Thr Asp Leu Thr Pro Ala Glu Leu Asp Ala Asp Leu Asp
1               5                   10                  15

Leu Asp Gln Leu Lys Gln Leu Val Gly Leu Val Pro Tyr Asp Glu Ser
            20                  25                  30

Thr Asp Pro Phe Pro Val Thr Ala Met Asp Ala Val Phe Val Val
        35                  40                  45

Gly Asn Ala Thr Gln Thr Ala Lys Phe Tyr Gln Leu Ala Phe Gly Met
    50                  55                  60

Asp Leu Val Ala Tyr Ala Gly Pro Glu Thr Gly Ser Lys Asp Ala Lys
65                  70                  75                  80

Tyr Phe Val Leu Lys Ala Gly Ser Ala Arg Phe Val Ile Ser Gly Gly
                85                  90                  95

Val Arg Pro Asp Ser Pro Leu Leu Asp His His Arg Lys His Gly Asp
            100                 105                 110

Gly Val Val Asp Leu Ala Leu Glu Val Pro Asp Val Asp Lys Cys Val
        115                 120                 125

Lys His Ala Arg
        130

<210> SEQ ID NO 41
<211> LENGTH: 117
<212> TYPE: PRT
<213> ORGANISM: Streptomyces avermitilis

<400> SEQUENCE: 41

Met Thr Gln Thr Thr His His Thr Pro Asp Thr Ala Arg Gln Ala Asp
1               5                   10                  15

Pro Phe Pro Val Lys Gly Met Asp Ala Val Phe Ala Val Gly Asn
            20                  25                  30

Ala Lys Gln Ala Ala His Tyr Ser Thr Ala Phe Gly Met Gln Leu Val
            35                  40                  45

Ala Tyr Ser Gly Pro Glu Asn Gly Ser Arg Glu Thr Ala Ser Tyr Val
        50                  55                  60

Leu Thr Asn Gly Ser Ala Arg Phe Val Leu Thr Ser Val Ile Lys Pro
```

```
                65                  70                  75                  80
Ala Thr Pro Trp Gly His Phe Leu Ala Asp His Val Ala Glu His Gly
                    85                  90                  95

Asp Gly Val Val Asp Leu Ala Ile Glu Val Pro Asp Ala Arg Ala Ala
                100                 105                 110

His Ala Tyr Ala Ile
        115

<210> SEQ ID NO 42
<211> LENGTH: 142
<212> TYPE: PRT
<213> ORGANISM: Ostreoccoccus tauri

<400> SEQUENCE: 42

Met Thr Thr Ser Ala Ser Gly Arg Lys Leu Val Gly His Ala Asn Phe
  1               5                  10                  15

Val Arg Cys Asn Pro Leu Ser Asp Ala Phe Glu Cys Val Gly Phe Asp
                 20                  25                  30

His Val Glu Phe Trp Cys Gly Asp Ala Thr Asn Ala Ala Ser Arg Phe
             35                  40                  45

Gly Val Gly Leu Gly Met Ser Leu Arg Ala Lys Ser Asp Ala Ser Thr
         50                  55                  60

Gly Asn Gly Ile Tyr Ala Ser Tyr Ala Met Lys Ser His Asp Leu Thr
 65                  70                  75                  80

Phe Val Phe Thr Ala Pro Tyr Gly Asp Asp Glu Arg Ala Val Gly Cys
                 85                  90                  95

Gly Gly Ser Ser Val Asn Val Pro His Pro Gly Asn Glu Arg Gly Ala
                100                 105                 110

Met Met Arg Phe Phe Glu Arg His Gly Leu Ala Ala Arg Ala Val Gly
            115                 120                 125

Leu Arg Val Gly Asp Ala Arg Ala Ala Tyr Glu Glu Ala Met
        130                 135                 140

<210> SEQ ID NO 43
<211> LENGTH: 152
<212> TYPE: PRT
<213> ORGANISM: Daucus carota

<400> SEQUENCE: 43

Met Gly Lys Lys Gln Ser Glu Ala Glu Ile Leu Ser Ser Asn Ser Ser
  1               5                  10                  15

Asn Thr Ser Pro Ala Thr Phe Lys Leu Val Gly Phe Asn Asn Phe Val
                 20                  25                  30

Arg Ala Asn Pro Lys Ser Asp His Phe Ala Val Lys Arg Phe His His
             35                  40                  45

Ile Glu Phe Trp Cys Gly Asp Ala Thr Asn Thr Ser Arg Arg Phe Ser
         50                  55                  60

Trp Gly Leu Gly Met Pro Leu Val Ala Lys Ser Asp Leu Ser Thr Gly
 65                  70                  75                  80

Asn Ser Val His Ala Ser Tyr Leu Val Arg Ser Ala Asn Leu Ser Phe
                 85                  90                  95

Val Phe Thr Ala Pro Tyr Ser Pro Ser Thr Thr Ser Ser Gly Ser
                100                 105                 110

Ala Ala Ile Pro Ser Phe Ser Ala Ser Gly Phe His Ser Phe Ala Ala
            115                 120                 125

Lys His Gly Leu Ala Val Arg Ala Ile Ala Leu Glu Val Ala Asp Val
```

Ala Ala Ala Phe Glu Ala Ser Val
145                 150

<210> SEQ ID NO 44
<211> LENGTH: 144
<212> TYPE: PRT
<213> ORGANISM: Solenostemon scutellarioides

<400> SEQUENCE: 44

Met Gly Gln Glu Ser Thr Ala Ala Ala Val Val Pro Ala Glu Phe
1               5                   10                  15

Lys Leu Val Gly His Lys Asn Phe Val Arg Ser Asn Pro Met Ser Asp
            20                  25                  30

His Phe Pro Val His Arg Phe His Val Glu Phe Trp Cys Gly Asp
        35                  40                  45

Ala Thr Asn Thr Ser Arg Arg Phe Ser Trp Gly Leu Gly Met Pro Leu
        50                  55                  60

Val Ala Lys Ser Asp Leu Ser Thr Gly Asn Ser Ala His Ala Ser Tyr
65                  70                  75                  80

Leu Leu Arg Ser Gly Glu Leu Ser Phe Val Phe Thr Ala Pro Tyr Ser
                85                  90                  95

Pro Ser Leu Ala Glu Pro Ser Ser Ala Ser Ile Pro Thr Phe Ser Phe
            100                 105                 110

Ser Asp His Arg Ala Phe Thr Ser Ser His Gly Leu Ala Val Arg Ala
            115                 120                 125

Val Ala Ile Gln Val Asp Ser Ala Ser Ser Ala Tyr Ser Ala Ala Val
            130                 135                 140

<210> SEQ ID NO 45
<211> LENGTH: 159
<212> TYPE: PRT
<213> ORGANISM: Brassica rapa

<400> SEQUENCE: 45

Met Gly His Glu Asn Ala Ala Val Ser Glu Asn Gln His His Asp Asp
1               5                   10                  15

Ala Ala Thr Thr Ser Ala Ser Pro Gly Phe Lys Leu Val Gly Phe Ser
            20                  25                  30

Lys Phe Val Arg Lys Asn Pro Lys Ser Asp Lys Phe Lys Val Lys Arg
            35                  40                  45

Phe His His Ile Glu Phe Trp Cys Gly Asp Ala Thr Asn Val Ala Arg
        50                  55                  60

Arg Phe Ser Trp Gly Leu Gly Met Arg Phe Ser Ala Lys Ser Asp Leu
65                  70                  75                  80

Ser Thr Gly Asn Met Val His Ala Ser Tyr Leu Leu Thr Ser Gly Asp
                85                  90                  95

Leu Arg Phe Leu Phe Thr Ala Pro Tyr Ser Pro Ser Leu Ser Ala Gly
            100                 105                 110

Glu Asn Pro Pro Thr Thr Thr Ala Ser Ile Pro Ser Phe Asp His Val
            115                 120                 125

Thr Tyr Arg Ser Phe Phe Ser Ser His Gly Leu Gly Val Arg Ala Val
            130                 135                 140

Ala Val Glu Val Glu Asp Ala Glu Ala Ala Phe Ser Ile Ser Val
145                 150                 155

-continued

<210> SEQ ID NO 46
<211> LENGTH: 140
<212> TYPE: PRT
<213> ORGANISM: Coptis japonica

<400> SEQUENCE: 46

Met Val Pro Ser Thr Ala Ser Asn Leu Lys Leu Val Gly His Thr Asn
1               5                   10                  15

Phe Val His Asn Asn Pro Lys Ser Asp Lys Phe His Val Lys Lys Phe
            20                  25                  30

His His Ile Glu Phe Trp Ser Thr Asp Ala Thr Asn Thr Ala Arg Arg
        35                  40                  45

Phe Ser Trp Gly Leu Gly Met Pro Met Val Ala Lys Ser Asp Leu Ser
    50                  55                  60

Thr Gly Asn Met Val His Ala Ser Tyr Leu Leu Arg Ser Gly Glu Leu
65                  70                  75                  80

Asn Phe Leu Phe Thr Ala Pro Tyr Ser Pro Ser Ile Ala Gly Asn Thr
                85                  90                  95

Leu Thr His Thr Ala Ser Ile Pro Thr Tyr Ser His Asn Leu Ala Arg
            100                 105                 110

Leu Phe Ala Ser Thr His Gly Leu Ala Val Arg Ala Ile Ala Ile Glu
        115                 120                 125

Val Gln Asp Ala Glu Leu Ala Tyr Asn Ile Ser Val
    130                 135                 140

<210> SEQ ID NO 47
<211> LENGTH: 155
<212> TYPE: PRT
<213> ORGANISM: Glycine max

<400> SEQUENCE: 47

Met Pro Ile Pro Met Cys Asn Glu Ile Gln Ala Gln Ala Gln Ala Gln
1               5                   10                  15

Ala Gln Ala Gln Pro Gly Phe Lys Leu Val Gly Phe Lys Asn Phe Val
            20                  25                  30

Arg Thr Asn Pro Lys Ser Asp Arg Phe Gln Val Asn Arg Phe His His
        35                  40                  45

Ile Glu Phe Trp Cys Thr Asp Ala Thr Asn Ala Ser Arg Arg Phe Ser
    50                  55                  60

Trp Gly Leu Gly Met Pro Ile Val Ala Lys Ser Asp Leu Ser Thr Gly
65                  70                  75                  80

Asn Gln Ile His Ala Ser Tyr Leu Leu Arg Ser Gly Asp Leu Ser Phe
                85                  90                  95

Leu Phe Ser Ala Pro Tyr Ser Pro Ser Leu Ser Ala Gly Ser Ser Ala
            100                 105                 110

Ala Ser Ser Ala Ser Ile Pro Ser Phe Asp Ala Ala Thr Cys Leu Ala
        115                 120                 125

Phe Ala Ala Lys His Gly Phe Gly Val Arg Ala Ile Ala Leu Glu Val
    130                 135                 140

Ala Asp Ala Glu Ala Ala Phe Ser Ala Ser Val
145                 150                 155

<210> SEQ ID NO 48
<211> LENGTH: 148
<212> TYPE: PRT
<213> ORGANISM: Vitis vinifera

<400> SEQUENCE: 48

```
Met Gly Lys Gln Asn Thr Thr Asn Asn Pro Ala Pro Gly Phe Lys
1               5                   10                  15

Leu Val Gly Phe Ser Asn Phe Leu Arg Thr Asn Pro Met Ser Asp Arg
            20                  25                  30

Phe Gly Val Lys Arg Phe His His Ile Glu Phe Trp Ser Thr Asp Ala
            35                  40                  45

Thr Asn Leu Ala Arg Arg Phe Ser Trp Gly Leu Gly Met Pro Ile Val
50                      55                  60

Ala Lys Ser Asp Leu Ser Thr Gly Asn Val Ile His Ala Ser Tyr Leu
65                  70                  75                  80

Thr Arg Ser Gly Asp Leu Asn Phe Leu Phe Thr Ala Pro Tyr Ser Pro
                85                  90                  95

Ser Ile Ala Gly Asp Leu Glu Asn Ala Ala Thr Ala Ser Ile Pro
                100                 105                 110

Ser Phe Asp His Ser Ala Cys His Ala Phe Ala Ala Ser His Gly Leu
            115                 120                 125

Gly Val Arg Ala Ile Ala Ile Glu Val Asp Asp Ala Glu Gly Ala Phe
            130                 135                 140

His Thr Ser Val
145

<210> SEQ ID NO 49
<211> LENGTH: 146
<212> TYPE: PRT
<213> ORGANISM: Medicago truncatula

<400> SEQUENCE: 49

Met Ala Ile Glu Thr Glu Thr Gln Thr Gln Thr Gln Thr Gly Phe Lys
1               5                   10                  15

Leu Val Gly Phe Lys Asn Phe Val Arg Ala Asn Pro Lys Ser Asp Arg
            20                  25                  30

Phe Asn Val Lys Arg Phe His His Val Glu Phe Trp Cys Thr Asp Ala
            35                  40                  45

Thr Asn Thr Ala Arg Arg Phe Ser His Gly Leu Gly Met Pro Ile Val
50                      55                  60

Ala Lys Ser Asp Leu Ser Thr Gly Asn Leu Thr His Ala Ser Tyr Leu
65                  70                  75                  80

Leu Arg Ser Gly Asp Leu Asn Phe Leu Phe Ser Ala Ala Tyr Ser Pro
                85                  90                  95

Ser Ile Ser Leu Ser Ser Pro Ser Ser Thr Ala Ala Ile Pro Thr Phe
                100                 105                 110

Ser Ala Ser Thr Cys Phe Ser Phe Ser Ala Ser His Gly Leu Ala Val
            115                 120                 125

Arg Ala Val Ala Val Glu Val Glu Asp Ala Glu Val Ala Phe Thr Thr
            130                 135                 140

Ser Val
145

<210> SEQ ID NO 50
<211> LENGTH: 111
<212> TYPE: PRT
<213> ORGANISM: Homo sapiens

<400> SEQUENCE: 50

Met Thr Thr Tyr Ser Asp Lys Gly Ala Lys Pro Glu Arg Gly Arg Phe
1               5                   10                  15
```

-continued

Leu His Phe His Ser Val Thr Phe Trp Val Gly Asn Ala Lys Gln Ala
            20                  25                  30

Ala Ser Phe Tyr Cys Ser Lys Met Gly Phe Glu Pro Leu Ala Tyr Arg
            35                  40                  45

Gly Leu Glu Thr Gly Ser Arg Glu Val Val Ser His Val Ile Lys Gln
 50                  55                  60

Gly Lys Ile Val Phe Val Leu Ser Ser Ala Leu Asn Pro Trp Asn Lys
65                   70                  75                  80

Glu Met Gly Asp His Leu Val Lys His Gly Asp Gly Val Lys Asp Ile
                85                  90                  95

Ala Phe Glu Val Glu Asp Cys Asp Tyr Ile Val Gln Lys Ala Arg
            100                 105                 110

<210> SEQ ID NO 51
<211> LENGTH: 111
<212> TYPE: PRT
<213> ORGANISM: Rattus norvegicus

<400> SEQUENCE: 51

Met Thr Thr Tyr Ser Asn Lys Gly Pro Lys Pro Glu Arg Gly Arg Phe
1                5                  10                  15

Leu His Phe His Ser Val Thr Phe Trp Val Gly Asn Ala Lys Gln Ala
            20                  25                  30

Ala Ser Phe Tyr Cys Asn Lys Met Gly Phe Glu Pro Leu Ala Tyr Lys
            35                  40                  45

Gly Leu Glu Thr Gly Ser Arg Glu Val Val Ser His Val Ile Lys Gln
 50                  55                  60

Gly Lys Ile Val Phe Val Leu Cys Ser Ala Leu Asn Pro Trp Asn Lys
65                   70                  75                  80

Glu Met Gly Asp His Leu Val Lys His Gly Asp Gly Val Lys Asp Ile
                85                  90                  95

Ala Phe Glu Val Glu Asp Cys Gly His Ile Val Gln Lys Ala Arg
            100                 105                 110

<210> SEQ ID NO 52
<211> LENGTH: 111
<212> TYPE: PRT
<213> ORGANISM: Mus musculus

<400> SEQUENCE: 52

Met Thr Thr Tyr Asn Asn Lys Gly Pro Lys Pro Glu Arg Gly Arg Phe
1                5                  10                  15

Leu His Phe His Ser Val Thr Phe Trp Val Gly Asn Ala Lys Gln Ala
            20                  25                  30

Ala Ser Phe Tyr Cys Asn Lys Met Gly Phe Glu Pro Leu Ala Tyr Arg
            35                  40                  45

Gly Leu Glu Thr Gly Ser Arg Glu Val Val Ser His Val Ile Lys Gln
 50                  55                  60

Gly Lys Ile Val Phe Val Leu Cys Ser Ala Leu Asn Pro Trp Asn Lys
65                   70                  75                  80

Glu Met Gly Asp His Leu Val Lys His Gly Asp Gly Val Lys Asp Ile
                85                  90                  95

Ala Phe Glu Val Glu Asp Cys Asp His Ile Val Gln Lys Ala Arg
            100                 105                 110

<210> SEQ ID NO 53

<211> LENGTH: 111
<212> TYPE: PRT
<213> ORGANISM: Bos taurus

<400> SEQUENCE: 53

```
Met Thr Thr Tyr Ser Asp Lys Gly Glu Lys Pro Glu Arg Gly Arg Phe
  1               5                  10                  15

Leu His Phe His Ser Val Thr Phe Trp Val Gly Asn Ala Lys Gln Ala
             20                  25                  30

Ala Ser Tyr Tyr Cys Ser Lys Leu Gly Phe Glu Pro Leu Ala Tyr Lys
         35                  40                  45

Gly Leu Glu Thr Gly Ser Arg Glu Val Val Ser His Val Val Lys Gln
 50                  55                  60

Gly Gln Ile Val Phe Val Phe Ser Ser Ala Leu Asn Pro Trp Asn Lys
 65                  70                  75                  80

Glu Met Gly Asp His Leu Val Lys His Gly Asp Gly Val Lys Asp Ile
                 85                  90                  95

Ala Phe Glu Val Glu Asp Cys Asp Tyr Ile Val Gln Lys Ala Arg
            100                 105                 110
```

<210> SEQ ID NO 54
<211> LENGTH: 440
<212> TYPE: PRT
<213> ORGANISM: Sorghum bicolor

<400> SEQUENCE: 54

```
Met Pro Pro Thr Pro Thr Thr Ala Ala Ala Thr Gly Ala Ala Val Ala
  1               5                  10                  15

Ala Ala Ser Ala Glu Gln Ala Ala Phe Arg Leu Val Gly His Arg Asn
             20                  25                  30

Phe Val Arg Val Asn Pro Arg Ser Asp Arg Phe His Thr Leu Ala Phe
         35                  40                  45

His His Val Glu Leu Trp Cys Ala Asp Ala Ala Ser Ala Ala Gly Arg
 50                  55                  60

Phe Ser Phe Gly Leu Gly Ala Pro Leu Ala Ala Arg Ser Asp Leu Ser
 65                  70                  75                  80

Thr Gly Asn Thr Ala His Ala Ser Leu Leu Leu Arg Ser Gly Ala Leu
                 85                  90                  95

Ala Phe Leu Phe Thr Ala Pro Tyr Ala His Gly Ala Asp Ala Ala Thr
            100                 105                 110

Ala Ser Leu Pro Ser Phe Ser Ala Ala Glu Ala Arg Arg Phe Ala Ala
        115                 120                 125

Asp His Gly Leu Ala Val Arg Ala Val Ala Leu Arg Val Ala Asp Ala
130                 135                 140

Glu Asp Ala Phe Arg Ala Ser Val Ala Ala Gly Ala Arg Pro Ala Phe
145                 150                 155                 160

Glu Pro Val Glu Leu Gly Leu Gly Phe Arg Leu Ala Glu Val Glu Leu
                165                 170                 175

Tyr Gly Asp Val Val Leu Arg Tyr Val Ser Tyr Pro Asp Asp Ala Asp
            180                 185                 190

Ala Ser Phe Leu Pro Gly Phe Gly Val Thr Ser Pro Gly Ala Ala
        195                 200                 205

Asp Tyr Gly Leu Arg Arg Phe Asp His Ile Val Gly Asn Val Pro Glu
    210                 215                 220

Leu Ala Pro Ala Ala Ala Tyr Phe Ala Gly Phe Thr Gly Phe His Glu
225                 230                 235                 240
```

```
Phe Ala Glu Phe Thr Ala Glu Asp Val Gly Thr Thr Glu Ser Gly Leu
            245                 250                 255

Asn Ser Met Val Leu Ala Asn Asn Ala Glu Asn Val Leu Leu Pro Leu
        260                 265                 270

Asn Glu Pro Val His Gly Thr Lys Arg Arg Ser Gln Ile Gln Thr Tyr
    275                 280                 285

Leu Asp His His Gly Gly Pro Gly Val Gln His Met Ala Leu Ala Ser
290                 295                 300

Asp Asp Val Leu Arg Thr Leu Arg Glu Met Gln Ala Arg Ser Ala Met
305                 310                 315                 320

Gly Gly Phe Glu Phe Met Ala Pro Pro Ala Pro Glu Tyr Tyr Asp Gly
                325                 330                 335

Val Arg Arg Ala Gly Asp Val Leu Thr Glu Ala Gln Ile Lys Glu
            340                 345                 350

Cys Gln Glu Leu Gly Val Leu Val Asp Arg Asp Asp Gln Gly Val Leu
        355                 360                 365

Leu Gln Ile Phe Thr Lys Pro Val Gly Asp Arg Pro Thr Leu Phe Leu
    370                 375                 380

Glu Ile Ile Gln Arg Ile Gly Cys Met Glu Lys Asp Glu Lys Gly Gln
385                 390                 395                 400

Glu Tyr Gln Lys Gly Cys Gly Gly Phe Gly Lys Gly Asn Phe Ser
                405                 410                 415

Gln Leu Phe Lys Ser Ile Glu Asp Tyr Glu Lys Ser Leu Glu Ala Lys
            420                 425                 430

Gln Ala Ala Ala Gln Gly Ser
        435                 440

<210> SEQ ID NO 55
<211> LENGTH: 10
<212> TYPE: PRT
<213> ORGANISM: Glycine max

<400> SEQUENCE: 55

Met Pro Ile Pro Met Cys Asn Glu Ile Gln
1               5                   10

<210> SEQ ID NO 56
<211> LENGTH: 10
<212> TYPE: PRT
<213> ORGANISM: Glycine max

<400> SEQUENCE: 56

Met Cys Asn Glu Ile Gln Ala Gln Ala Gln
1               5                   10

<210> SEQ ID NO 57
<211> LENGTH: 488
<212> TYPE: PRT
<213> ORGANISM: Glycine max

<400> SEQUENCE: 57

Met Pro Met Tyr Thr Pro Ser Leu Ser Ala Pro Ser Ser Asn His Ile
1               5                   10                  15

Gln Pro Ser Val Thr Leu Pro Leu Tyr Ile Thr Thr Lys Leu Asn
            20                  25                  30

Leu Lys Gln Gln His His Thr Thr Pro Met Pro Ile Pro Met Cys Asn
        35                  40                  45
```

-continued

Glu Ile Gln Ala Gln Ala Gln Ala Gln Pro Gly Phe Lys Leu
    50                  55                  60

Val Gly Phe Lys Asn Phe Val Arg Thr Asn Pro Lys Ser Asp Arg Phe
 65                  70                  75                  80

Gln Val Asn Arg Phe His His Ile Glu Phe Trp Cys Thr Asp Ala Thr
                 85                  90                  95

Asn Ala Ser Arg Arg Phe Ser Trp Gly Leu Gly Met Pro Ile Val Ala
            100                 105                 110

Lys Ser Asp Leu Ser Thr Gly Asn Gln Ile His Ala Ser Tyr Leu Leu
        115                 120                 125

Arg Ser Gly Asp Leu Ser Phe Leu Phe Ser Ala Pro Tyr Ser Pro Ser
    130                 135                 140

Leu Ser Ala Gly Ser Ser Ala Ala Ser Ser Ala Ser Ile Pro Ser Phe
145                 150                 155                 160

Asp Ala Ala Thr Cys Leu Ala Phe Ala Ala Lys His Gly Phe Gly Val
                165                 170                 175

Arg Ala Ile Ala Leu Glu Val Ala Asp Ala Glu Ala Ala Phe Ser Ala
            180                 185                 190

Ser Val Ala Lys Gly Ala Glu Pro Ala Ser Pro Val Leu Val Asp
        195                 200                 205

Asp Arg Thr Gly Phe Ala Glu Val Arg Leu Tyr Gly Asp Val Val Leu
    210                 215                 220

Arg Tyr Val Ser Tyr Lys Asp Ala Ala Pro Gln Ala Pro His Ala Asp
225                 230                 235                 240

Pro Ser Arg Trp Phe Leu Pro Gly Phe Glu Ala Ala Ser Ser Ser
                245                 250                 255

Ser Phe Pro Glu Leu Asp Tyr Gly Ile Arg Arg Leu Asp His Ala Val
            260                 265                 270

Gly Asn Val Pro Glu Leu Ala Pro Ala Val Arg Tyr Leu Lys Gly Phe
        275                 280                 285

Ser Gly Phe His Glu Phe Ala Glu Phe Thr Ala Glu Asp Val Gly Thr
    290                 295                 300

Ser Glu Ser Gly Leu Asn Ser Val Val Leu Ala Asn Asn Ser Glu Thr
305                 310                 315                 320

Val Leu Leu Pro Leu Asn Glu Pro Val Tyr Gly Thr Lys Arg Lys Ser
                325                 330                 335

Gln Ile Glu Thr Tyr Leu Glu His Asn Glu Gly Ala Gly Val Gln His
            340                 345                 350

Leu Ala Leu Val Thr His Asp Ile Phe Thr Thr Leu Arg Glu Met Arg
        355                 360                 365

Lys Arg Ser Phe Leu Gly Gly Phe Glu Phe Met Pro Ser Pro Pro Pro
    370                 375                 380

Thr Tyr Tyr Ala Asn Leu His Asn Arg Ala Ala Asp Val Leu Thr Val
385                 390                 395                 400

Asp Gln Ile Lys Gln Cys Glu Glu Leu Gly Ile Leu Val Asp Arg Asp
                405                 410                 415

Asp Gln Gly Thr Leu Leu Gln Ile Phe Thr Lys Pro Val Gly Asp Arg
            420                 425                 430

Pro Thr Ile Phe Ile Glu Ile Ile Gln Arg Ile Gly Cys Met Val Glu
        435                 440                 445

Asp Glu Glu Gly Lys Val Tyr Gln Lys Gly Ala Cys Gly Gly Phe Gly
    450                 455                 460

Lys Gly Asn Phe Ser Glu Leu Phe Lys Ser Ile Glu Glu Tyr Glu Lys

```
                465                 470                 475                 480
Thr Leu Glu Ala Lys Arg Thr Ala
                    485

<210> SEQ ID NO 58
<211> LENGTH: 86
<212> TYPE: PRT
<213> ORGANISM: Glycine max

<400> SEQUENCE: 58

Met Pro Met Tyr Thr Pro Ser Leu Ser Ala Pro Ser Ser Asn His Ile
1               5                   10                  15

Gln Pro Ser Val Thr Leu Pro Leu Tyr Ile Thr Thr Thr Lys Leu Asn
            20                  25                  30

Leu Lys Gln Gln His His Thr Thr Pro Met Pro Ile Pro Met Cys Asn
        35                  40                  45

Glu Ile Gln Ala Gln Ala Gln Ala Gln Ala Gln Pro Gly Phe Lys Leu
    50                  55                  60

Val Gly Phe Lys Asn Phe Val Arg Thr Asn Pro Lys Ser Asp Arg Phe
65                  70                  75                  80

Gln Val Asn Arg Phe His
                85

<210> SEQ ID NO 59
<211> LENGTH: 447
<212> TYPE: PRT
<213> ORGANISM: Glycine max

<400> SEQUENCE: 59

Met Pro Ile Pro Met Cys Asn Glu Ile Gln Ala Gln Ala Gln Ala Gln
1               5                   10                  15

Ala Gln Pro Gly Phe Lys Leu Val Gly Phe Lys Asn Phe Val Arg Thr
            20                  25                  30

Asn Pro Lys Ser Asp Arg Phe Gln Val Asn Arg Phe His His Ile Glu
        35                  40                  45

Phe Trp Cys Thr Asp Ala Thr Asn Ala Ser Arg Arg Phe Ser Trp Gly
    50                  55                  60

Leu Gly Met Pro Ile Val Ala Lys Ser Asp Leu Ser Thr Gly Asn Gln
65                  70                  75                  80

Ile His Ala Ser Tyr Leu Leu Arg Ser Gly Asp Leu Ser Phe Leu Phe
                85                  90                  95

Ser Ala Pro Tyr Ser Pro Ser Leu Ser Ala Gly Ser Ser Ala Ala Ser
            100                 105                 110

Ser Ala Ser Ile Pro Ser Phe Asp Ala Ala Thr Cys Leu Ala Phe Ala
        115                 120                 125

Ala Lys His Gly Phe Gly Val Arg Ala Ile Ala Leu Glu Val Ala Asp
    130                 135                 140

Ala Glu Ala Ala Phe Ser Ala Ser Val Ala Lys Gly Ala Glu Pro Ala
145                 150                 155                 160

Ser Pro Pro Val Leu Val Asp Asp Arg Thr Gly Phe Ala Glu Val Arg
                165                 170                 175

Leu Tyr Gly Asp Val Val Leu Arg Tyr Val Ser Tyr Lys Asp Ala Ala
            180                 185                 190

Pro Gln Ala Pro His Ala Asp Pro Ser Arg Trp Phe Leu Pro Gly Phe
        195                 200                 205

Glu Ala Ala Ala Ser Ser Ser Ser Phe Pro Glu Leu Asp Tyr Gly Ile
```

```
                    210                 215                 220
Arg Arg Leu Asp His Ala Val Gly Asn Val Pro Glu Leu Ala Pro Ala
225                 230                 235                 240

Val Arg Tyr Leu Lys Gly Phe Ser Gly Phe His Glu Phe Ala Glu Phe
                245                 250                 255

Thr Ala Glu Asp Val Gly Thr Ser Glu Ser Gly Leu Asn Ser Val Val
                260                 265                 270

Leu Ala Asn Asn Ser Glu Thr Val Leu Leu Pro Leu Asn Glu Pro Val
                275                 280                 285

Tyr Gly Thr Lys Arg Lys Ser Gln Ile Glu Thr Tyr Leu Glu His Asn
                290                 295                 300

Glu Gly Ala Gly Val Gln His Leu Ala Leu Val Thr His Asp Ile Phe
305                 310                 315                 320

Thr Thr Leu Arg Glu Met Arg Lys Arg Ser Phe Leu Gly Gly Phe Glu
                325                 330                 335

Phe Met Pro Ser Pro Pro Pro Thr Tyr Tyr Ala Asn Leu His Asn Arg
                340                 345                 350

Ala Ala Asp Val Leu Thr Val Asp Gln Ile Lys Gln Cys Glu Glu Leu
                355                 360                 365

Gly Ile Leu Val Asp Arg Asp Asp Gln Gly Thr Leu Leu Gln Ile Phe
                370                 375                 380

Thr Lys Pro Val Gly Asp Arg Pro Thr Ile Phe Ile Glu Ile Ile Gln
385                 390                 395                 400

Arg Ile Gly Cys Met Val Glu Asp Glu Glu Gly Lys Val Tyr Gln Lys
                405                 410                 415

Gly Ala Cys Gly Gly Phe Gly Lys Gly Asn Phe Ser Glu Leu Phe Lys
                420                 425                 430

Ser Ile Glu Glu Tyr Glu Lys Thr Leu Glu Ala Lys Arg Thr Ala
                435                 440                 445

<210> SEQ ID NO 60
<211> LENGTH: 2064
<212> TYPE: DNA
<213> ORGANISM: Glycine max

<400> SEQUENCE: 60
gtaataaaaa aagagagaag ccgcatcaac atcatccaat atatggacgt taaaagagcg     60
tcgtaatcca tttccatttc tcatctatct tcacttcctc gtcctcatcc tcatccacct    120
attctcaacc cagacgcaat gcccatgtac actccatcac tctccgcacc ctcctccaat    180
cacattcaac caagtgtcac actcccctta tatatcacaa ccaccaagct caatctcaag    240
cagcagcatc acaccacacc aatgccaata cccatgtgca acgaaattca agcccaagcc    300
caagcccaag cccaacctgg gtttaagctc gtcggtttca aaaacttcgt ccgaaccaat    360
cctaagtcgg accgctttca agtcaaccgc ttccaccaca tcgagttctg gtgcaccgat    420
gccaccaacg cctctcgccg attctcttgg ggacttggaa tgcctattgt ggcaaaatct    480
gatctctcca ccggaaacca aatccacgcc tcctacctcc tccgctccgg cgacctctcc    540
ttcctcttct ccgctcctta ctctcccctct ctctccgccg ctcctccgc tgcctcctcc    600 gcctccattc ccagtttcga cgccgccacc tgccttgcct tcgctgccaa acacggcttc    660
ggcgtccgcg ccatcgcctt ggaagtcgcc gacgcggaag ccgctttcag cgccagcgtc    720
gcgaaaggag ccgagccggc gtcgccgccg gttctcgtcg acgatcgcac cggcttcgcg    780
gaggtgcgcc tctacggcga cgtggtgctc cgctacgtca gctacaagga cgccgcgccg    840
```

```
caggcgccac acgcagatcc gtcgcggtgg ttcctgccgg gattcgaggc cgcggcgtcg    900
tcgtcttcgt ttccggagct ggactacggg atccggcggc tggaccacgc cgtcgggaac    960
gttccggagc tggcgccggc ggtgaggtac ctgaaaggct tcagcggatt ccacgagttc   1020
gcggagttca ccgcggagga cgtgggaacg agcgagagcg ggttgaactc ggtggttctg   1080
gcgaacaact cggagacggt gttgctgccg ctgaacgagc cggtttacgg aacgaagagg   1140
aagagccaga ttgagacgta tttggaacac aacgaaggtg ctggtgtgca gcaccttgcg   1200
cttgttactc acgacatctt caccacactg agagagatga gaaagcgaag tttccttggt   1260
ggatttgagt tcatgccttc tcctcctccc acctattacg ccaacctcca caaccgtgcc   1320
gctgatgtgt tgaccgttga ccagattaag cagtgtgagg agcttgggat tcttgttgac   1380
agagatgatc agggcactct gcttcagatt ttcactaagc ctgttgggga caggttcttc   1440
attttctgct tcttttttt ttttttgttt ttttaatccc tgctaaacaa ctttattata   1500
actctcacat tctattagcc tagccttgat gacttttaat ttacgttaaa ctgtgctttt   1560
tattctccta ctttgttagt ttttttttta tataaatttt taatttttca attataacctt  1620 tcaataatta acaaatgatg tacagtatag tgttatgtca gagtggatgt acttgatgta   1680
gcagttcatc agagtgtttc ccactacaaa ttgtacttt gtccctttcc tgacataaag   1740
tttacgacat tgaaaaaatt gatagataaa agtgcaattt atttatcttc cgctttgaac   1800
tgattgaaag tggtaaaagt tagattaaca atttgacagt gtttgtgtgt tggagggtgg   1860
tgattagtta aatgtgtttt gtgttgaatt gacaggccaa cgatattcat agagataatt   1920
cagaggatcg ggtgcatggt ggaggatgag gaagggaagg tgtaccagaa gggtgcatgt   1980 ggggttttg ggaaaggcaa tttttctgag cttttcaaat ccattgaaga atatgagaag   2040
actttggaag ctaaaagaac cgcg                                          2064
```